(12) United States Patent
Frycek et al.

(10) Patent No.: US 8,404,086 B2
(45) Date of Patent: Mar. 26, 2013

(54) PURIFICATION OF HYDROFORMYLATED AND HYDROGENATED FATTY ALKYL ESTER COMPOSITIONS

(75) Inventors: George J. Frycek, Midland, MI (US); Shawn D. Feist, Midland, MI (US); Timothy C. Frank, Midland, MI (US); Zenon Lysenko, Midland, MI (US); Joe D. Phillips, Lake Jackson, TX (US); Bruce W. Pynnonen, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 477 days.

(21) Appl. No.: 12/667,884

(22) PCT Filed: Jun. 20, 2008

(86) PCT No.: PCT/US2008/067585
§ 371 (c)(1),
(2), (4) Date: Jan. 13, 2010

(87) PCT Pub. No.: WO2009/009271
PCT Pub. Date: Jan. 15, 2009

(65) Prior Publication Data
US 2011/0031102 A1 Feb. 10, 2011

Related U.S. Application Data

(60) Provisional application No. 60/958,473, filed on Jul. 6, 2007.

(51) Int. Cl.
*B01D 3/00* (2006.01)
*B01D 1/22* (2006.01)

(52) U.S. Cl. ........... 203/39; 203/72; 203/75; 203/41; 202/173; 159/5; 159/49; 549/413

(58) Field of Classification Search ............ 203/41, 203/72, 75; 210/198.2, 283–285, 541, 656, 210/659; 549/413
See application file for complete search history.

(56) References Cited

U.S. PATENT DOCUMENTS

| | | | |
|---|---|---|---|
| 4,792,636 A * | 12/1988 | Hensman et al. | 568/492 |
| 5,616,735 A * | 4/1997 | Hunt | 549/413 |
| 5,660,691 A * | 8/1997 | Barnicki et al. | 203/72 |
| 5,958,849 A * | 9/1999 | Hewson et al. | 508/345 |
| 6,015,440 A | 1/2000 | Noureddini | |
| 6,156,197 A * | 12/2000 | Dessapt et al. | 210/198.2 |
| 6,878,837 B2 | 4/2005 | Bournay et al. | |
| 7,663,002 B2 * | 2/2010 | Peng et al. | 568/454 |
| 2004/0034244 A1 * | 2/2004 | Bournay et al. | 554/174 |
| 2007/0158270 A1 | 7/2007 | Geier et al. | |

(Continued)

FOREIGN PATENT DOCUMENTS

| | | |
|---|---|---|
| DE | 19742097 C1 | 12/1998 |
| WO | WO-03/038020 A1 | 5/2003 |

(Continued)

OTHER PUBLICATIONS

Http://www.chemicalprocessing.com/articles/2005/538/html.*

(Continued)

*Primary Examiner* — Duane Smith
*Assistant Examiner* — Ives Wu

(57) ABSTRACT

Effect separation of a composition of matter that includes at least two seed or plant oil derivatives into at least one desired product stream using at least two separation operations, which are independently selected from among several potential separation operations, in conjunction with at least one recycle stream from a separation operation.

12 Claims, 14 Drawing Sheets

U.S. PATENT DOCUMENTS

| | | | |
|---|---|---|---|
| 2007/0181504 | A1 | 8/2007 | Binder et al. |
| 2007/0277432 | A1 | 12/2007 | Jackam et al. |
| 2010/0255157 | A1* | 10/2010 | Arhancet et al. ............. 426/106 |

FOREIGN PATENT DOCUMENTS

| | | |
|---|---|---|
| WO | WO-2005/021697 A1 | 3/2005 |
| WO | WO-2007/075499 A2 | 7/2007 |
| WO | WO-2008/073729 A2 | 6/2008 |

OTHER PUBLICATIONS http://www.chemical processing.com/articles/2005/538/html.*

Lazzaroni, Michael J., et al., Revision of MOSCED Parameters and Extension to Solid Solubility Calculations, Ind. Eng. Chem. Res., 2005, pp. 4075-4083, vol. 44.

Triantafyllou, C., et al., The Design and Optimisatin of Fully Thermally Coupled Distillation Columns, Trans. IchemE, 1992, pp. 118-132, vol. 70.

Danner, R.P. et al., Critical Properties, Manual for Predicting Chemical Process Design Data, 1983, pp. 2-i-2K-2, Chapter 2, American Institute of Chemical Engineers, New York.

Danner, R.P., et al., Vapor Pressure, Manual for Predicting Chemical Process Design Data, 1983, pp. 3-i-3B-7, Chapter 3, American Institute of Chemical Engineers, New York.

Danner, R.P. et al., Density, Manual for Predicting Chemical Process Design Data, 1983, pp. 4-i-4E-1, Chapter 4, American Institute of Chemical Engineers, New York.

Danner, R.P. et al., Thermal Properties Preface, Manual for Predicting Chemical Process Design Data, 1983, pp. 5-i-5P-2, Chapter 5, American Institute of Chemical Engineers, New York.

Danner, R.P., et al., Surface Tension Preface, Manual for Predicting Chemical Process Design Data, 1983, pp. 7-i-7D-3, Chapter 7, American Institute of Chemical Engineers, New York.

Danner, R.P. et al., Viscosity, Manual for Predicting Chemical Process Design Data, 1983, pp. 8-iii-8H-1, Chapter 8, American Institute of Chemical Engineers, New York.

Danner, R.P., et al., Thermal Conductivity, Manual for Predicting Chemical Process Design Data, 1983, pp. 9-i-9I-2, Chapter 9, American Institute of Chemical Engineers, New York.

Peters, Max S., et al., Relative Merits of Plate and Packed Towers, Plant Design and Economics for Chemical Engineers, 1968, pp. 652-653, McGraw-Hill Book Company, New York.

Reid, Robert C., et al., Vapor Pressures and Enthalpies of Vaporization of Pure Fluids, The Properties of Gases and Liquids, 1987, pp. 181-222, Chapter 6, McGraw-Hill Book Company, New York.

International Search Report (PCT/US2008/067585).

* cited by examiner

PURIFICATION OF HYDROFORMYLATED AND HYDROGENATED FATTY ALKYL ESTER COMPOSITIONS

This application claims the benefit of U.S. Provisional Application No. 60/958,473 filed Jul. 6, 2007.

Subjecting a seed oil or vegetable oil to sequential operations of alkanolysis (e.g. methanolysis), hydroformylation and hydrogenation, yields a complex mixture of saturated and unsaturated compounds. These compounds have molecular weights that lead to high boiling points and low vapor pressures and often exhibit small differences in their volatility such that their separation via simple distillation becomes exceedingly difficult, impractical or economically unattractive. Boiling points in excess of 150 degrees centigrade (° C.) are typical. A combination of low relative volatilities and high boiling points poses a significant engineering challenge when one seeks to separate or reduce levels of one or more compounds from the complex mixture and brings into play a myriad of separation operation possibilities. Selection of a combination of separation operations that yields desirable component fractions, at least some of which, preferably most of which and more preferably substantially all of which, have a composition suitable for further processing or reactions, while minimizing both yield loss and generation of undesirable components (e.g. "bad heavies" (discussed below)) and remaining commercially viable or practical is far from straightforward.

An aspect of an invention embodied in appended claims is a method of separating at least one component from a composition that comprises at least two seed oil derivatives (e.g. fatty acid alkyl esters, hydrogenated fatty acid alkyl esters, hydroformylated fatty acid alkyl esters or hydroformylated and hydrogenated fatty acid alkyl esters), the method comprising steps:

a. subjecting the composition to a first separation operation, the first operation comprising a short contact time or low residence time evaporation, a low pressure (high vacuum) operation, a stripping operation, or a polarity driven separation operation, the first separation selectively partitioning the composition into a first portion and a first remainder;

b. subjecting the first remainder to at least one additional separation operation, the additional operation comprising a short contact time or low residence time evaporation, a low pressure operation, a stripping operation, or a polarity driven separation operation, each additional separation being the same as, or different from, each other and the first separation, the additional separation operation selectively partitioning the first remainder into at least one additional portion and at least one additional remainder, the additional portion being the same as, or different from, the first portion; and c. recycling at least a portion of the additional remainder to the first separation as a co-feed with the composition.

A preferred variation of the above method comprises a pre-treatment step that precedes step a. and comprises subjecting the composition to conditions sufficient to effectively de-gas the composition, thereby removing at least a portion of volatile compounds that have a normal boiling point (standard pressure and temperature) of less than 150° C., using methyl capronate as a dividing point for removing volatile methyl esters.

Irrespective of whether one practices the above method or its preferred variation, at least one of the first separation operation and an additional separation operation preferably effects separation of saturated components of the composition from monol (single hydroxyl moiety) and diol (two hydroxyl moieties) fractions of the composition by way of a simulated moving bed (SMB).

In one illustrative embodiment of the above method or its preferred variation, the first portion comprises monols and diols and an additional separation effects separation of the first portion into a monol-rich fraction and a diol-rich fraction by way of a SMB.

FIG. 1 is a schematic block diagram that illustrates a first separation operation that separates a composition into a mixture of diols and heavies as a first portion and a mixture of saturates and monols as a first remainder. FIG. 1 also shows an additional separation operation that separates the first remainder into a saturate fraction and a monol fraction.

FIG. 2 is a schematic block diagram that illustrates a first separation operation that separates a composition into a first portion that primarily, preferably substantially, comprises saturated compounds present in the mixture and a first remainder comprising monols, diols and heavies. FIG. 2 also shows an additional separation operation that separates the first remainder into a monol fraction and an additional remainder comprising diols and heavies.

Figure 1:
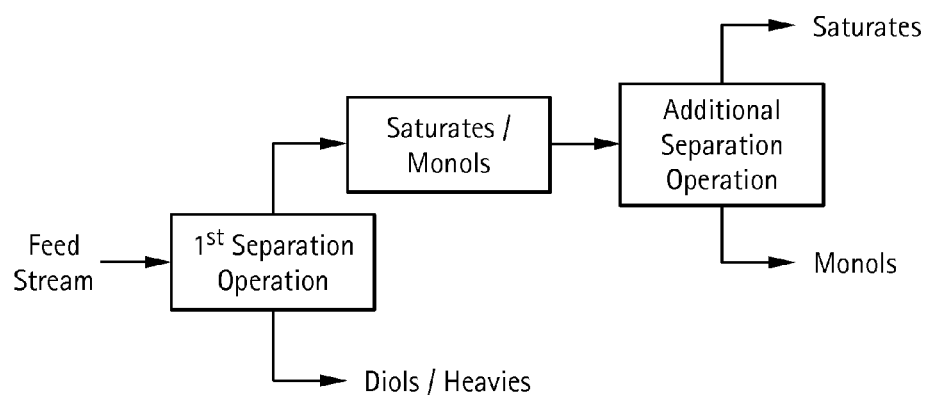
Figure 2:
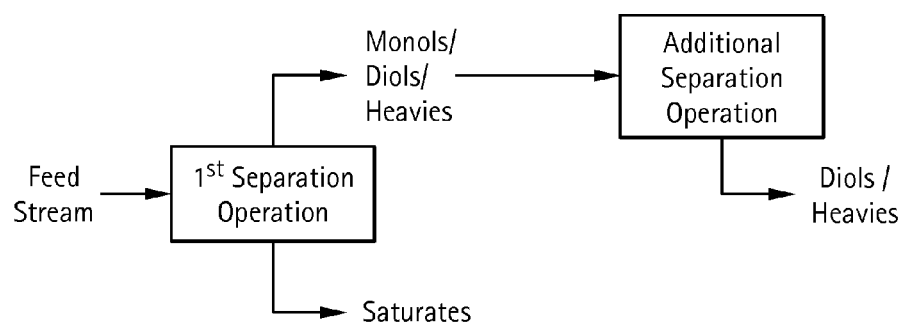

Expressions of temperature may be in terms either of degrees Fahrenheit (° F.) together with its equivalent in ° C. or, more typically, simply in ° C.

The short contact time or low residence time evaporation operation occurs via use of an apparatus selected from a group consisting of a falling film evaporator (FFE), a wiped film evaporator (WFE), a rolled film evaporator (RFE), a horizontal evaporator (HE), or a short path evaporator (SPE). The short contact time or low residence time evaporation operation preferably works in combination with rectification. While a boiling tube evaporator (BTE) may be used as a short contact time or low residence time evaporation apparatus if desired, solvent removal represents a more typical use of a BTE.

The low pressure (high vacuum) operation occurs via use of an apparatus selected from various forms of a packed tower distillation device. Such a device is preferably a packed tower distillation device that contains an ultra-low pressure drop packed section. Where packing is present in a section, the packing is preferably structured packing which typically comprises wire mesh or corrugated metal sheets that allow one to achieve higher mass transfer efficiency and a lower pressure drop, both relative to random-dumped packing. A packed section that contains structured packing also has a much lower pressure drop than a plurality of distillation trays due at least in part to a requirement to impose sufficient pressure to drive a gas flow through a liquid layer (also known as "liquid head") on each distillation tray.

The ultra-low pressure drop packed section has a pressure drop that is preferably less than or equal to ($\leqq$) 20 millimeters of mercury (mm Hg) (2.7 kilopascals (kPa)), more preferably $\leqq$15 mm Hg (2.0 kPa), still more preferably $\leqq$10 mm Hg (1.3 kPa) and even more preferably $\leqq$5 mm Hg (0.6 kPa). While certain pressure drop upper limits are noted above as preferred upper limits, all have a lower limit of greater than ($>$) 0 mm Hg ($>$0 kPa) and, by way of example, $\leqq$20 mm Hg necessarily includes all integers and real numbers $\leqq$20 and $>$0.

The stripping operation occurs via use of an apparatus selected from a group steam stripping device, an inert gas stripping device and a condensable vapor stripping device. Such a device may consist of a packed tower containing structured packing or random-dumped packing, a trayed tower containing distillation trays, or a vessel of any kind having provision for contacting steam, gas, or condensable vapor with the liquid phase.

The polarity driven separation operation occurs via use of a chromatographic separation device, preferably a SMB separation device.

In practice of the above method or its preferred variation, the first separation operation preferably occurs via a packed distillation tower and the first portion comprises saturates.

The additional separation operation preferably occurs via an apparatus comprising a series of cascaded SPE and rectifier combinations and the additional separation effects removal of at least a portion of monols and diols contained in the first remainder.

Other preferred options for respective first and additional separation operation combinations include: either a dividing wall column (DWC) or two low pressure distillation columns, one to remove saturates and monols from a seed oil derivative thereby leaving a fraction that comprises at least one diol and at least one heavy, and a second to separate saturates and monols to provide a monol rich portion, optionally with an intermediate SPE to remove heavies from the diols/heavies fraction; two low pressure distillation columns, one to remove saturates from a seed oil derivative thereby leaving a fraction that comprises at least one monol, at least one diol, and at least one heavy, and a second to separate monols from the fraction to provide a monol rich portion and a diols/heavies portion, optionally with a SPE following the second distillation column to remove heavies from the diols/heavies fraction; a low pressure distillation column and a SMB, the distillation column to remove saturates from a seed oil derivative thereby leaving a fraction that comprises at least one monol and at least one diol, and the SMB to separate monol(s) from the fraction to provide a monol-rich portion and a diol-rich portion, optionally in combination with one or more of a) a SPE to remove heavies from the seed oil derivative, thereby providing a purified seed oil derivative as a feed to the distillation column, b) a BTE and a distillation column to remove solvent from the monol-rich portion that exits the SMB, and c) a BTE and distillation column to remove solvent from the diol-rich portion that exits the SMB; a series of cascaded combinations of a SPE and a rectifier and a SMB, the series of cascaded SPE/rectifier combinations to remove saturates from a seed oil derivative thereby leaving a monol/diol fraction that comprises at least one monol and at least one diol, and the SMB to separate monols from the monol/diol fraction to provide a monol-rich portion and a diol-rich portion, optionally in combination with one or more of d) a SPE to remove heavies from the seed oil derivative, thereby providing a purified seed oil derivative as a feed to the distillation column, e) a BTE and distillation column to remove solvent from the monol-rich portion that exits the SMB, and f) a BTE and distillation column to remove solvent from the diol-rich portion resulting from the SMB; a series of cascaded SPE and rectifier combinations for the first separation operation and a packed distillation tower for the additional separation operation; a series of cascaded SPEs operating in series or with recycle; two SMBs, the first to remove saturates and monols from a seed oil derivative thereby leaving a diol/heavy fraction that comprises at least one diol and at least one heavy, and a second to separate saturates and monols to provide a monol-rich portion, optionally in combination with one or more of g) an intermediate SPE to remove heavies from the diol/heavy fraction, h) a BTE and distillation column to remove solvent from the monol-rich portion that exits the SMB, and i) a BTE and distillation column to remove solvent from the diol-rich portion that exits the SMB; a SMB and a low pressure distillation column or a series of SPE/rectifier combinations, the SMB to separate saturates and monols as a first fraction from a seed oil derivative, thereby leaving a leaving a second or diol-rich fraction that comprises at least one diol, and the distillation column or series of cascaded SPE/rectifier combinations (also referred to as "evaporators with rectified sections") to separate saturates from the first fraction providing a monol-rich portion, optionally with one or more of j) a boiling tube evaporator and a distillation column to remove solvent from the diol-rich fraction, k) a BTE and distillation column to remove solvent from the monol rich portion, and l) a BTE to remove heavies from the seed oil derivative, thereby resulting in a purified seed oil derivative feed to the SMB. Skilled artisans may use guidance provided by these preferred options to select other suitable apparatus choices for the first and additional separation operations from among the devices disclosed herein and their variations.

When using a SMB to effect separation, one may select from a variety of combinations of solvent and media, some more effective than others. Skilled artisans who work with SMB apparatus readily understand use of both solvent and media. For purposes of the present invention, select desirable solvents or mixtures of solvents characterized by a MOSCED polarity parameter, tau (t), that lies within a range of from 4 to 12 Joules per milliliter $(J/mL)^{0.5}$, a MOSCED acidity parameter, alpha ($\alpha$), that lies within a range of from 0 $(J/mL)^{0.5}$ to 6 $(J/mL)^{0.5}$, and a basicity parameter, beta ($\beta$), that lies within a range of from 1 $(J/mL)^{0.5}$ to 12 $(J/mL)^{0.5}$. The foregoing solvents or mixtures of solvents provide very effective results when used in conjunction with absorbent media selected from silica gel or alumina or ion-exchange beads. See M. L. Lazzaroni et al., "Revision of MOSCED Parameters and Extension to Solid Solubility Calculations", Ind. Eng. Chem. *Res.*, vol 44(11), pages 4075-4083 (2005) for a more detailed explanation of $\tau$, $\alpha$ and $\beta$.

A combination of ethyl acetate as solvent and silica gel as media provides very satisfactory results when used in conjunction with a SMB. Other suitable combinations include acetonitrile as solvent and silica gel as media, methyl isobutyl ketone (MIBK) as solvent and silica gel as media, tetrahydrofuran (THF) as solvent and silica gel as media, methyl tert-butylether (MTBE) as solvent and silica gel as media, toluene as solvent and silica gel as media; and a mixture of heptane and ethanol as solvent and alumina as media. The foregoing combinations represent preferred combinations, but do not constitute an exhaustive list of all possible combinations of solvent and media that may be used with greater or lesser success in terms of effectiveness per dollar spent on the combination.

The seed oil derivative may be any of a variety of derivatives including fatty acid alkyl esters, hydrogenated fatty alkyl esters, hydroformylated fatty acid alkyl esters or hydroformylated and hydrogenated fatty acid alkyl esters. The seed oil derivative is preferably a hydroformylated and hydrogenated fatty acid alkyl ester or seed oil alcohol derivative. Methyl esters represent a preferred species of alkyl esters for purposes of the present invention.

The seed oil derivative may be prepared from any of a number of plant (e.g. vegetable), seed, nut or animal oils including, but not limited to palm oil, palm kernel oil, castor oil, vernonia oil, lesquerella oil, soybean oil, olive oil, peanut oil, rapeseed oil, corn oil, sesame seed oil, cottonseed oil, canola oil, safflower oil, linseed oil, sunflower oil; high oleic oils such as high oleic sunflower oil, high oleic safflower oil, high oleic corn oil, high oleic rapeseed oil, high oleic soybean oil and high oleic cottonseed oil; genetically-modified variations of oils noted in this paragraph, and mixtures thereof. Preferred oils include soybean oil (both natural and genetically-modified), sunflower oil (including high oleic) and canola oil (including high oleic). Soybean oil (whether natural, genetically modified or high oleic) represents an especially preferred seed oil. As between a high oleic oil and its natural oil counterpart (e.g. high oleic soybean oil versus soybean oil), the high oleic oil tends to have a simpler, albeit still complex, mixture of components that makes separation of a composition comprising the high oleic oil easier than separation of a composition comprising the natural oil counterpart of the high oleic oil.

Selecting separation technology and associated apparatus and apparatus sequencing and connectivity for use in effecting recovery or separation of a component or a plurality of different components from a composition that comprise at least two seed oil derivatives, more often several seed oil derivatives, constitutes a complex and many-faceted challenge. Facets include, but are not limited to, heat history, pressure drop, waste production, productivity, feedstock composition, feedstock flexibility, product stream flexibility, selectivity, presence or absence of packing in certain apparatus, apparatus or combination of apparatus choices, and economics. Several of the facets compete with each other. For example, recovering or separating a single component, such as a monol, from a mixture of several seed oil derivatives, while technically feasible provided one does not care about consequences such as low yield, generation of unwanted byproducts due to excessive heat history, or dealing with disposition or use of other components of the mixture of seed oil derivatives, may at the same time be, for example, environmentally unacceptable, economically unattractive or both.

C. Triantafyllou and R. Smith, in an article entitled "The Design and Optimisation of Fully Thermally coupled Distillation Columns", *Trans I ChemE*, volumn 70, Part A, pages 118-132 (March 1992), teach that for most separations, fully thermally coupled distillation columns, also known as "dividing wall columns" or as "Petlyuk columns", are thermodynamically more efficient than conventional arrangements of multiple distillation columns. They also teach, at page 118, that "capital savings result from use of a single reboiler and condenser compared with a conventional arrangement".

Major components of interest in compositions subjected to the foregoing process include the following where (I) represents a monol, (II) represents a diol and (III) represents a triol. Skilled artisans recognize that (I), (II) and (III) each represent one of at least two positional isomers. The present invention includes all such positional isomers. Potential positional isomer locations occur in a molecule of a fatty acid methyl ester derived from a seed oil, which seed oil typically contains a measurable fraction of 16 carbon atom ($C_{16}$), 18 carbon atom ($C_{18}$) and 20 carbon atom ($C_{20}$) chains, between carbon atoms 9 and 10 ($C_9/C_{10}$), 12 and 13 ($C_{12}/C_{13}$) and 15 and 16 ($C_{15}/C_{16}$). See, e.g.:

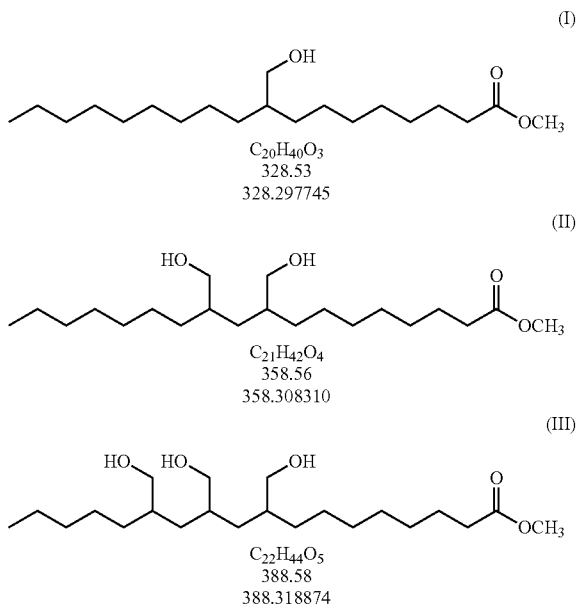

as well as saturates such as the following or their isomers:

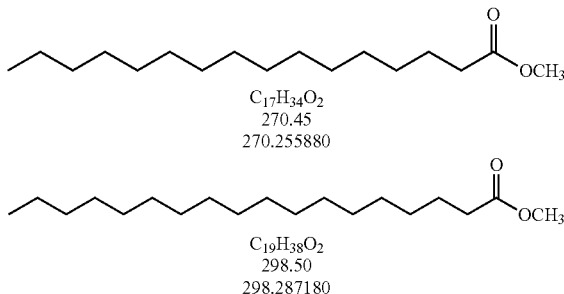

Additional components of the above compositions include cyclic ethers such as the following or their isomers (including positional isomers):

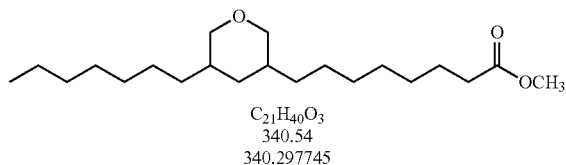 [SMILES: CCCCCCCC1COCC(CCCCCCCC(=O)OC)C1]

$C_{21}H_{40}O_3$
340.54
340.297745 as well as lactols such as the following or their isomers (including positional isomers:

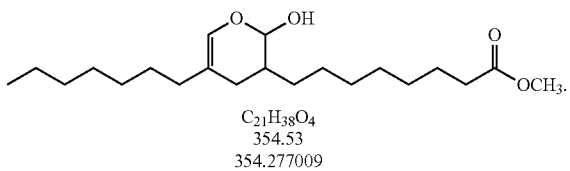 [SMILES: CCCCCCCC1=COC(O)C(CCCCCCCC(=O)OC)C1]

$C_{21}H_{38}O_4$
354.53
354.277009

Skilled artisans sometimes refer to high molecular weight species or molecules as "heavies". Alternately, "heavies" refers to oligomers or oligomeric esters that have a higher vapor pressure than, for example, vapor pressure of principal components of a monol-rich stream. The present invention divides heavies into two groups, nominally "good heavies" and "bad heavies", based respectively upon presence or absence of hydroxy (OH) functionality suitable for creation of polyols via polymerization. Good heavy production involves a head-to-tail reaction between a hydroxy group-functionalized monomer and an ester group-functionalized second monomer. Bad heavies result from reactions between reactants, products or both present during one or more of hydroformylation, hydrogenation and monomer recovery.

Bad heavies, when present in a composition, tend to adversely affect physical properties of the composition when used in downstream applications of the composition, especially when such downstream applications involve conditions such as a temperature sufficient to effect a reaction between a bad heavy and another component of the composition. Good heavies, on the other hand, do not have a significant adverse impact upon physical properties of the composition when used in many downstream applications even if they react with other components of the composition.

In order to limit adverse effects that result from presence of "bad" heavies, one may do either or both of minimizing heavy production and removing at least a portion of heavies present in a product or intermediate product. Skilled artisans recognize that removal or separation of heavies necessarily applies to both "good" and "bad" heavies. An optional, sometimes preferred, variation of the above-noted aspect of the invention involves removing at least a portion of heavies present in the additional remainder before recycling at least a portion of said additional remainder to the first separation as a co-feed with the composition.

Skilled artisans recognize that several techniques exist to effect separation of heavies from the additional remainder. While two of such techniques find particular favor when applied to the present invention, other techniques may be used in place of or in combination with either of both of the said two techniques. One of the two techniques, especially useful when dealing with hydrogenation effluent that contains "good heavies" relies upon relative volatility differences between the good heavies, which tend to have a high boiling point relative to hydroxy-functional components present in a composition that have a comparable hydroxy-functionality, yet do not have a molecular weight sufficient to classify them as "heavies". The other of the two techniques employs a polarity driven device to concentrate species that have similar functional make-ups based upon differences in polarity rather than differences in volatility and preferentially remove "bad heavies". Skilled artisans also recognize that, subsequent to separation, heavies in general and good heavies in particular may be converted to monomer form via methods such as methanolysis, polymerized to generate a useful downstream product or recycled for further processing as noted above. While either technique may be used alone, the two techniques may be used in combination with each other, with another existing technique or both.

Peters and Timmerhaus, in *Plant Design and Economics for Chemical Engineers*, McGraw Hill (1968), provide teachings relative to merits of a plate distillation tower versus a packed distillation tower and suggest that an optimum tower choice involves consideration of a detailed cost analysis as well as selection of optimum operating conditions. They allow substitution of a qualitative analysis of column internal options to replace the cost analysis. They emphasize desirability of packed tower use where low liquid hold-up (low residence time) and reduced pressure drop (low or reduced boiling point) are prime considerations.

From the teachings of Peters and Timmerhaus, a logical conclusion is that distillation of high boiling monomers that have a potential to thermally degrade imposes a design constraint that mandates use of low pressure and minimal residence time. Skilled artisans recognize that each organic component has a degradation temperature (e.g. a temperature above which the component tends to degrade at an unacceptable rate and/or an unacceptable extent). "Low pressure" allows for distillation to take place at a temperature below the temperature of decomposition and "minimal residence time" means a time shorter than that time at which the extent of degradation becomes unacceptable. When the method of separation noted above involves use of a distillation tower to effect a separation or partitioning of seed oil derivatives, the distillation tower is preferably a packed distillation tower. The packed distillation tower may be, for example, either a simple distillation tower or a DWC.

When the separation method yields a mixture that has a low saturate content and a high monol content as one of the first portion, an additional portion or an additional remainder, such a mixture finds utility in producing flexible polyurethane products. If the mixture is low in saturates and monols and high in diols, it has utility in producing molded (rigid) parts.

Modeling Hydroformylated—Hydrogenated Seed Oil Derivative Separation Options

Use a combination of process flowsheet development approaches based upon commercially available and industrially recognized process engineering simulation tools and software developed by AspenTech including, but not limited to, Aspen Plus™ 2004.1 and Aspen Dynamics™ 2004.1. For a given process or process step, process input parameters that support a mathematical representation of a specific unit operation include physical connections, hydraulics, performance specifications (e.g. purity and pressure drop limitations) and thermodynamic properties (e.g. heat capacity, heat of vaporization and vapor pressure) of chemicals being processed using equipment associated with the specific unit operation. This approach works well for unit operations such as evaporation, mixing, distillation, heat exchange and pumping.

The AspenTech simulation tools and software include chemical and physical properties for a number of materials. The collection of included materials, while extensive, must be supplemented for purposes of the present invention, either by actual measurements or properties for certain materials or by estimates of such measurements or properties. Illustrative estimates include gas chromatograph (GC) retention times as well as extrapolation of curves from experimental data and use of physical property estimation techniques such as group contribution models. For guidance on estimates and previously developed physical property information, see, respectively, Danner et al, *Manual for Predicting Chemical Process Design Data*, DIPPR (AIChE), New York, (1983) and Reid et al., *The Properties of Gases and Liquids*, 4$^{th}$ Ed, McGraw-Hill, New York (1987).

Accomplish simulation of WFE and short-path evaporation SPE, neither of which is included among AspenTech simulation tools and software, by combining existing vapor liquid equilibrium (VLE) models into a functional single unit operation that accounts for the behavior of either a WFE or a SPE.

Model simulation of a WFE by first combining a series of Aspen Plus flash blocks specifying pressure and vapor fraction to provide a set of modeled results and then comparing the set of modeled results with experimental results achieved by an operating WFE. Each flash block has a liquid stream that is fed to the next flash block in the series. Each flash block, has a vapor stream and all flash block vapor streams, when taken together, form a combined vapor stream for purposes of modeling evaporator behavior.

For SPE simulation, use the approach detailed above for WFE simulation, but recognize that differences in performance and operation of a SPE relative to a WFE (e.g. combine and condense the combined vapor stream at an internal heat exchange temperature associated with the SPE in operating the SPE versus an external heat exchanger in an operating WFE) necessarily lead to differences in modeling results. This approach to simulation allows one to model several SPE or WFE unit operations in series or in parallel.

Examples contained herein (e.g. Ex 31 below) model the performance of a SPE by using a series of four cascaded Aspen Plus flash blocks with a residue stream from one flash block feeding the next flash block in the cascade for residue streams from the first three flash blocks and vapor streams from the four blocks being combined and condensed. The examples also model a WFE is modeled as a single flash block or evaporator. Skilled artisans understand that, when compared to modeling data, operation of various vendor-supplied apparatus, such as WFE or SPE, may differ from modeling projections with some operations being more efficient and others being less efficient. Skilled artisans also understand that some vendor-supplied apparatus may differ in terms of having a unit operation identical to, for example, four cascaded flash blocks, in that a vendor may choose a unit operation more accurately modeled by a greater or lesser number of flash blocks. Nonetheless, the modeling data provides a very useful guide in selecting apparatus and using the same in accord with the present invention.

Modeling of SMB operations, also excluded from AspenTech simulation tools and software, employs a different approach that begins with collecting experimental data from an SMB separation and converting that experimental data into empirical relationships. The empirical relationships allow one to include SMB as part of a simulated separation operation without directly using thermodynamic or absorption properties as input for AspenTech simulation tools and software to simulate a SMB separation. As an added benefit, use of the empirical relationships allows one to model a complete separation that includes feedstream to the SMB and a product stream from the SMB.

Selection of the appropriate simulation modeling approach allows one to begin with a multi-component composition, such as one that includes at least two seed oil derivatives, and model production of a desired produced product stream or range of desired produced product streams.

EXAMPLES

Use one of four feed (seed oil alcohol derivative) compositions detailed in Table 1 below for all succeeding examples other than Ex 19 through Ex 22. Table 1 identifies composition components or fractions either specifically, as in methyl palmitate, or generically, as in monols, and provides an identifier or "Aspen Alias" along with weight fractions of each composition component or fraction. In this Example section, use a component name or a fraction name interchangeably with its Aspen Alias. In other words, use the component or fraction name with or without its Aspen Alias as in using the Aspen Alias alone without changing the spirit or scope of this invention or the examples that illustrate this invention. The four seed oils are soybean oil (commercially available from AG Environmental Products, under the trade designation SOYCLEAR™ 1500), hydroformylated soybean oil, canola oil (commercially available from AG Environmental Products, under the trade designation CANOLAGOLD™ CE-110) and sunflower oil (commercially available from ACH Food Companies, under the trade designation TRISUN EXTRA™ RBWD).

TABLE 1

| Name | Aspen Alias | Feed Stream A - Soy Oil Derivative (Soy Oil Alcohol Monomer) | Feed Stream B - HF Soy Oil Derivative (HF Soy Oil Alcohol Monomer) | Feed Stream C - Canola Oil Derivative (Canola Oil Alcohol Monomer) | Feed Stream D - Sunflower Oil Derivative (Sunflower Oil Alcohol Monomer) |
|---|---|---|---|---|---|
| Methyl Palmitate | C16SA-ME | 0.11 | 0.05 | 0.06 | 0.035 |
| Methyl Stearate | C18SA-ME | 0.18 | 0.10 | 0.15 | 0.045 |
| Monols | 18MHM-ME | 0.39 | 0.33 | 0.57 | 0.85 |
| Diols | 18DHM-ME | 0.28 | 0.46 | 0.15 | 0.05 |

TABLE 1-continued

| Name | Aspen Alias | Feed Stream A - Soy Oil Derivative (Soy Oil Alcohol Monomer) | Feed Stream B - HF Soy Oil Derivative (HF Soy Oil Alcohol Monomer) | Feed Stream C - Canola Oil Derivative (Canola Oil Alcohol Monomer) | Feed Stream D - Sunflower Oil Derivative (Sunflower Oil Alcohol Monomer) |
|---|---|---|---|---|---|
| Triols | 18THM-ME | 0.015 | 0.05 | 0.05 | 0.01 |
| Heavies | Heavies | 0.025 | 0.01 | 0.02 | 0.01 |
| Total | | 1.00 | 1.00 | 1.00 | 1.00 |

Figure 3:
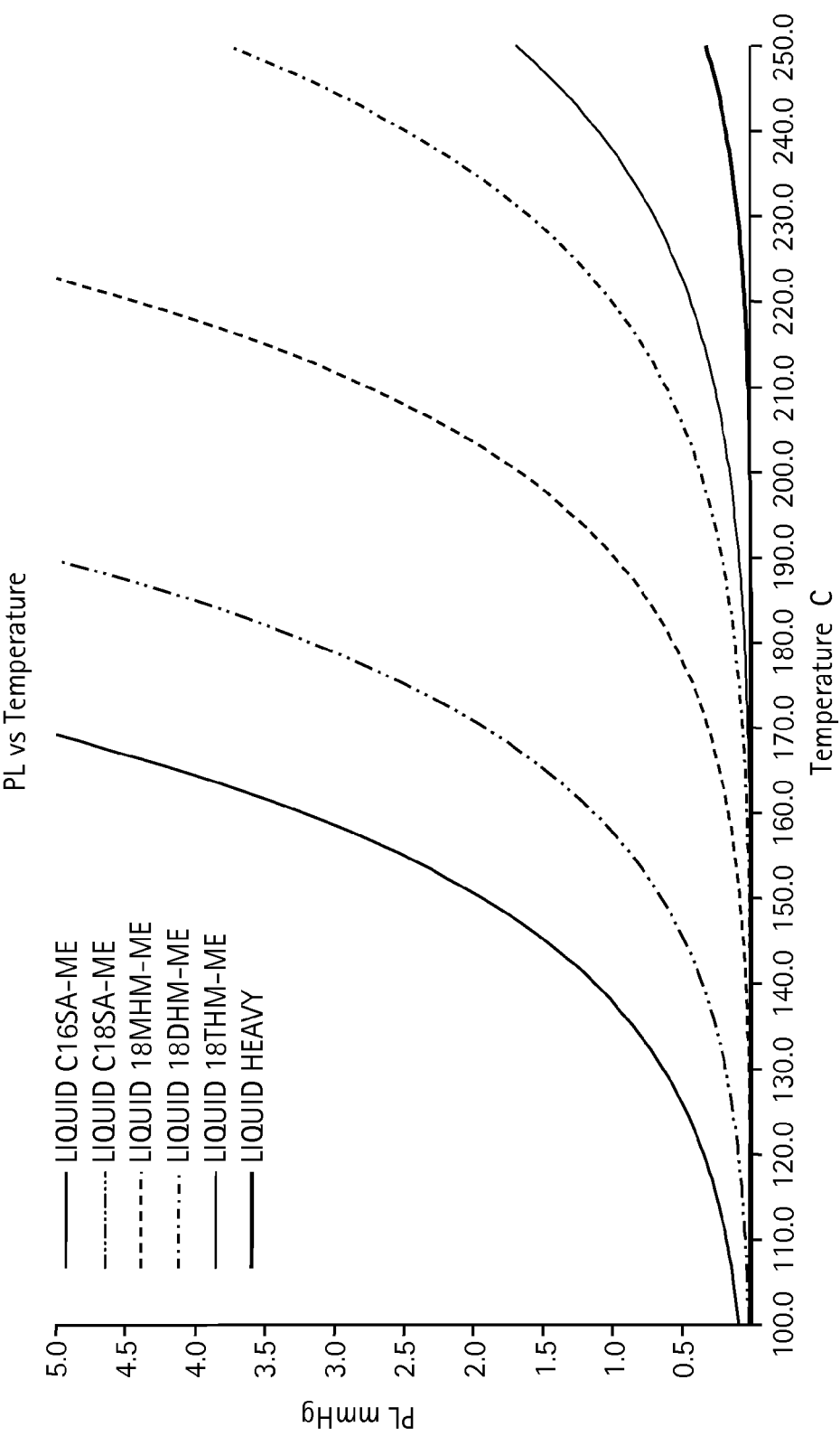
FIG. 3 is a graphic portrayal of vapor pressure of the components/fractions identified in Table 1 below.

In modeling distillation equipment for use in modeling a separation process, vapor pressure constitutes a primary, if not the principle, driving force. See FIG. 3 below for a graphic portrayal of vapor pressure of the components/fractions identified in Table 1 above.

(Ex) 1

Figure 4:
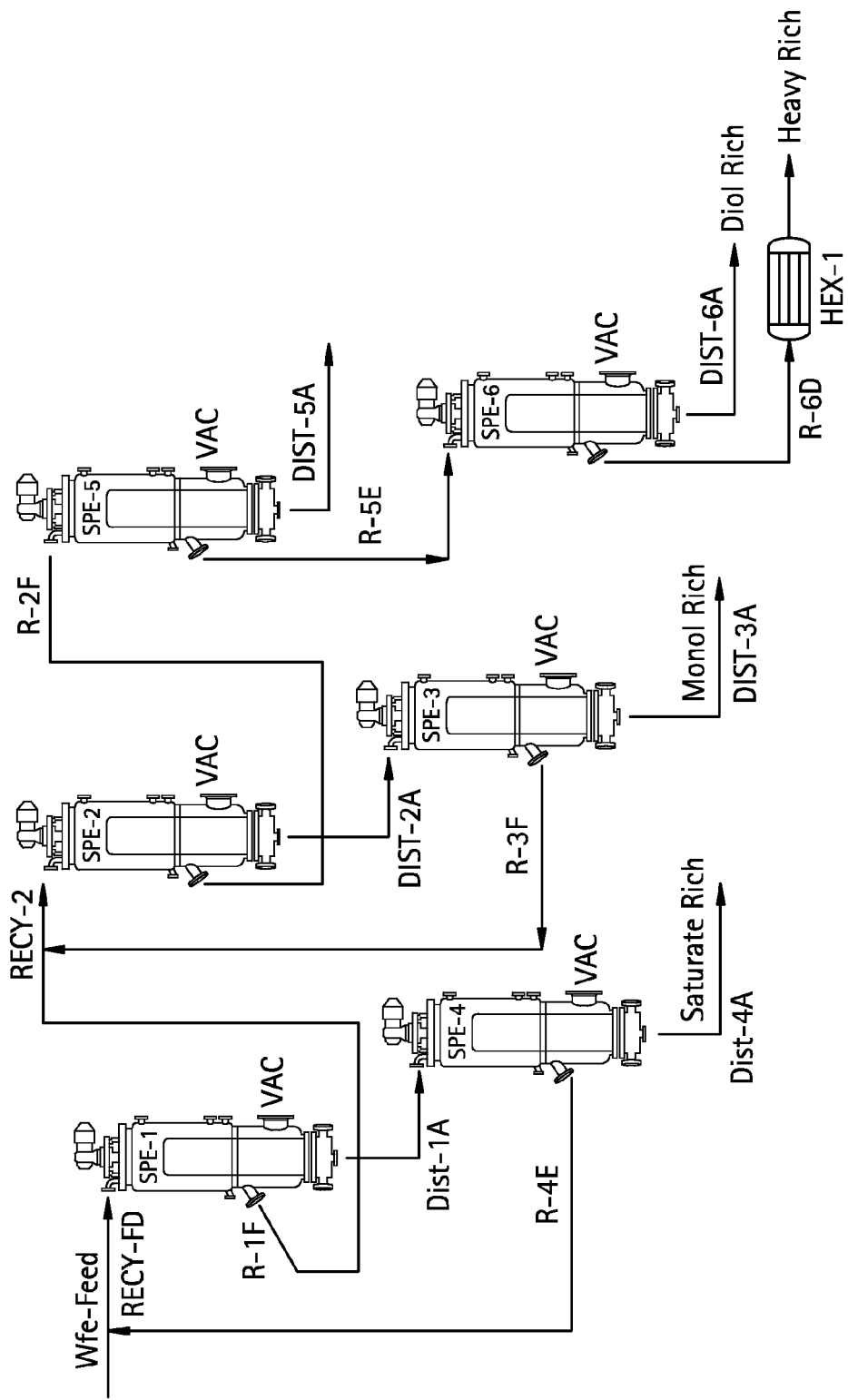
FIG. 4 is a schematic illustration of a series of cascaded SPE combinations in conjunction with recycle as used in Example (Ex) 1 through Ex 4 below.

Simulation of Cascaded SPE Combinations in Conjunction with Recycle—Feed Stream A Connect six SPEs, numbered SPE-1 through SPE-6 in a cascaded and recycle mode to simulate continuous operation to effect separation of Feed Stream A (see Table 1 above). Table 2 below summarizes effluent composition from each of SPE-1 through SPE-6. See FIG. 4 below for a schematic illustration of the connected SPEs where distillate (Dist) or a remaining fraction (F) or extract (E) that cascades from one SPE, e.g. SPE-1, to a sequential SPE, in this case SPE-2 and SPE-4, bears a label linking it to the SPE that generates the distillate, in this case Dist-1A feeds to SPE-4 and R-1F.

"WFE-Feed" represents a feedstream from a WFE. Introduce the feedstream and, once it becomes available through operation of the connected SPEs, R-4E to SPE-1. Operate SPE-1 with a driving force sufficient to result in a mass distillate:feed (D:F) ratio of 0.875. Operating SPE-1 effects separation of its feedstream into Dist-1A and R-1F. Feed Dist-1A to SPE-4 and R-1F to SPE-2 together with, once it becomes available through operation of the connected SPEs, R-3F as a feedstream for SPE-2. Similarly, Dist-2A feeds to SPE-3 and R-2F feeds to SPE-5. Operate SPE-2 through SPE-6 with driving forces sufficient to result in respective D:F ratios as follows: SPE-2=0.928, SPE-5=0.803, SPE-6=0.632, SPE-4=0.062 and SPE-3=0.051. In operation of, for example, SPE-2, Dist-2A constitutes a feedstream for SPE-3 and R-2F constitutes a feedstream for SPE-5. SPE-5 yields a purge stream (Dist-5A) with a monol:diol weight ratio of 65:32 and a feedstream for SPE-6 (R-5E). SPE-6 yields a diol-rich stream (Dist-6A) and a stream (R-6D) that passes through a heat exchanger (HEX-1) to yield a heavy-rich stream. SPE-4 yields a saturate-rich stream (Dist-4A) and SPE-3 yields a monol-rich stream (Dist 3A).

TABLE 2

| Feed Stream A | | | | | | | |
|---|---|---|---|---|---|---|---|
| Mass Fraction Aspen Alias | WFE-Feed | Dist-1A | Dist-2A | Dist-3A | Dist-4A | Dist-5A | Dist-6A |
| C16 SA-ME | 0.110 | 0.093 | 0.000 | 0.000 | 0.363 | 0.000 | 0.000 |
| C18 SA-ME | 0.180 | 0.462 | 0.002 | 0.012 | 0.583 | 0.000 | 0.000 |
| 18 MHM-ME | 0.390 | 0.410 | 0.885 | 0.962 | 0.052 | 0.323 | 0.016 |
| 18 DHM-ME | 0.280 | 0.036 | 0.111 | 0.026 | 0.001 | 0.650 | 0.865 |
| 18 THM-ME | 0.015 | 0.001 | 0.002 | 0.000 | 0.000 | 0.024 | 0.084 |
| HEAVY | 0.025 | 0.000 | 0.000 | 0.000 | 0.000 | 0.002 | 0.034 |
| Total Flow (kg/hr) | 1000 | 4885.6 | 5415.8 | 273.8 | 302.9 | 339.9 | 52.6 |
| Temperature (° C.) | 100 | 50 | 50 | 50 | 50 | 50 | 50 |
| Pressure (mmHg) | 0.1 | 0.1 | 0.1 | 760 | 760 | 760 | 760 |
| Mass Fraction Aspen Alias | Heavies | R-1F | R-2F | R-3F | R-4E | R-5E | R-6D |
| C16 SA-ME | 0.000 | 0.000 | 0.000 | 0.000 | 0.075 | 0.000 | 0.000 |
| C18 SA-ME | 0.000 | 0.005 | 0.000 | 0.001 | 0.454 | 0.000 | 0.000 |
| 18 MHM-ME | 0.000 | 0.537 | 0.262 | 0.881 | 0.433 | 0.010 | 0.000 |
| 18 DHM-ME | 0.198 | 0.401 | 0.644 | 0.116 | 0.038 | 0.619 | 0.198 |
| 18 THM-ME | 0.074 | 0.022 | 0.035 | 0.002 | 0.001 | 0.080 | 0.074 |
| HEAVY | 0.727 | 0.036 | 0.059 | 0.000 | 0.000 | 0.290 | 0.727 |
| Total Flow (kg/hr) | 30.7 | 697.1 | 423.2 | 5142.0 | 4582.7 | 83.3 | 30.7 |

TABLE 2-continued

| | Feed Stream A | | | | | | |
|---|---|---|---|---|---|---|---|
| Temperature (° C.) | 50 | 158.1 | 165.6 | 153.6 | 123.8 | 181.2 | 198.0 |
| Pressure (mmHg) | 0.1 | 0.1 | 0.1 | 0.1 | 0.1 | 0.1 | 0.1 |

Ex 2 through 4

Replicate Ex 1 with changes to D:F ratios and, respectively Feed Stream B for Ex 2, Feed Stream C for Ex 3 and Feed Stream D for Ex 4. See Table 1 above for composition of each Feed Stream. Tables 3 through 5 below summarize effluent data for each of SPE-1 through SPE-6 for, respectively, Ex 2 through Ex 4 using the same format as in Table 1 above.

In Ex 2, operate SPE-1 with sufficient driving force to yield a D:F ratio of 0.777, operate SPE-2 to yield a D:F ratio of 0.466, operate SPE-5 to yield a D:F ratio of 0.812, operate SPE-6 to yield a D:F ratio of 0.742, operate SPE-4 to yield a D:L ratio of 0.061, and operate SPE-3 to yield a D:F ratio of 0.216.

In Ex 3, operate SPE-1 with sufficient driving force to yield a D:F ratio of 0.857, operate SPE-2 to yield a D:F ratio of 0.900, operate SPE-5 to yield a D:F ratio of 0.798, operate SPE-6 to yield a D:L ratio of 0.716, operate SPE-4 to yield a D:F ratio of 0.051, and operate SPE-3 to yield a D:L ratio of 0.262.

In Ex 4, operate SPE-1 with sufficient driving force to yield a D:F ratio of 0.864, operate SPE-2 to yield a D:F ratio of 0.905, operate SPE-5 to yield a D:F ratio of 0.800, operate SPE-6 to yield a D:F ratio of 0.711, operate SPE-4 to yield a D:F ratio of 0.0531, and operate SPE-3 to yield a D:F ratio of 0.264.

Ex 1-4 and the data presented in Tables 2 through 5 demonstrate effective separation of feed streams that represent four different seed oil derivatives (seed oil alcohol monomers) using a series of cascaded SPE combinations with recycle.

TABLE 3

| | Feed Stream B | | | | | | |
|---|---|---|---|---|---|---|---|
| Mass Fraction Aspen Alias | WFE-Feed | Dist-1A | Dist-2A | Dist-3A | Dist-4A | Dist-5A | Dist-6A |
| C16 SA-ME | 0.050 | 0.048 | 0.000 | 0.000 | 0.285 | 0.000 | 0.000 |
| C18 SA-ME | 0.100 | 0.262 | 0.002 | 0.008 | 0.563 | 0.000 | 0.000 |
| 18 MHM-ME | 0.330 | 0.586 | 0.734 | 0.913 | 0.146 | 0.325 | 0.018 |
| 18 DHM-ME | 0.460 | 0.100 | 0.253 | 0.077 | 0.005 | 0.628 | 0.830 |
| 18 THM-ME | 0.050 | 0.004 | 0.011 | 0.001 | 0.000 | 0.046 | 0.147 |
| HEAVY | 0.010 | 0.000 | 0.000 | 0.000 | 0.000 | 0.001 | 0.005 |
| Total Flow (kg/hr) | 1000 | 2878.2 | 604.7 | 130.3 | 175.5 | 563.9 | 96.6 |
| Temperature (° C.) | 100 | 50 | 50 | 50 | 50 | 50 | 50 |
| Pressure (mmHg) | 0.1 | 0.1 | 0.1 | 760 | 760 | 760 | 760 |

| Mass Fraction Aspen Alias | Heavies | R-1F | R-2F | R-3F | R-4E | R-5E | R-6D |
|---|---|---|---|---|---|---|---|
| C16 SA-ME | 0.000 | 0.000 | 0.000 | 0.000 | 0.033 | 0.000 | 0.000 |
| C18 SA-ME | 0.000 | 0.001 | 0.000 | 0.000 | 0.242 | 0.000 | 0.000 |
| 18 MHM-ME | 0.000 | 0.369 | 0.267 | 0.685 | 0.615 | 0.014 | 0.000 |
| 18 DHM-ME | 0.439 | 0.557 | 0.647 | 0.301 | 0.106 | 0.729 | 0.439 |
| 18 THM-ME | 0.285 | 0.061 | 0.072 | 0.014 | 0.004 | 0.182 | 0.285 |
| HEAVY | 0.276 | 0.012 | 0.014 | 0.000 | 0.000 | 0.075 | 0.276 |
| Total Flow (kg/hr) | 33.6 | 824.5 | 694.2 | 474.3 | 2702.8 | 130.2 | 33.6 |
| Temperature (° C.) | 50 | 162.3 | 165.4 | 156.3 | 132.5 | 178.5 | 185.0 |
| Pressure (mmHg) | 760 | 0.1 | 0.1 | 0.1 | 0.1 | 0.1 | 0.1 |

TABLE 4

Feed Stream C

| Mass Fraction Aspen Alias | WFE-Feed | Dist-1A | Dist-2A | Dist-3A | Dist-4A | Dist-5A | Dist-6A |
|---|---|---|---|---|---|---|---|
| C16 SA-ME | 0.060 | 0.049 | 0.000 | 0.000 | 0.256 | 0.000 | 0.000 |
| C18 SA-ME | 0.150 | 0.352 | 0.001 | 0.005 | 0.630 | 0.000 | 0.000 |
| 18 MHM-ME | 0.570 | 0.578 | 0.827 | 0.950 | 0.113 | 0.183 | 0.002 |
| 18 DHM-ME | 0.150 | 0.019 | 0.152 | 0.043 | 0.001 | 0.625 | 0.372 |
| 18 THM-ME | 0.050 | 0.002 | 0.019 | 0.002 | 0.000 | 0.184 | 0.428 |
| HEAVY | 0.020 | 0.000 | 0.000 | 0.000 | 0.000 | 0.007 | 0.197 |
| Total Flow (kg/hr) | 1000 | 4573.9 | 2053.2 | 537.0 | 234.1 | 182.5 | 33.1 |
| Temperature (° C.) | 100 | 50 | 50 | 50 | 50 | 50 | 50 |
| Pressure (mmHg) | 0.1 | 0.1 | 0.1 | 760 | 760 | 760 | 760 |

| Mass Fraction Aspen Alias | Heavies | R-1F | R-2F | R-3F | R-4E | R-5E | R-6D |
|---|---|---|---|---|---|---|---|
| C16 SA-ME | 0.000 | 0.000 | 0.000 | 0.000 | 0.037 | 0.000 | 0.000 |
| C18 SA-ME | 0.000 | 0.003 | 0.000 | 0.000 | 0.337 | 0.000 | 0.000 |
| 18 MHM-ME | 0.000 | 0.710 | 0.147 | 0.784 | 0.603 | 0.002 | 0.000 |
| 18 DHM-ME | 0.008 | 0.196 | 0.553 | 0.191 | 0.019 | 0.269 | 0.008 |
| 18 THM-ME | 0.068 | 0.065 | 0.213 | 0.025 | 0.003 | 0.326 | 0.068 |
| HEAVY | 0.924 | 0.026 | 0.087 | 0.000 | 0.000 | 0.404 | 0.924 |
| Total Flow (kg/hr) | 13.1 | 765.8 | 228.7 | 1516.2 | 4339.8 | 46.3 | 13.1 |
| Temperature (° C.) | 50 | 155.6 | 171.0 | 155.0 | 129.2 | 189.6 | 221.1 |
| Pressure (mmHg) | 760 | 0.1 | 0.1 | 0.1 | 0.1 | 0.1 | 0.1 |

TABLE 5

Feed Stream D

| Mass Fraction Aspen Alias | WFE-Feed | Dist-1A | Dist-2A | Dist-3A | Dist-4A | Dist-5A | Dist-6A |
|---|---|---|---|---|---|---|---|
| C16 SA-ME | 0.035 | 0.013 | 0.000 | 0.000 | 0.140 | 0.000 | 0.000 |
| C18 SA-ME | 0.045 | 0.037 | 0.000 | 0.000 | 0.179 | 0.000 | 0.000 |
| 18 MHM-ME | 0.850 | 0.942 | 0.973 | 0.993 | 0.680 | 0.820 | 0.229 |
| 18 DHM-ME | 0.050 | 0.007 | 0.025 | 0.006 | 0.001 | 0.160 | 0.581 |
| 18 THM-ME | 0.010 | 0.001 | 0.002 | 0.000 | 0.000 | 0.019 | 0.159 |
| HEAVY | 0.010 | 0.000 | 0.000 | 0.000 | 0.000 | 0.001 | 0.032 |
| Total Flow (kg/hr) | 1000 | 4757.9 | 2030.6 | 536.6 | 250.4 | 170.5 | 30.26 |
| Temperature (° C.) | 100 | 50 | 50 | 50 | 50 | 50 | 50 |
| Pressure (mmHg) | 0.1 | 0.1 | 0.1 | 760 | 760 | 760 | 760 |

| Mass Fraction Aspen Alias | Heavies | R-1F | R-2F | R-3F | R-4E | R-5E | R-6D |
|---|---|---|---|---|---|---|---|
| C16 SA-ME | 0.000 | 0.000 | 0.000 | 0.000 | 0.006 | 0.000 | 0.000 |
| C18 SA-ME | 0.000 | 0.005 | 0.000 | 0.000 | 0.029 | 0.000 | 0.000 |
| 18 MHM-ME | 0.001 | 0.907 | 0.689 | 0.966 | 0.957 | 0.163 | 0.001 |
| 18 DHM-ME | 0.128 | 0.066 | 0.218 | 0.031 | 0.007 | 0.450 | 0.128 |

TABLE 5-continued

| | Feed Stream D | | | | | | |
|---|---|---|---|---|---|---|---|
| 18 THM-ME | 0.145 | 0.013 | 0.046 | 0.003 | 0.001 | 0.155 | 0.145 |
| HEAVY | 0.726 | 0.013 | 0.047 | 0.000 | 0.000 | 0.233 | 0.726 |
| Total Flow (kg/hr) | 12.3 | 749.6 | 213.0 | 1494.0 | 4507.4 | 42.5 | 12.3 |
| Temperature (° C.) | 50 | 153.4 | 156.4 | 152.8 | 147.8 | 170.9 | 200.9 |
| Pressure (mmHg) | 760 | 0.1 | 0.1 | 0.1 | 0.1 | 0.1 | 0.1 |

Ex 5

SPE Simulation Using Feedstream D (Variation A)

Figure 5:
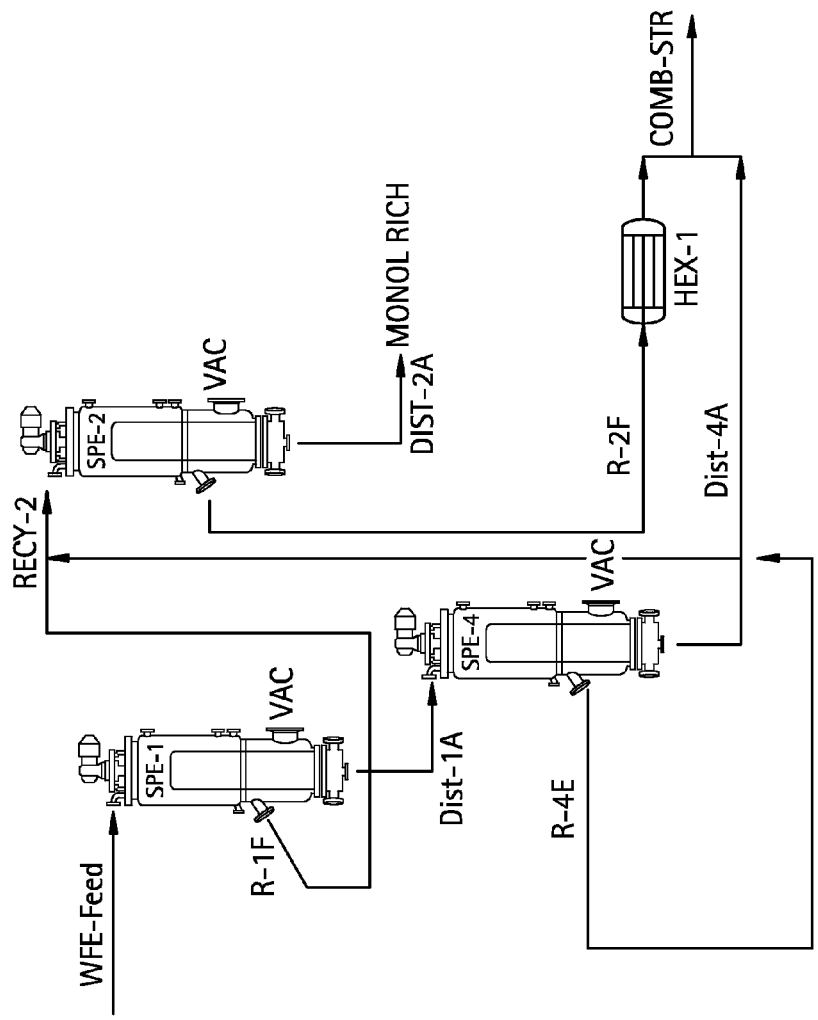
FIG. 5 is a schematic illustration of three connected SPEs in a cascaded mode for continuous operation as used in Ex 5 below.

As schematically illustrated in FIG. 5 below, connect three SPEs, numbered SPE-1, SPE-2 and SPE-4, in a cascaded mode for continuous operation. Table 6 below summarizes Feed Stream composition and effluent Stream results from the SPEs and FIG. 5 depicts connectivity between SPEs as described below. In Table 6, label distillate from each SPE-# as DIST-# or D-# and each SPE's residue stream or effluent stream as R-#, where "#" corresponds in each instance to number of the SPE generated by the SPE as in DIST-1, D-1 and R-1 for SPE-1.

Introduce Feedstream D to SPE-1 and generate residue stream R-1 and distillate stream D-1. Operate SPE-1 with a driving force sufficient to result in a mass D:F ratio of 0.334. Separate material streams so as to feed R-1 to SPE-2, where it combines with R-4, and D-1 to SPE-4. Operate SPE-2 with a driving force sufficient to attain a D:F ratio of 0.864. Recover D-2 to generate a refined monol stream. Operate SPE-4 with a driving force sufficient to result in a D:F ratio of 0.409 and yield D-4, a saturates and monol rich stream.

If desired, combine R-2 and D-4 to yield a combined stream ("COMB-STR") for downstream uses such as generation of a polyol. See Table 6 below for composition of the feedstream ("WFE-FEED"); and each of D-1, D-2, D-4, R-1, R-2, R-4 and COMB-STR.

TABLE 6

| Mass Fraction Aspen Alias | WFE-FEED | DIST-1A | DIST-2A | DIST-4A | R-1F | R-2F | R-4E | COMB-STR |
|---|---|---|---|---|---|---|---|---|
| C16SA-ME | 0.035 | 0.104 | 0.001 | 0.250 | 0.001 | 0.000 | 0.002 | 0.134 |
| C18SA-ME | 0.045 | 0.119 | 0.015 | 0.250 | 0.008 | 0.000 | 0.028 | 0.134 |
| 18MHM-ME | 0.850 | 0.765 | 0.950 | 0.498 | 0.892 | 0.626 | 0.950 | 0.557 |
| 18DHM-ME | 0.050 | 0.011 | 0.031 | 0.002 | 0.069 | 0.226 | 0.018 | 0.105 |
| 18THM-ME | 0.010 | 0.001 | 0.003 | 0.000 | 0.015 | 0.064 | 0.002 | 0.030 |
| HEAVY | 0.010 | 0.000 | 0.000 | 0.000 | 0.015 | 0.084 | 0.000 | 0.039 |
| Total Flow kg/hr | 1000.0 | 333.8 | 745.7 | 136.6 | 666.2 | 117.8 | 197.3 | 254.3 |
| Temperature C. | 100.0 | 50.0 | 50.0 | 50.0 | 152.4 | 157.4 | 149.1 | 101.1 |
| Pressure mmHg | 0.1 | 0.1 | 0.1 | 760.0 | 0.1 | 0.1 | 0.1 | 0.1 |

Ex 6

SPE Simulation Using Feedstream D (Variation B)

Figure 6:
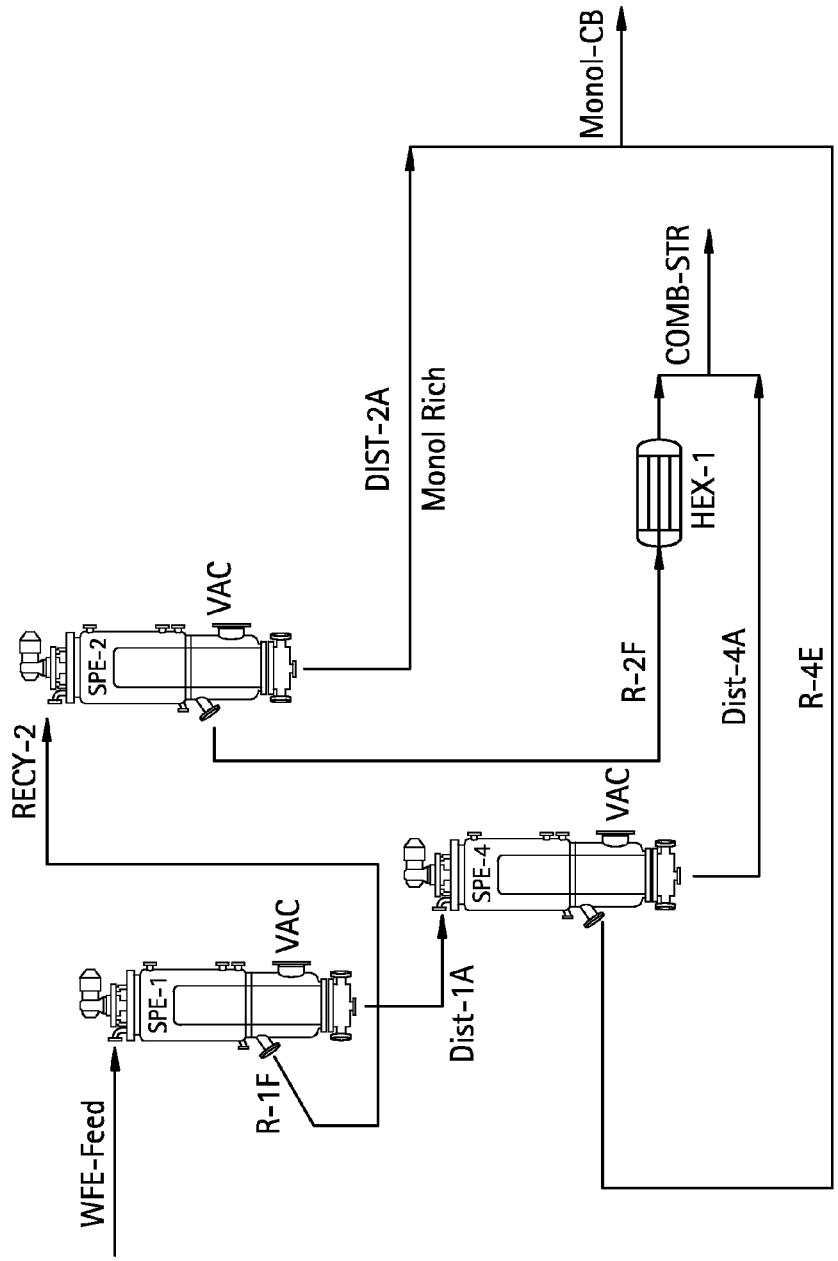
FIG. 6 is a schematic illustration of a variation of three connected SPEs in a cascaded mode for continuous operation as used in Ex 6 below.

Replicate Ex 5 using the same feedstream, but change the D:F ratio for SPE-4 from 0.409 to 0.461 and modify interconnectivity as schematically illustrated in FIG. 6 below. Summarize Feed Stream composition and effluent Stream results from the SPEs as in Ex 5 above in Table 7 below. As an option, combine D-2 and R-4 to form a modified, refined monol stream ("Monol-CB").

TABLE 7

| Mass Fraction Aspen Alias | WFE-FEED | DIST-1A | DIST-2A | DIST-4A | R-1F | R-2F | R-4E | COMB-STR | MONOL-CB |
|---|---|---|---|---|---|---|---|---|---|
| C16SA-ME | 0.035 | 0.104 | 0.001 | 0.223 | 0.001 | 0.000 | 0.001 | 0.140 | 0.001 |
| C18SA-ME | 0.045 | 0.119 | 0.009 | 0.233 | 0.008 | 0.000 | 0.021 | 0.146 | 0.012 |
| 18MHM-ME | 0.850 | 0.765 | 0.947 | 0.541 | 0.892 | 0.553 | 0.957 | 0.546 | 0.949 |
| 18DHM-ME | 0.050 | 0.011 | 0.039 | 0.002 | 0.069 | 0.260 | 0.019 | 0.099 | 0.034 |
| 18THM-ME | 0.010 | 0.001 | 0.004 | 0.000 | 0.015 | 0.078 | 0.002 | 0.029 | 0.004 |
| HEAVY | 0.010 | 0.000 | 0.000 | 0.000 | 0.015 | 0.108 | 0.000 | 0.040 | 0.000 |
| Total Flow kg/hr | 1000.0 | 333.8 | 574.3 | 153.9 | 666.2 | 91.9 | 179.9 | 245.8 | 754.2 |
| Temperature C. | 100.0 | 50.0 | 50.0 | 50.0 | 152.4 | 158.8 | 150.1 | 91.9 | 75.4 |
| Pressure mmHg | 0.1 | 0.1 | 0.1 | 760.0 | 0.1 | 0.1 | 0.1 | 0.1 | 0.1 |

Ex 7

Simulation of Two Packed Distillation Columns and One SPE

Use a packed distillation column to reduce saturate content of a feed stream, thereby yielding a "saturate-depleted feed stream". The packing is a BX packing, such as that supplied by Sulzer Chemtech, with an assumed Height Equivalent to a Theoretical Plate (HETP) of 10 inches (25.4 centimeters (cm)). Use a SPE, either with or without recycle, to effect separation of the saturate-depleted feedstream into a monol-rich stream, a diol-stream and heavies-rich stream.

As a variation, one can also use a SPE to provide a saturate-depleted feed stream and a packed distillation column to separate remaining components of the feed stream into, for example, a monol-rich stream, a diol-rich stream and a heavies-rich stream.

Figure 7:
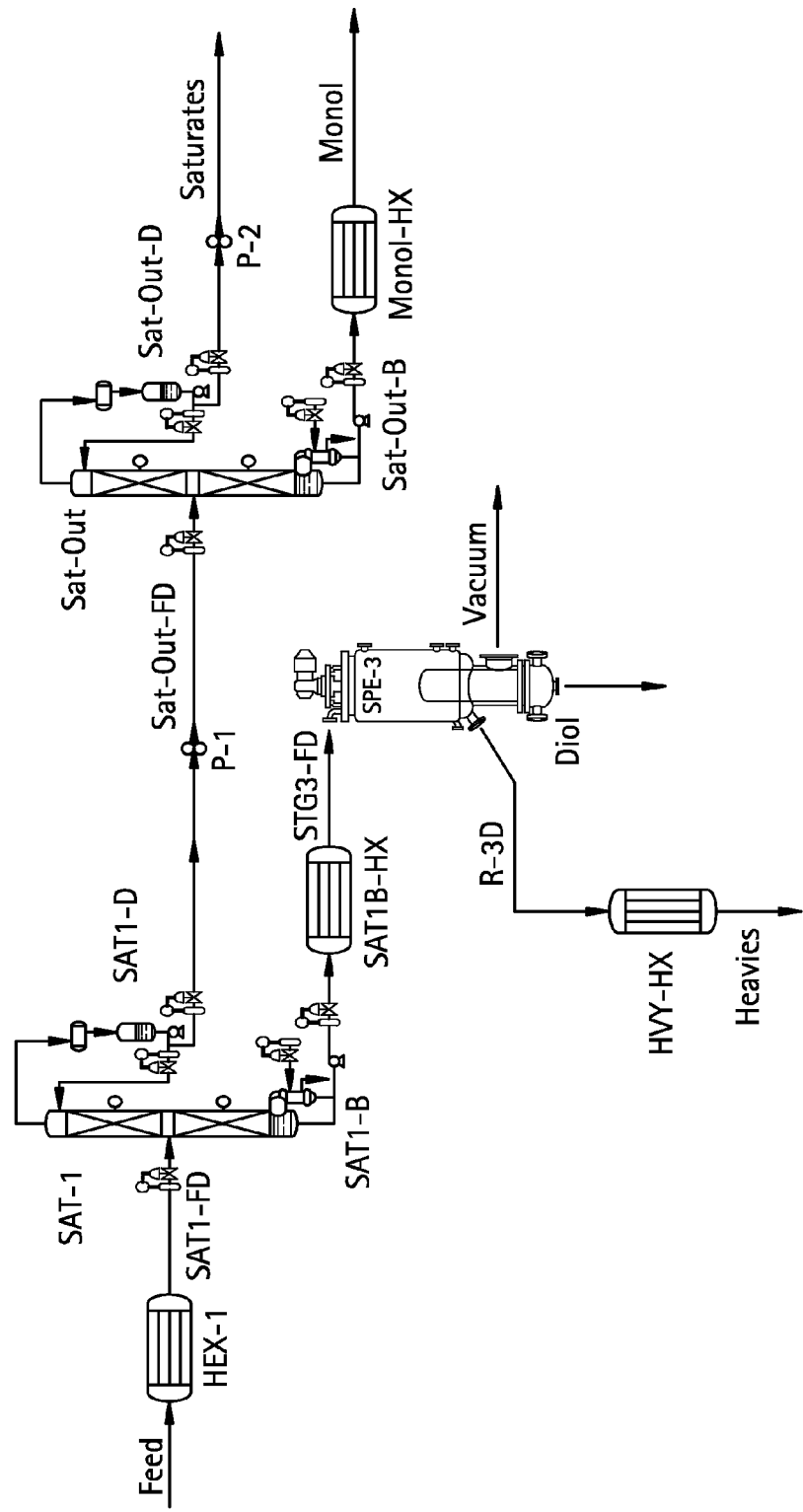
FIG. 7 is a schematic illustration of a combination of two packed distillation columns and one SPE as used in Ex 7 below.

See FIG. 7 below for a schematic illustration of a combination of two packed (Sulzer BX packing with an assumed HETP of 10 inches (25.4 cm)) distillation columns, nominally "SAT-1" and "SAT-OUT", and one SPE. In accord with FIG. 7, preheat Feed Stream A using a heat exchanger (HEX-1), then pass the preheated feed stream to SAT-1, modeled using eight (8) equilibrium stages, which has an overhead (SAT1-D) with a reduced diol content and a bottoms stream (SAT1-B) that has a reduced saturate content and a reduced monol content, each reduction being relative to the preheated feed stream. SAT-1 has the following design specifications (with corresponding Aspen aliases): 0.005 mass fraction monol (18MHM-ME) in SAT1-B and 0.005 mass fraction diol (18DHM-ME) in SAT1-D. Control monol level in SAT1-B by varying D:F ratio (Table 8) to meet SAT1-B design specifications and diol level in SAT1-D by varying reflux ratio of SAT-1 to meet the SAT1-D design specification. In this case, a reflux ratio, 2.78 meets the SAT1-D design specification. SAT-1 has an overhead pressure specification of 0.1 mm Hg. Estimate pressure drop across SAT-1 using hydraulic calculation software based upon the Sulzer BX packing. Skilled artisans recognize that other packing may be used if desired and that a change in packing or characteristics of such packing may vary results presented herein without departing from the spirit or scope of the present invention.

Feed SAT1-D to SAT-OUT, which has the following design specifications (with corresponding Aspen aliases): 0.002 mass fraction based upon a combination of methyl palmitate (C16SA-ME) and methyl stearate (C18SA-ME) in bottoms stream SATOUT-B and 0.005 mass fraction monol (18MHM-ME) in distillate stream SAT-OUT-D. Control saturate level in SATOUT-B by varying D:F ratio (Table 8) and monol level in SAT-OUT-D by varying reflux ratio of SATOUT. In this case, a reflux ratio of 1.82 meets the SAT-OUT-D design specification. SATOUT has the same overhead pressure specification as SAT-1.

Feed SAT1-B to the SPE (nominally SPE-3) and operate the SPE with sufficient thermal driving force and a mass D:F ratio of 0.768 to effect separation of a diol-rich stream from SAT1-B. Table 8 below contains composition information for the feed stream and each of the streams or components that enter or leave one of SAT-1, SAT-OUT and the SPE.

TABLE 8

| Mass Fraction Aspen Alias | FEED | SAT1-FD | SAT1-B | SAT1-D | SAT-OUTFD | SAT-OUT-B | SAT-OUT-D | SATU-RATE | MONOL | STG3-FD | DIOL | R-3D | HEAVIES |
|---|---|---|---|---|---|---|---|---|---|---|---|---|---|
| C16SA-ME | 0.110 | 0.110 | 0.000 | 0.161 | 0.161 | 0.000 | 0.378 | 0.378 | 0.000 | 0.000 | 0.000 | 0.000 | 0.000 |
| C18SA-ME | 0.180 | 0.180 | 0.000 | 0.264 | 0.264 | 0.002 | 0.617 | 0.617 | 0.002 | 0.000 | 0.000 | 0.000 | 0.000 |
| 18MHM-ME | 0.390 | 0.390 | 0.005 | 0.570 | 0.570 | 0.989 | 0.005 | 0.005 | 0.989 | 0.005 | 0.006 | 0.000 | 0.000 |
| 18DHM-ME | 0.280 | 0.280 | 0.869 | 0.005 | 0.005 | 0.009 | 0.000 | 0.000 | 0.009 | 0.869 | 0.953 | 0.592 | 0.592 |
| 18THM-ME | 0.015 | 0.015 | 0.047 | 0.000 | 0.000 | 0.000 | 0.000 | 0.000 | 0.000 | 0.047 | 0.036 | 0.083 | 0.083 |
| HEAVY | 0.025 | 0.025 | 0.079 | 0.000 | 0.000 | 0.000 | 0.000 | 0.000 | 0.000 | 0.079 | 0.004 | 0.325 | 0.325 |
| Total Flow kmol/hr | 3.1 | 3.1 | 0.9 | 2.2 | 2.2 | 1.2 | 1.0 | 1.0 | 1.2 | 0.9 | 0.7 | 0.2 | 0.2 |
| Total Flow kg/hr | 1000.0 | 1000.0 | 318.2 | 681.8 | 681.8 | 391.2 | 290.7 | 290.7 | 391.2 | 318.2 | 244.5 | 73.7 | 73.7 |
| Temperature C. | 100.0 | 150.0 | 234.3 | 40.0 | 40.0 | 198.7 | 50.0 | 50.2 | 50.0 | 150.0 | 50.0 | 183.0 | 50.0 |
| Pressure mmHg | 10.00 | 10.00 | 1.81 | 0.10 | 10.00 | 1.56 | 0.10 | 760.00 | 760.00 | 5.00 | 760.00 | 0.10 | 760.00 |

Ex 8

Replicate Ex 7, but change the feed stream to Feed Stream B In addition, change the design specifications to 0.0055 mass fraction monol (18MHM-ME) in SAT1-B and 0.0055 mass fraction diol (18DHM-ME) in SAT1-D. Also, vary the SAT-1 column reflux ratio, 5.99. For SATOUT, change the design specifications to 0.002 mass fraction for a combination of methyl palmitate and methyl stearate in SATOUT-B and 0.005 mass fraction monol (18MHM-ME) in SAT-OUT-D. Control level of saturates in SAT-OUT-B as in Ex 7 and level of monol in SAT-OUT-D as in Ex 7. In this case, a reflux ratio (sometimes called a "column reflux ratio") of 1.57 meets the SAT-OUT-D design specification. Operate the SPE with sufficient thermal driving force to provide a D:F ratio of 0.881. Table 9 below summarizes composition information as in Ex 7.

TABLE 9

| Mass Fraction Aspen Alias | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| C16SA-ME | 0.050 | 0.050 | 0.104 | 0.000 | 0.104 | 0.333 | 0.000 | 0.333 | 0.000 | 0.000 | 0.000 | 0.000 | 0.000 |
| C18SA-ME | 0.100 | 0.100 | 0.208 | 0.000 | 0.208 | 0.662 | 0.002 | 0.662 | 0.002 | 0.000 | 0.000 | 0.000 | 0.000 |
| 18MHM-ME | 0.330 | 0.330 | 0.682 | 0.006 | 0.682 | 0.005 | 0.990 | 0.005 | 0.990 | 0.006 | 0.006 | 0.000 | 0.000 |
| 18DHM-ME | 0.460 | 0.460 | 0.006 | 0.879 | 0.006 | 0.000 | 0.008 | 0.000 | 0.008 | 0.879 | 0.915 | 0.618 | 0.618 |
| 18THM-ME | 0.050 | 0.050 | 0.000 | 0.096 | 0.000 | 0.000 | 0.000 | 0.000 | 0.000 | 0.096 | 0.078 | 0.230 | 0.230 |
| HEAVY | 0.010 | 0.010 | 0.000 | 0.019 | 0.000 | 0.000 | 0.000 | 0.000 | 0.000 | 0.019 | 0.001 | 0.152 | 0.152 |
| Total Flow kg/hr | 1000.0 | 1000.0 | 479.8 | 520.2 | 479.8 | 150.1 | 329.7 | 150.1 | 329.7 | 520.2 | 458.2 | 62.0 | 62.0 |
| Temperature °C. | 100.0 | 150.0 | 40.0 | 241.5 | 40.0 | 50.0 | 187.2 | 50.2 | 50.0 | 150.0 | 50.0 | 181.5 | 50.0 |
| Pressure mmHg | 10.00 | 10.00 | 0.10 | 2.52 | 10.00 | 0.10 | 0.85 | 760.00 | 760.00 | 5.00 | 760.00 | 0.10 | 760.00 |

Ex 9

Replicate Ex 7, but change the feed stream to Feed Stream C and use the SAT-1B, SAT1-D, SAT-OUT-B and SAT-OUT-D design specifications from Ex 8. In addition, change the design specifications to 0.0055 mass fraction monol (18MHM-ME) in SAT1-B and 0.0055 mass fraction diol (18DHM-ME) in SAT1-D. A SAT-1 column reflux ratio of 1.48 meets the SAT1-B design specifications and a SAT-OUT column reflux ratio of 3.15 meets the SATOUT-D design specification. Operate the SPE with sufficient thermal driving force to provide a D:F ratio of 0.866. See Table 10 below for composition information as in Ex 7. As in Ex 7 and 8, model both distillation columns SAT-1 and SAT-OUT as packed distillation columns with BX packing, a HETP of 10 inches and an overhead pressure of 0.1 mm Hg. Table 10 below summarizes composition information as in Ex 7.

TABLE 10

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.060 | 0.060 | 0.077 | 0.000 | 0.077 | 0.286 | 0.000 | 0.286 | 0.000 | 0.000 | 0.000 | 0.000 | 0.000 |
| C18SA-ME | 0.150 | 0.150 | 0.192 | 0.000 | 0.192 | 0.709 | 0.002 | 0.709 | 0.002 | 0.000 | 0.000 | 0.000 | 0.000 |
| 18MHM-ME | 0.570 | 0.570 | 0.726 | 0.006 | 0.726 | 0.005 | 0.990 | 0.005 | 0.990 | 0.006 | 0.009 | 0.000 | 0.000 |
| 18DHM-ME | 0.150 | 0.150 | 0.006 | 0.672 | 0.006 | 0.000 | 0.008 | 0.000 | 0.008 | 0.672 | 0.815 | 0.480 | 0.480 |
| 18THM-ME | 0.050 | 0.050 | 0.000 | 0.230 | 0.000 | 0.000 | 0.000 | 0.000 | 0.000 | 0.230 | 0.171 | 0.310 | 0.310 |
| HEAVY | 0.020 | 0.020 | 0.000 | 0.092 | 0.000 | 0.000 | 0.000 | 0.000 | 0.000 | 0.092 | 0.004 | 0.210 | 0.210 |
| Total Flow kg/hr | 1000.0 | 1000.0 | 783.1 | 216.9 | 783.1 | 209.9 | 573.2 | 209.9 | 573.2 | 216.9 | 124.0 | 92.8 | 92.8 |
| Temperature °C. | 100.0 | 150.0 | 40.0 | 229.3 | 40.0 | 50.0 | 201.5 | 50.2 | 50.0 | 150.0 | 50.0 | 183.9 | 50.0 |
| Pressure mmHg | 10.00 | 10.00 | 0.10 | 1.28 | 10.00 | 0.10 | 1.80 | 760.00 | 760.00 | 5.00 | 760.00 | 0.10 | 760.00 |

Ex 10

Replicate Ex 9, but change the feed or feed stream to Feed Stream D. In addition, change the SPE D:F ratio to 0.562. Column reflux ratios of 1.84 for SAT-1 and 2.4 for SAT-OUT meet their respective or associated design specifications. Table 11 below summarizes composition information as in Ex 7.

TABLE 11

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.035 | 0.035 | 0.037 | 0.000 | 0.037 | 0.445 | 0.000 | 0.445 | 0.000 | 0.000 | 0.000 | 0.000 | 0.000 |
| C18SA-ME | 0.045 | 0.045 | 0.048 | 0.000 | 0.048 | 0.550 | 0.002 | 0.550 | 0.002 | 0.000 | 0.000 | 0.000 | 0.000 |
| 18MHM-ME | 0.850 | 0.850 | 0.909 | 0.006 | 0.909 | 0.005 | 0.992 | 0.005 | 0.992 | 0.006 | 0.010 | 0.000 | 0.000 |
| 18DHM-ME | 0.050 | 0.050 | 0.006 | 0.688 | 0.006 | 0.000 | 0.006 | 0.000 | 0.006 | 0.688 | 0.864 | 0.461 | 0.461 |
| 18THM-ME | 0.010 | 0.010 | 0.000 | 0.153 | 0.000 | 0.000 | 0.000 | 0.000 | 0.000 | 0.153 | 0.119 | 0.197 | 0.197 |
| HEAVY | 0.010 | 0.010 | 0.000 | 0.153 | 0.000 | 0.000 | 0.000 | 0.000 | 0.000 | 0.153 | 0.008 | 0.341 | 0.341 |
| Total Flow kg/hr | 1000.0 | 1000.0 | 934.8 | 65.2 | 934.8 | 78.7 | 856.1 | 78.7 | 856.1 | 65.2 | 36.7 | 28.5 | 28.5 |
| Temperature °C. | 100.0 | 150.0 | 40.0 | 236.8 | 40.0 | 50.0 | 190.7 | 50.2 | 50.0 | 150.0 | 50.0 | 185.2 | 50.0 |
| Pressure mmHg | 10.00 | 10.00 | 0.10 | 1.78 | 10.00 | 0.10 | 1.02 | 760.00 | 760.00 | 5.00 | 760.00 | 0.10 | 760.00 |

Skilled artisans understand that one may make any of a number of modifications of the separations provided in Ex 7-10 depending upon desired composition of one or more streams. For example, one may use the first packed column, SAT-1, to effect removal of at least a substantial portion of saturated contained in the feed stream and operate SAT-1 such that SAT1-B contains a higher fraction of monol relative to total SAT1-B composition than the fraction of monol relative to the feed stream. Feeding SAT1-B to SAT-OUT allows monol recovery as SAT-OUT-D and use of the SPE to separate diol as overhead (SAT-OUT-D or R-3D). In addition, one may also add precursor operations and/or downstream operations depending upon desired handling of, respectively, feedstreams prior to the separation detailed in any of Ex 7-10 or downstream handling of streams exiting one or more of the separation apparatus. Further, one may substitute a third distillation column, preferably a packed distillation column, for the SPE.

Ex 11

Figure 8:
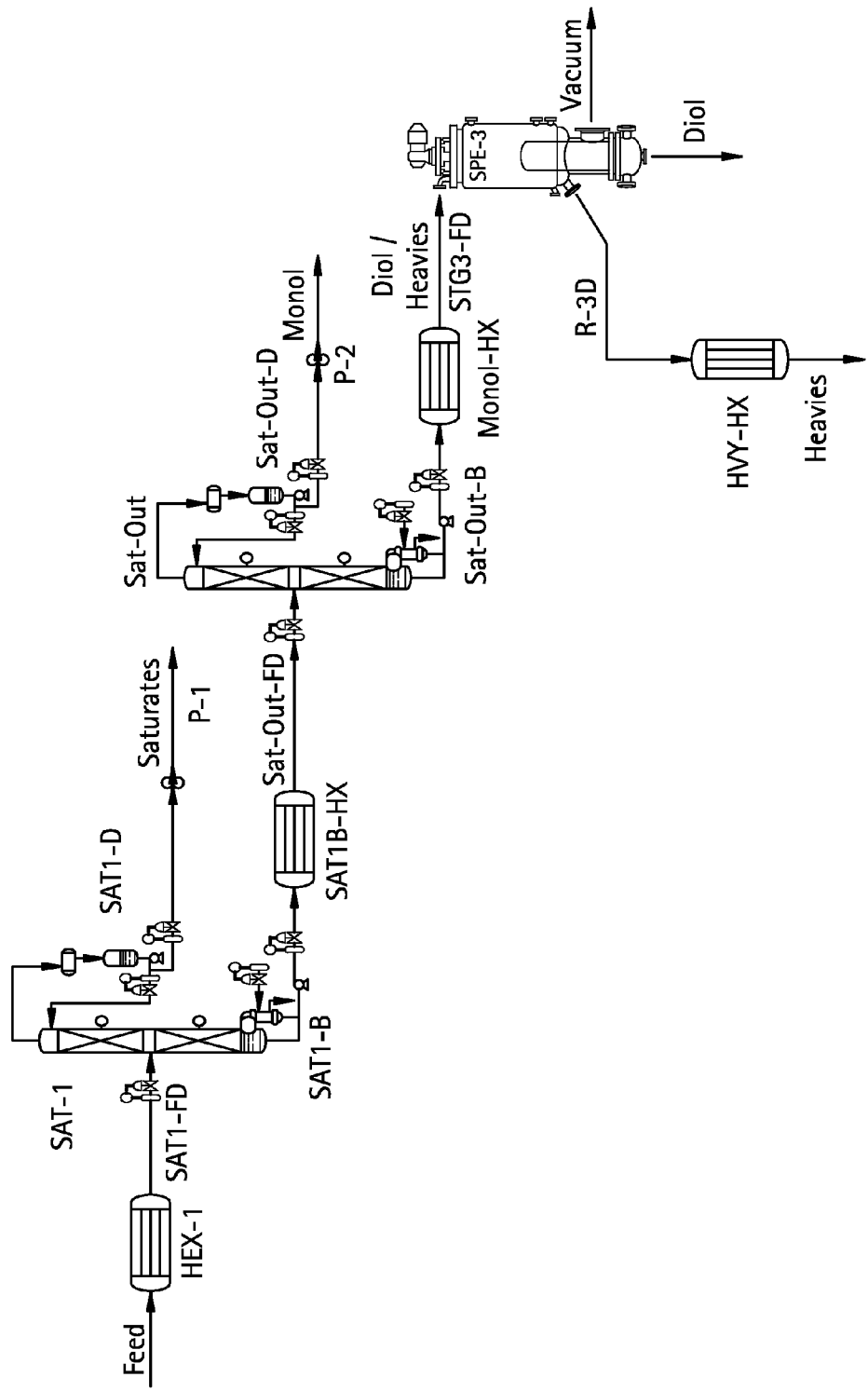
FIG. 8 is a schematic illustration of a combination of two packed distillation columns and one SPE as shown in Ex 11 below.

Using Feed Stream A, but a combination of two packed distillation columns, nominally "SAT-1" and "SAT-OUT", and one SPE as shown in FIG. 8 below rather than that shown in FIG. 7 below, replicate Ex 7 with a number of changes. First, change SAT-1 to the following design specifications (with associated Aspen aliases): 0.0065 mass fraction methyl palmitate (C16SA-ME) and methyl stearate (C18SA-ME) in SAT1-B and 0.0065 mass fraction diol (18MHM-ME) in SAT1-D. Second, a SAT-1 reflux ratio of 0.66 meets associated design specifications. Third, change SAT-OUT design specifications to: 0.007 mass fraction based upon monol (18MHM-ME) in bottoms stream SATOUT-B and 0.0055 mass fraction diol (18DHM-ME) in distillate stream SAT-OUT-D. Fourth, a SAT-OUT column reflux ratio of 6.13 meets associated design specifications. Fifth, feed SAT-OUT-B, rather than SAT1-B, to the SPE (nominally SPE-3) and operate the SPE with the same thermal driving force and mass D:F ratio as in Ex 7 and a mass D:F ratio of 0.768 to effect separation of a diol-rich stream from SAT-OUT-B. Table 12 below contains composition information for the feed stream and each of the streams or components that enter or leave one of SAT-1, SAT-OUT and the SPE. See Table 12 below for composition information as in Ex 7.

TABLE 12

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.110 | 0.110 | 0.383 | 0.000 | 0.000 | 0.000 | 0.000 | 0.383 | 0.000 | 0.000 | 0.000 | 0.000 | 0.000 |
| C18SA-ME | 0.180 | 0.180 | 0.611 | 0.006 | 0.006 | 0.012 | 0.000 | 0.611 | 0.012 | 0.000 | 0.000 | 0.000 | 0.000 |
| 18MHM-ME | 0.390 | 0.390 | 0.007 | 0.545 | 0.545 | 0.983 | 0.007 | 0.007 | 0.983 | 0.007 | 0.009 | 0.000 | 0.000 |
| 18DHM-ME | 0.280 | 0.280 | 0.000 | 0.393 | 0.393 | 0.006 | 0.868 | 0.000 | 0.006 | 0.868 | 0.951 | 0.594 | 0.594 |
| 18THM-ME | 0.015 | 0.015 | 0.000 | 0.021 | 0.021 | 0.000 | 0.047 | 0.000 | 0.000 | 0.047 | 0.036 | 0.083 | 0.083 |
| HEAVY | 0.025 | 0.025 | 0.000 | 0.035 | 0.035 | 0.000 | 0.078 | 0.000 | 0.000 | 0.078 | 0.004 | 0.323 | 0.323 |
| Total Flow kg/hr | 1000.0 | 1000.0 | 287.2 | 712.8 | 712.8 | 392.7 | 320.1 | 287.2 | 392.7 | 320.1 | 245.9 | 74.1 | 74.1 |
| Temperature C. | 100.0 | 150.0 | 40.0 | 191.5 | 150.0 | 50.0 | 237.2 | 40.0 | 50.2 | 50.0 | 50.0 | 182.9 | 50.0 |
| Pressure mmHg | 10.00 | 10.00 | 0.10 | 0.74 | 5.00 | 0.10 | 2.07 | 10.00 | 760.00 | 760.00 | 760.00 | 0.10 | 760.00 |

Ex 12

Replicate Ex 11, but use Feed Stream B and make a number of changes. First, change the SAT1-B design specifications to: 0.0035 mass fraction methyl palmitate (C16SA-ME) and methyl stearate (C18SA-ME). Second, change the SAT1-D design specification to 0.0055 mass fraction diol (18MHM-ME). Third, a SAT-1 column reflux ratio of 1.11 meets associated design specifications. Fourth, a SAT-OUT-D column reflux ratio of 9.35 meets associated design specifications. Fifth, change the SPE D:F ratio to 0.780. See Table below for composition information as in Ex above. See Table 13 below for composition information as in Ex 7 above.

TABLE 13

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.050 | 0.050 | 0.338 | 0.000 | 0.000 | 0.000 | 0.000 | 0.338 | 0.000 | 0.000 | 0.000 | 0.000 | 0.000 |
| C18SA-ME | 0.100 | 0.100 | 0.656 | 0.003 | 0.003 | 0.009 | 0.000 | 0.656 | 0.009 | 0.000 | 0.000 | 0.000 | 0.000 |
| 18MHM-ME | 0.330 | 0.330 | 0.006 | 0.386 | 0.386 | 0.985 | 0.007 | 0.006 | 0.985 | 0.007 | 0.009 | 0.000 | 0.000 |
| 18DHM-ME | 0.460 | 0.460 | 0.000 | 0.540 | 0.540 | 0.006 | 0.878 | 0.000 | 0.006 | 0.878 | 0.921 | 0.724 | 0.724 |
| 18THM-ME | 0.050 | 0.050 | 0.000 | 0.059 | 0.059 | 0.000 | 0.096 | 0.000 | 0.000 | 0.096 | 0.069 | 0.192 | 0.192 |
| HEAVY | 0.010 | 0.010 | 0.000 | 0.012 | 0.012 | 0.000 | 0.019 | 0.000 | 0.000 | 0.019 | 0.001 | 0.084 | 0.084 |
| Total Flow kg/hr | 1000.0 | 1000.0 | 147.8 | 852.2 | 852.2 | 330.3 | 521.8 | 147.8 | 330.3 | 521.8 | 407.1 | 114.7 | 114.7 |
| Temperature C. | 100.0 | 150.0 | 40.0 | 191.0 | 150.0 | 50.0 | 241.3 | 40.0 | 50.2 | 50.0 | 50.0 | 179.8 | 50.0 |
| Pressure mmHg | 10.00 | 10.00 | 0.10 | 0.57 | 5.00 | 0.10 | 2.52 | 10.00 | 760.00 | 760.00 | 760.00 | 0.10 | 760.00 |

Ex 13

Replicate Ex 11 with changes. First, use Feed Stream C rather than Feed Stream A. Second, change the SAT1-B design specifications to 0.005 mass fraction methyl palmitate (C16SA-ME) and methyl stearate (C18SA-ME) and the SAT1-D design specification to 0.005 mass fraction diol (18MHM-ME). Third, a SAT-1 column reflux ratio of 2.07 meets associated design specifications. Fourth, change the SAT-OUT, design specifications to 0.0055 mass fraction based upon monol (18MHM-ME) in bottoms stream SATOUT-B and 0.0055 mass fraction diol (18DHM-ME) in distillate stream SAT-OUT-D. Fifth, a SAT-OUT column reflux ratio of 5.03 meets associated design specifications. Sixth, change the SPE D:F ratio to 0.765. See Table 14 below for composition information.

TABLE 14

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.060 | 0.060 | 0.290 | 0.000 | 0.000 | 0.000 | 0.000 | 0.290 | 0.000 | 0.000 | 0.000 | 0.000 | 0.000 |
| C18SA-ME | 0.150 | 0.150 | 0.705 | 0.005 | 0.005 | 0.007 | 0.000 | 0.705 | 0.007 | 0.000 | 0.000 | 0.000 | 0.000 |
| 18MHM-ME | 0.570 | 0.570 | 0.005 | 0.718 | 0.718 | 0.988 | 0.006 | 0.005 | 0.988 | 0.006 | 0.007 | 0.000 | 0.000 |
| 18DHM-ME | 0.150 | 0.150 | 0.000 | 0.189 | 0.189 | 0.006 | 0.673 | 0.000 | 0.006 | 0.673 | 0.785 | 0.312 | 0.312 |
| 18THM-ME | 0.050 | 0.050 | 0.000 | 0.063 | 0.063 | 0.000 | 0.229 | 0.000 | 0.000 | 0.229 | 0.201 | 0.322 | 0.322 |
| HEAVY | 0.020 | 0.020 | 0.000 | 0.025 | 0.025 | 0.000 | 0.092 | 0.000 | 0.000 | 0.092 | 0.007 | 0.366 | 0.366 |
| Total Flow kg/hr | 1000.0 | 1000.0 | 207.1 | 792.9 | 792.9 | 574.9 | 218.0 | 207.1 | 574.9 | 218.0 | 166.7 | 51.3 | 51.3 |
| Temperature C. | 100.0 | 150.0 | 40.0 | 204.9 | 150.0 | 50.0 | 243.9 | 40.0 | 50.2 | 50.0 | 50.0 | 188.5 | 50.0 |
| Pressure mmHg | 10.00 | 10.00 | 0.10 | 1.74 | 5.00 | 0.10 | 2.44 | 10.00 | 760.00 | 760.00 | 760.00 | 0.10 | 760.00 |

Ex 14

Replicate Ex 11 with changes. First, use the same feed stream (HF sunflower oil alcohol monomer) as in Ex 10. Second, change the SAT1-D design specifications to 0.0055 mass fraction methyl palmitate (C16SA-ME) and methyl stearate (C18SA-ME) in SAT1-B and 0.0055 mass fraction diol (18MHM-ME). Third, a SAT-1 column reflux ratio of 4.90 meets associated design specifications. Fourth, use the same SAT-OUT design specifications as in Ex 13. Fifth, a column reflux ratio of 5.54 meets associated design specifications. Sixth, change the SPE D:F ratio to 0.755. See Table 15 below for composition information.

SAT1-B by varying distillate to feed ratio (D:F) and control monol content in SAT1-D by varying distillation column reflux ratio. Co-feed SAT1-B after it is diluted with an equal mass of solvent (EA-FD) to give the stream SMB-FEED and a solvent stream (ELUENT) that comprises ethyl acetate or another suitable solvent to a simulated moving bed (SMB) that splits SAT1-B into two streams, a raffinate stream that has an enriched monol content and an extract stream that has an enriched diol content, in each case relative to SAT1-B.

Feed the extract stream to a boiling tube evaporator (BTE-EX) to vaporize approximately 95 percent by weight of the extract stream at 350 mmHg, thereby effectively separating a substantial fraction of the solvent from the extract stream as

TABLE 15

| | FEED | SAT1-FD | SAT1-D | SAT1-B | SAT-OUTFD | SAT-OUT-D | SAT-OUT-B | SATU-RATE | MONOL | STG3-FD | DIOL | R-3D | HEAVIES |
|---|---|---|---|---|---|---|---|---|---|---|---|---|---|
| Mass Fraction Aspen Alias | | | | | | | | | | | | | |
| C16SA-ME | 0.035 | 0.035 | 0.464 | 0.000 | 0.000 | 0.000 | 0.000 | 0.464 | 0.000 | 0.000 | 0.000 | 0.000 | 0.000 |
| C18SA-ME | 0.045 | 0.045 | 0.530 | 0.005 | 0.005 | 0.006 | 0.000 | 0.530 | 0.006 | 0.000 | 0.000 | 0.000 | 0.000 |
| 18MHM-ME | 0.850 | 0.850 | 0.006 | 0.919 | 0.919 | 0.989 | 0.006 | 0.006 | 0.989 | 0.006 | 0.007 | 0.000 | 0.000 |
| 18DHM-ME | 0.050 | 0.050 | 0.000 | 0.054 | 0.054 | 0.006 | 0.690 | 0.000 | 0.006 | 0.690 | 0.834 | 0.249 | 0.249 |
| 18THM-ME | 0.010 | 0.010 | 0.000 | 0.011 | 0.011 | 0.000 | 0.152 | 0.000 | 0.000 | 0.152 | 0.143 | 0.180 | 0.180 |
| HEAVY | 0.010 | 0.010 | 0.000 | 0.011 | 0.011 | 0.000 | 0.152 | 0.000 | 0.000 | 0.152 | 0.015 | 0.571 | 0.571 |
| Total Flow kg/hr | 1000.0 | 1000.0 | 75.3 | 924.7 | 924.7 | 859.0 | 65.6 | 75.3 | 859.0 | 65.6 | 49.5 | 16.2 | 16.2 |
| Temperature C. | 100.0 | 150.0 | 40.0 | 197.5 | 150.0 | 50.0 | 255.3 | 40.0 | 50.2 | 50.0 | 50.0 | 193.0 | 50.0 |
| Pressure mmHg | 10.00 | 10.00 | 0.10 | 1.42 | 5.00 | 0.10 | 3.87 | 10.00 | 760.00 | 760.00 | 760.00 | 0.10 | 760.00 |

Ex 15

Simulation of Distillation Followed by SMB—Feed Stream A

Figure 13:
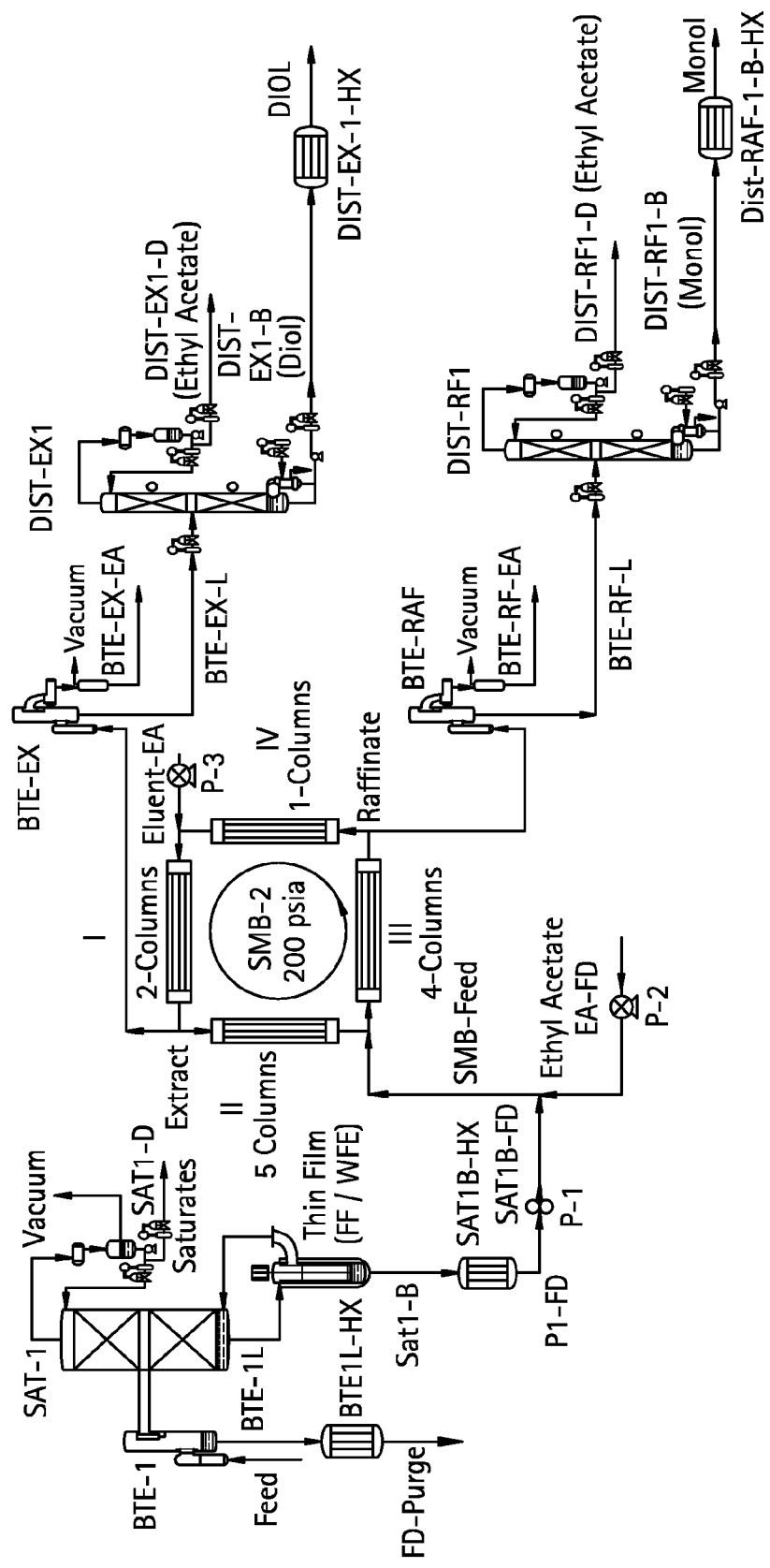
FIG. 13 is a schematic illustration of an ASPEN flow sheet for a method of separating that uses distillation for a first separation operation and SMB for an additional separation as shown in Ex 15 below.

See FIG. 13 below for a schematic illustration of an ASPEN flow sheet for a method of separating that uses distillation for a first separation operation and SMB for an additional separation. As shown in FIG. 13, Feedstream A initially passes through a boiling tube evaporator (BTE-1) that vaporizes about 94% of a feedstream's mass under a reduced pressure or vacuum of one mm Hg to yield a vapor stream designated as BTE1-V. While a reduced pressure of 1 mm Hg is used in this Ex 15, skilled artisans understand that such a high vacuum may be excessive for some purposes and desire to use a lower vacuum such as 5 mm Hg or 10 mm Hg or even lower. Choice of such a lower vacuum does not, however, depart from the spirit or scope of this invention. The balance of the feedstream (approximately 5 percent by weight, based upon total feedstream weight when fed to BTE-1) bears a designation of BTE1-L and remains as a liquid (not vaporized). BTE1-L has an enriched heavies content relative to the feedstream entering BTE-1.

BTE1-V passes through a heat exchanger (HEX-1) and enters a packed distillation tower (SAT-1) to effect separation of BTE1-V into an overhead stream that is rich in at least one saturate (SAT1-D) and a bottoms stream that has a reduced saturate content (SAT1-B), in each case relative to saturate content of the feedstream entering the packed distillation tower. Use eight equilibrium stages with a design specification of 0.0015 mass fraction methyl stearate (C18SA-ME) in bottoms stream SAT1-B and a design specification of 0.01 mass fraction monol (18MHM-ME) in column distillate SAT1-D. Control methyl stearate content in bottoms stream recovered solvent (BTE-EXV1) and leaving an oil product that has the enriched diol content (BTE-EXL1). Feed BTE-EXL1 to a second distillation column (DIST-EX1) to effect further removal of solvent. Simulate operation of DIST-EX1 using five equilibrium stages, a reflux ratio of 5 and a design specification of 0.001 mass fraction of solvent in a bottoms stream exiting DIST-EX1. Tune DIST-EX1 operation to meet the design specification by varying distillate to feed (D:F) ratio. Distillate exiting DIST-EX1 (designated as DIST-EX1D) constitutes recovered process solvent. The bottoms stream exiting DIST-EX1 (designated as DIST-EX1B) constitutes an oil product with an enriched diol content, based upon weight percent of diol in the product relative to weight percent of diol in the soy oil feedstream.

Feed the raffinate stream to a boiling tube evaporator (BTE-RAF) to vaporize approximately 93 percent by weight of the stream at 350 mmHg, thereby effectively separating a substantial fraction of the solvent from the raffinate stream as recovered solvent (BTE-RFV1) and leaving an oil product enriched in monol content (BTE-RFL1). Feed BTE-RFL1 to a third distillation column (DIST-RF1) to effect further removal of solvent. Simulate operation of DIST-RF1 using five equilibrium stages, a reflux ratio of 5 and a design specification of 0.001 mass fraction of solvent in a bottoms stream exiting DIST-RF1. Tune DIST-RF1 operation to meet the design specification by varying distillate to feed (D:F) ratio. Distillate exiting DIST-RF1 (designated as DIST-RF1D) constitutes recovered process solvent. The bottoms stream exiting DIST-RF1 (designated as DIST-RF1B) constitutes an oil product with an enriched monol content, based upon weight percent of monol in the product relative to weight percent of monol in the soy oil feedstream. Table 16 below summarizes composition information for each stream in this Ex 15.

Ex 16 through 18

Replicate Ex 15 three times for Ex 16 (Feed Stream B), Ex 17 (Feed Stream C) and Ex 18 (Feed Stream D) and summarize composition information as for Ex 15 in Tables 17 through 198 below.

TABLE 16

Feedstream A

| Component | BTE-EXL1 | BTE-EXV1 | BTE-RFL1 | BTE-RFV1 | BTE1-L | BTE1-V | BTEEX-EA | BTERF-EA | DIOL |
|---|---|---|---|---|---|---|---|---|---|
| Mass Fraction Aspen Alias | | | | | | | | | |
| H2O | 0.009 | 0.010 | 0.002 | 0.011 | 0.000 | 0.000 | 0.010 | 0.011 | 0.001 |
| C16SA-ME | 0.000 | 0.000 | 0.000 | 0.000 | 0.004 | 0.117 | 0.000 | 0.000 | 0.000 |
| C18SA-ME | 0.000 | 0.000 | 0.002 | 0.000 | 0.016 | 0.190 | 0.000 | 0.000 | 0.000 |
| 18MHM-ME | 0.007 | 0.000 | 0.851 | 0.000 | 0.155 | 0.405 | 0.000 | 0.000 | 0.011 |
| 18DHM-ME | 0.611 | 0.000 | 0.044 | 0.000 | 0.459 | 0.269 | 0.000 | 0.000 | 0.948 |
| 18THM-ME | 0.025 | 0.000 | 0.006 | 0.000 | 0.050 | 0.013 | 0.000 | 0.000 | 0.039 |
| HEAVY | 0.000 | 0.000 | 0.014 | 0.000 | 0.315 | 0.007 | 0.000 | 0.000 | 0.000 |
| ETHYL-01 | 0.348 | 0.990 | 0.081 | 0.989 | 0.000 | 0.000 | 0.990 | 0.989 | 0.001 |
| Total Flow kmol/hr | 2.4 | 45.5 | 1.7 | 22.2 | 0.2 | 2.9 | 45.5 | 22.2 | 0.7 |
| Total Flow kg/hr | 382.4 | 3849.2 | 440.5 | 1873.3 | 59.6 | 940.4 | 3849.2 | 1873.3 | 246.4 |
| Total Flow l/hr | 473.6 | 2788750.0 | 548.3 | 1524070.0 | 74.6 | 86926800.0 | 4431.4 | 2156.4 | 253.5 |
| Temperature C. | 71.1 | 71.1 | 112.9 | 112.9 | 205.5 | 205.5 | 50.0 | 50.0 | 50.0 |
| Pressure mmHg | 350.0 | 350.0 | 350.0 | 350.0 | 1.0 | 1.0 | 350.0 | 350.0 | 760.0 |

| Component | DISTEX1B | DISTEX1D | DISTRF1B | DISTRF1D | EA | EA-FD | ELUENT | ELUENT-F | EXTRACT |
|---|---|---|---|---|---|---|---|---|---|
| Mass Frac Aspen Alias | | | | | | | | | |
| H2O | 0.001 | 0.024 | 0.000 | 0.017 | 0.011 | 0.011 | 0.011 | 0.011 | 0.010 |
| C16SA-ME | 0.000 | 0.000 | 0.000 | 0.000 | 0.000 | 0.000 | 0.000 | 0.000 | 0.000 |
| C18SA-ME | 0.000 | 0.000 | 0.002 | 0.000 | 0.000 | 0.000 | 0.000 | 0.000 | 0.000 |
| 18MHM-ME | 0.011 | 0.000 | 0.927 | 0.000 | 0.000 | 0.000 | 0.000 | 0.000 | 0.001 |
| 18DHM-ME | 0.948 | 0.000 | 0.047 | 0.000 | 0.000 | 0.000 | 0.000 | 0.000 | 0.055 |
| 18THM-ME | 0.039 | 0.000 | 0.006 | 0.000 | 0.000 | 0.000 | 0.000 | 0.000 | 0.002 |
| HEAVY | 0.000 | 0.000 | 0.015 | 0.000 | 0.000 | 0.000 | 0.000 | 0.000 | 0.000 |
| ETHYL-01 | 0.001 | 0.976 | 0.001 | 0.983 | 0.989 | 0.989 | 0.989 | 0.989 | 0.932 |
| Total Flow kmol/hr | 0.7 | 1.7 | 1.2 | 0.4 | 7.7 | 7.7 | 62.1 | 62.1 | 47.9 |
| Total Flow kg/hr | 246.4 | 136.0 | 404.5 | 36.1 | 649.7 | 649.7 | 5246.0 | 5246.0 | 4231.6 |
| Total Flow l/hr | 272.9 | 148.5 | 508.9 | 39.4 | 722.4 | 724.8 | 5832.9 | 5849.3 | 4796.8 |
| Temperature C. | 151.4 | 14.1 | 185.5 | 13.7 | 25.0 | 27.4 | 25.0 | 27.1 | 29.6 |
| Pressure mmHg | 55.0 | 50.0 | 55.0 | 50.0 | 750.1 | 10343.0 | 760.0 | 10343.0 | 10343.0 |

| Component | FD-PURGE | FEED | MONOL | P1-FD | P5-EA | P6-EA | P7-EA | P8-EA | RAFFINAT |
|---|---|---|---|---|---|---|---|---|---|
| Mass Fraction Aspen Alias | | | | | | | | | |
| H2O | 0.000 | 0.000 | 0.000 | 0.000 | 0.010 | 0.011 | 0.024 | 0.017 | 0.009 |
| C16SA-ME | 0.004 | 0.110 | 0.000 | 0.000 | 0.000 | 0.000 | 0.000 | 0.000 | 0.000 |
| C18SA-ME | 0.016 | 0.180 | 0.002 | 0.002 | 0.000 | 0.000 | 0.000 | 0.000 | 0.000 |
| 18MHM-ME | 0.155 | 0.390 | 0.927 | 0.582 | 0.000 | 0.000 | 0.000 | 0.000 | 0.162 |
| 18DHM-ME | 0.459 | 0.280 | 0.047 | 0.389 | 0.000 | 0.000 | 0.000 | 0.000 | 0.008 |
| 18THM-ME | 0.050 | 0.015 | 0.006 | 0.018 | 0.000 | 0.000 | 0.000 | 0.000 | 0.001 |
| HEAVY | 0.315 | 0.025 | 0.015 | 0.010 | 0.000 | 0.000 | 0.000 | 0.000 | 0.003 |
| ETHYL-01 | 0.000 | 0.000 | 0.001 | 0.000 | 0.990 | 0.989 | 0.976 | 0.983 | 0.816 |
| Total Flow kmol/hr | 0.2 | 3.1 | 1.2 | 1.9 | 45.5 | 22.2 | 1.7 | 0.4 | 23.8 |
| Total Flow kg/hr | 59.6 | 1000.0 | 404.5 | 649.7 | 3849.2 | 1873.3 | 136.0 | 36.1 | 2313.8 |
| Total Flow l/hr | 65.8 | 1152.4 | 451.9 | 701.8 | 4432.1 | 2156.7 | 148.6 | 39.4 | 2696.2 |
| Temperature C. | 50.0 | 100.0 | 50.0 | 50.0 | 50.1 | 50.1 | 14.3 | 13.8 | 29.6 |
| Pressure mmHg | 760.0 | 760.0 | 760.0 | 3.4 | 760.0 | 760.0 | 760.0 | 760.0 | 10343.0 |

| Component | SAT-FD | SAT1-B | SAT1-D | SAT1B-FD | SATURATE | SMB-FEED |
|---|---|---|---|---|---|---|
| Mass Fraction Aspen Alias | | | | | | |
| H2O | 0.000 | 0.000 | 0.000 | 0.000 | 0.000 | 0.006 |
| C16SA-ME | 0.117 | 0.000 | 0.377 | 0.000 | 0.377 | 0.000 |
| C18SA-ME | 0.190 | 0.002 | 0.612 | 0.002 | 0.612 | 0.001 |
| 18MHM-ME | 0.405 | 0.582 | 0.010 | 0.582 | 0.010 | 0.291 |
| 18DHM-ME | 0.269 | 0.389 | 0.000 | 0.389 | 0.000 | 0.194 |
| 18THM-ME | 0.013 | 0.018 | 0.000 | 0.018 | 0.000 | 0.009 |
| HEAVY | 0.007 | 0.010 | 0.000 | 0.010 | 0.000 | 0.005 |
| ETHYL-01 | 0.000 | 0.000 | 0.000 | 0.000 | 0.000 | 0.494 |
| Total Flow kmol/hr | 2.9 | 1.9 | 1.0 | 1.9 | 1.0 | 9.6 |
| Total Flow kg/hr | 940.4 | 649.7 | 290.7 | 649.7 | 290.7 | 1299.5 |
| Total Flow l/hr | 1211.3 | 813.8 | 335.2 | 703.1 | 335.2 | 1590.5 |

TABLE 16-continued

| Feedstream A | | | | | | |
|---|---|---|---|---|---|---|
| Temperature C. | 216.9 | 222.3 | 40.0 | 52.6 | 40.2 | 39.8 |
| Pressure mmHg | 10.0 | 3.4 | 1.0 | 10343.0 | 760.0 | 10343.0 |

TABLE 17

| Feedstream B | | | | | | | | |
|---|---|---|---|---|---|---|---|---|
| Component | BTE-EXL1 | BTE-EXV1 | BTE-RFL1 | BTE-RFV1 | BTE1-L | BTE1-V | BTEEX-EA | BTERF-EA | DIOL |

| Component | BTE-EXL1 | BTE-EXV1 | BTE-RFL1 | BTE-RFV1 | BTE1-L | BTE1-V | BTEEX-EA | BTERF-EA | DIOL |
|---|---|---|---|---|---|---|---|---|---|
| Mass Fraction Aspen Alias | | | | | | | | | |
| H2O | 0.006 | 0.011 | 0.004 | 0.011 | 0.000 | 0.000 | 0.011 | 0.011 | 0.001 |
| C16SA-ME | 0.000 | 0.000 | 0.000 | 0.000 | 0.002 | 0.053 | 0.000 | 0.000 | 0.000 |
| C18SA-ME | 0.000 | 0.000 | 0.003 | 0.000 | 0.008 | 0.105 | 0.000 | 0.000 | 0.000 |
| 18MHM-ME | 0.004 | 0.000 | 0.728 | 0.000 | 0.107 | 0.343 | 0.000 | 0.000 | 0.006 |
| 18DHM-ME | 0.690 | 0.000 | 0.074 | 0.000 | 0.621 | 0.451 | 0.000 | 0.000 | 0.915 |
| 18THM-ME | 0.059 | 0.000 | 0.020 | 0.000 | 0.142 | 0.045 | 0.000 | 0.000 | 0.078 |
| HEAVY | 0.000 | 0.000 | 0.008 | 0.000 | 0.122 | 0.004 | 0.000 | 0.000 | 0.000 |
| ETHYL-01 | 0.240 | 0.989 | 0.164 | 0.989 | 0.000 | 0.000 | 0.989 | 0.989 | 0.001 |
| Total Flow kmol/hr | 2.9 | 56.0 | 2.0 | 26.8 | 0.1 | 2.8 | 56.0 | 26.8 | 1.2 |
| Total Flow kg/hr | 570.0 | 4738.2 | 439.7 | 2264.0 | 54.9 | 945.1 | 4738.2 | 2264.0 | 430.3 |
| Total Flow l/hr | 697.1 | 3516631.5 | 551.9 | 1732797.8 | 65.3 | 84838646.9 | 5454.6 | 2606.3 | 441.0 |
| Temperature C. | 79.3 | 79.3 | 90.3 | 90.3 | 211.4 | 211.4 | 50.0 | 50.0 | 50.0 |
| Pressure mmHg | 350.0 | 350.0 | 350.0 | 350.0 | 1.0 | 1.0 | 350.0 | 350.0 | 760.0 |

| Component | DISTEX1B | DISTEX1D | DISTRF1B | DISTRF1D | EA | EA-FD | ELUENT | ELUENT-F | EXTRACT |
|---|---|---|---|---|---|---|---|---|---|
| Mass Fraction Aspen Alias | | | | | | | | | |
| H2O | 0.001 | 0.022 | 0.001 | 0.021 | 0.011 | 0.011 | 0.011 | 0.011 | 0.010 |
| C16SA-ME | 0.000 | 0.000 | 0.000 | 0.000 | 0.000 | 0.000 | 0.000 | 0.000 | 0.000 |
| C18SA-ME | 0.000 | 0.000 | 0.003 | 0.000 | 0.000 | 0.000 | 0.000 | 0.000 | 0.000 |
| 18MHM-ME | 0.006 | 0.000 | 0.874 | 0.000 | 0.000 | 0.000 | 0.000 | 0.000 | 0.000 |
| 18DHM-ME | 0.915 | 0.000 | 0.088 | 0.000 | 0.000 | 0.000 | 0.000 | 0.000 | 0.074 |
| 18THM-ME | 0.078 | 0.000 | 0.024 | 0.000 | 0.000 | 0.000 | 0.000 | 0.000 | 0.006 |
| HEAVY | 0.000 | 0.000 | 0.009 | 0.000 | 0.000 | 0.000 | 0.000 | 0.000 | 0.000 |
| ETHYL-01 | 0.001 | 0.978 | 0.001 | 0.979 | 0.989 | 0.989 | 0.989 | 0.989 | 0.909 |
| Total Flow kmol/hr | 1.2 | 1.7 | 1.1 | 0.9 | 9.4 | 9.4 | 76.0 | 76.0 | 58.9 |
| Total Flow kg/hr | 430.3 | 139.6 | 366.6 | 73.1 | 795.3 | 795.3 | 6421.2 | 6421.2 | 5308.1 |
| Total Flow l/hr | 475.4 | 152.5 | 451.2 | 79.9 | 884.3 | 887.1 | 7139.6 | 7158.0 | 6043.7 |
| Temperature C. | 153.6 | 14.0 | 170.7 | 13.9 | 25.0 | 27.4 | 25.0 | 26.9 | 29.4 |
| Pressure mmHg | 55.0 | 50.0 | 55.0 | 50.0 | 750.1 | 10343.0 | 760.0 | 10343.0 | 10343.0 |

| Component | FD-PURGE | FEED | MONOL | P1-FD | P5-EA | P6-EA | P7-EA | P8-EA | RAFFINAT |
|---|---|---|---|---|---|---|---|---|---|
| Mass Fraction Aspen Alias | | | | | | | | | |
| H2O | 0.000 | 0.000 | 0.001 | 0.000 | 0.011 | 0.011 | 0.022 | 0.021 | 0.010 |
| C16SA-ME | 0.002 | 0.050 | 0.000 | 0.000 | 0.000 | 0.000 | 0.000 | 0.000 | 0.000 |
| C18SA-ME | 0.008 | 0.100 | 0.003 | 0.002 | 0.000 | 0.000 | 0.000 | 0.000 | 0.000 |
| 18MHM-ME | 0.107 | 0.330 | 0.874 | 0.406 | 0.000 | 0.000 | 0.000 | 0.000 | 0.118 |
| 18DHM-ME | 0.621 | 0.460 | 0.088 | 0.536 | 0.000 | 0.000 | 0.000 | 0.000 | 0.012 |
| 18THM-ME | 0.142 | 0.050 | 0.024 | 0.053 | 0.000 | 0.000 | 0.000 | 0.000 | 0.003 |
| HEAVY | 0.122 | 0.010 | 0.009 | 0.004 | 0.000 | 0.000 | 0.000 | 0.000 | 0.001 |
| ETHYL-01 | 0.000 | 0.000 | 0.001 | 0.000 | 0.989 | 0.989 | 0.978 | 0.979 | 0.855 |
| Total Flow kmol/hr | 0.1 | 3.0 | 1.1 | 2.3 | 56.0 | 26.8 | 1.7 | 0.9 | 28.8 |
| Total Flow kg/hr | 54.9 | 1000.0 | 366.6 | 795.3 | 4738.2 | 2264.0 | 139.6 | 73.1 | 2703.7 |
| Total Flow l/hr | 57.5 | 1117.6 | 407.1 | 842.4 | 5455.3 | 2606.7 | 152.6 | 79.9 | 3122.6 |
| Temperature C. | 50.0 | 100.0 | 50.0 | 50.0 | 50.1 | 50.1 | 14.2 | 14.1 | 29.4 |
| Pressure mmHg | 760.0 | 760.0 | 760.0 | 2.4 | 760.0 | 760.0 | 760.0 | 760.0 | 10343.0 |

| Component | SAT-FD | SAT1-B | SAT1-D | SAT1B-FD | SATURATE | SMB-FEED |
|---|---|---|---|---|---|---|
| Mass Fraction Aspen Alias | | | | | | |
| H2O | 0.000 | 0.000 | 0.000 | 0.000 | 0.000 | 0.006 |
| C16SA-ME | 0.053 | 0.000 | 0.333 | 0.000 | 0.333 | 0.000 |

TABLE 17-continued

| | | | Feedstream B | | | |
|---|---|---|---|---|---|---|
| C18SA-ME | 0.105 | 0.002 | 0.657 | 0.002 | 0.657 | 0.001 |
| 18MHM-ME | 0.343 | 0.406 | 0.010 | 0.406 | 0.010 | 0.203 |
| 18DHM-ME | 0.451 | 0.536 | 0.000 | 0.536 | 0.000 | 0.268 |
| 18THM-ME | 0.045 | 0.053 | 0.000 | 0.053 | 0.000 | 0.027 |
| HEAVY | 0.004 | 0.004 | 0.000 | 0.004 | 0.000 | 0.002 |
| ETHYL-01 | 0.000 | 0.000 | 0.000 | 0.000 | 0.000 | 0.494 |
| Total Flow kmol/hr | 2.8 | 2.3 | 0.5 | 2.3 | 0.5 | 11.7 |
| Total Flow kg/hr | 945.1 | 795.3 | 149.8 | 795.3 | 149.8 | 1590.6 |
| Total Flow l/hr | 1190.1 | 969.9 | 173.1 | 844.0 | 173.1 | 1938.9 |
| Temperature C. | 230.1 | 219.8 | 40.0 | 52.6 | 40.2 | 39.7 |
| Pressure mmHg | 10.0 | 2.4 | 1.0 | 10343.0 | 760.0 | 10343.0 |

TABLE 18

| | | | | Feedstream C | | | | | |
|---|---|---|---|---|---|---|---|---|---|
| Component | BTE-EXL1 | BTE-EXV1 | BTE-RFL1 | BTE-RFV1 | BTE1-L | BTE1-V | BTEEX-EA | BTERF-EA | DIOL |
| Mass Fraction Aspen Alias | | | | | | | | | |
| H2O | 0.014 | 0.010 | 0.000 | 0.011 | 0.000 | 0.000 | 0.010 | 0.011 | 0.001 |
| C16SA-ME | 0.000 | 0.000 | 0.000 | 0.000 | 0.003 | 0.064 | 0.000 | 0.000 | 0.000 |
| C18SA-ME | 0.000 | 0.000 | 0.000 | 0.000 | 0.015 | 0.158 | 0.000 | 0.000 | 0.000 |
| 18MHM-ME | 0.012 | 0.000 | 0.931 | 0.001 | 0.255 | 0.590 | 0.000 | 0.001 | 0.025 |
| 18DHM-ME | 0.374 | 0.000 | 0.018 | 0.000 | 0.275 | 0.142 | 0.000 | 0.000 | 0.778 |
| 18THM-ME | 0.094 | 0.000 | 0.015 | 0.000 | 0.186 | 0.042 | 0.000 | 0.000 | 0.195 |
| HEAVY | 0.000 | 0.000 | 0.008 | 0.000 | 0.267 | 0.005 | 0.000 | 0.000 | 0.000 |
| ETHYL-01 | 0.507 | 0.990 | 0.027 | 0.988 | 0.000 | 0.000 | 0.990 | 0.988 | 0.001 |
| Total Flow kmol/hr | 2.6 | 49.1 | 1.8 | 24.4 | 0.2 | 2.9 | 49.1 | 24.4 | 0.5 |
| Total Flow kg/hr | 330.6 | 4160.2 | 560.3 | 2063.1 | 58.4 | 941.6 | 4160.2 | 2063.1 | 159.0 |
| Total Flow l/hr | 407.2 | 2952892.8 | 701.9 | 1875091.4 | 72.2 | 85996822.4 | 4789.6 | 2375.6 | 161.8 |
| Temperature C. | 64.2 | 64.2 | 158.3 | 158.3 | 203.4 | 203.4 | 50.0 | 50.0 | 50.0 |
| Pressure mmHg | 350.0 | 350.0 | 350.0 | 350.0 | 1.0 | 1.0 | 350.0 | 350.0 | 760.0 |

| Component | DISTEX1B | DISTEX1D | DISTRF1B | DISTRF1D | EA | EA-FD | ELUENT | ELUENT-F | EXTRACT |
|---|---|---|---|---|---|---|---|---|---|
| Mass Fraction Aspen Alias | | | | | | | | | |
| H2O | 0.001 | 0.025 | 0.000 | 0.012 | 0.011 | 0.011 | 0.011 | 0.011 | 0.011 |
| C16SA-ME | 0.000 | 0.000 | 0.000 | 0.000 | 0.000 | 0.000 | 0.000 | 0.000 | 0.000 |
| C18SA-ME | 0.000 | 0.000 | 0.000 | 0.000 | 0.000 | 0.000 | 0.000 | 0.000 | 0.000 |
| 18MHM-ME | 0.025 | 0.000 | 0.957 | 0.000 | 0.000 | 0.000 | 0.000 | 0.000 | 0.001 |
| 18DHM-ME | 0.778 | 0.000 | 0.019 | 0.000 | 0.000 | 0.000 | 0.000 | 0.000 | 0.028 |
| 18THM-ME | 0.195 | 0.000 | 0.015 | 0.000 | 0.000 | 0.000 | 0.000 | 0.000 | 0.007 |
| HEAVY | 0.000 | 0.000 | 0.008 | 0.000 | 0.000 | 0.000 | 0.000 | 0.000 | 0.000 |
| ETHYL-01 | 0.001 | 0.975 | 0.001 | 0.988 | 0.989 | 0.989 | 0.989 | 0.989 | 0.954 |
| Total Flow kmol/hr | 0.5 | 2.1 | 1.7 | 0.2 | 8.4 | 8.4 | 67.5 | 67.5 | 51.7 |
| Total Flow kg/hr | 159.0 | 171.5 | 545.2 | 15.0 | 706.2 | 706.2 | 5701.8 | 5701.8 | 4490.8 |
| Total Flow l/hr | 173.7 | 187.3 | 703.2 | 16.4 | 785.2 | 787.7 | 6339.7 | 6356.9 | 5063.6 |
| Temperature C. | 149.4 | 14.1 | 209.9 | 13.3 | 25.0 | 27.4 | 25.0 | 27.0 | 29.6 |
| Pressure mmHg | 55.0 | 50.0 | 55.0 | 50.0 | 750.1 | 10343.0 | 760.0 | 10343.0 | 10343.0 |

| Component | FD-PURGE | FEED | MONOL | P1-FD | P5-EA | P6-EA | P7-EA | P8-EA | RAFFINAT |
|---|---|---|---|---|---|---|---|---|---|
| Mass Fraction Aspen Alias | | | | | | | | | |
| H2O | 0.000 | 0.000 | 0.000 | 0.000 | 0.010 | 0.011 | 0.025 | 0.012 | 0.009 |
| C16SA-ME | 0.003 | 0.060 | 0.000 | 0.000 | 0.000 | 0.000 | 0.000 | 0.000 | 0.000 |
| C18SA-ME | 0.015 | 0.150 | 0.000 | 0.000 | 0.000 | 0.000 | 0.000 | 0.000 | 0.000 |
| 18MHM-ME | 0.255 | 0.570 | 0.957 | 0.748 | 0.000 | 0.001 | 0.000 | 0.000 | 0.200 |
| 18DHM-ME | 0.275 | 0.150 | 0.019 | 0.190 | 0.000 | 0.000 | 0.000 | 0.000 | 0.004 |
| 18THM-ME | 0.186 | 0.050 | 0.015 | 0.055 | 0.000 | 0.000 | 0.000 | 0.000 | 0.003 |
| HEAVY | 0.267 | 0.020 | 0.008 | 0.006 | 0.000 | 0.000 | 0.000 | 0.000 | 0.002 |
| ETHYL-01 | 0.000 | 0.000 | 0.001 | 0.000 | 0.990 | 0.988 | 0.975 | 0.988 | 0.783 |
| Total Flow kmol/hr | 0.2 | 3.0 | 1.7 | 2.1 | 49.1 | 24.4 | 2.1 | 0.2 | 26.2 |

TABLE 18-continued

Feedstream C

| | | | | | | | | | |
|---|---|---|---|---|---|---|---|---|---|
| Total Flow kg/hr | 58.4 | 1000.0 | 545.2 | 706.2 | 4160.2 | 2063.1 | 171.5 | 15.0 | 2623.4 |
| Total Flow l/hr | 63.8 | 1154.7 | 608.6 | 770.8 | 4790.3 | 2375.9 | 187.3 | 16.4 | 3075.9 |
| Temperature C. | 50.0 | 100.0 | 50.0 | 50.0 | 50.1 | 50.1 | 14.3 | 13.5 | 29.6 |
| Pressure mmHg | 760.0 | 760.0 | 760.0 | 3.1 | 760.0 | 760.0 | 760.0 | 760.0 | 10343.0 |

| Component | SAT-FD | SAT1-B | SAT1-D | SAT1B-FD | SATURATE | SMB-FEED |
|---|---|---|---|---|---|---|
| Mass Fraction Aspen Alias | | | | | | |
| H2O | 0.000 | 0.000 | 0.000 | 0.000 | 0.000 | 0.006 |
| C16SA-ME | 0.064 | 0.000 | 0.254 | 0.000 | 0.254 | 0.000 |
| C18SA-ME | 0.158 | 0.000 | 0.632 | 0.000 | 0.632 | 0.000 |
| 18MHM-ME | 0.590 | 0.748 | 0.113 | 0.748 | 0.113 | 0.374 |
| 18DHM-ME | 0.142 | 0.190 | 0.000 | 0.190 | 0.000 | 0.095 |
| 18THM-ME | 0.042 | 0.055 | 0.000 | 0.055 | 0.000 | 0.028 |
| HEAVY | 0.005 | 0.006 | 0.000 | 0.006 | 0.000 | 0.003 |
| ETHYL-01 | 0.000 | 0.000 | 0.000 | 0.000 | 0.000 | 0.494 |
| Total Flow kmol/hr | 2.9 | 2.1 | 0.8 | 2.1 | 0.8 | 10.5 |
| Total Flow kg/hr | 941.6 | 706.2 | 235.4 | 706.2 | 235.4 | 1412.4 |
| Total Flow l/hr | 1224.0 | 892.1 | 271.4 | 772.3 | 271.4 | 1730.9 |
| Temperature C. | 223.0 | 216.8 | 40.0 | 52.6 | 40.2 | 39.8 |
| Pressure mmHg | 10.0 | 3.1 | 1.0 | 10343.0 | 760.0 | 10343.0 |

TABLE 19

Feedstream D

| Component | BTE-EXL1 | BTE-EXV1 | BTE-RFL1 | BTE-RFV1 | BTE1-L | BTE1-V | BTEEX-EA | BTERF-EA | DIOL |
|---|---|---|---|---|---|---|---|---|---|
| Mass Fraction Aspen Alias | | | | | | | | | |
| H2O | 0.020 | 0.010 | 0.000 | 0.011 | 0.000 | 0.000 | 0.010 | 0.011 | 0.002 |
| C16SA-ME | 0.000 | 0.000 | 0.000 | 0.000 | 0.002 | 0.037 | 0.000 | 0.000 | 0.000 |
| C18SA-ME | 0.000 | 0.000 | 0.000 | 0.000 | 0.007 | 0.047 | 0.000 | 0.000 | 0.000 |
| 18MHM-ME | 0.020 | 0.000 | 0.980 | 0.032 | 0.626 | 0.863 | 0.000 | 0.032 | 0.099 |
| 18DHM-ME | 0.158 | 0.000 | 0.005 | 0.000 | 0.146 | 0.044 | 0.000 | 0.000 | 0.787 |
| 18THM-ME | 0.022 | 0.000 | 0.002 | 0.000 | 0.056 | 0.007 | 0.000 | 0.000 | 0.111 |
| HEAVY | 0.000 | 0.000 | 0.002 | 0.000 | 0.162 | 0.001 | 0.000 | 0.000 | 0.000 |
| ETHYL-01 | 0.780 | 0.990 | 0.010 | 0.957 | 0.000 | 0.000 | 0.990 | 0.957 | 0.001 |
| Total Flow kmol/hr | 2.6 | 49.1 | 1.8 | 24.4 | 0.2 | 2.9 | 49.1 | 24.4 | 0.5 |
| Total Flow kg/hr | 330.6 | 4160.2 | 560.3 | 2063.1 | 58.4 | 941.6 | 4160.2 | 2063.1 | 159.0 |
| Total Flow l/hr | 407.2 | 2952892.8 | 701.9 | 1875091.4 | 72.2 | 85996822.4 | 4789.6 | 2375.6 | 161.8 |
| Temperature C. | 64.2 | 64.2 | 158.3 | 158.3 | 203.4 | 203.4 | 50.0 | 50.0 | 50.0 |
| Pressure mmHg | 350.0 | 350.0 | 350.0 | 350.0 | 1.0 | 1.0 | 350.0 | 350.0 | 760.0 |

TABLE 19-continued

| | Feedstream D | | | | | | | | |
|---|---|---|---|---|---|---|---|---|---|
| Component | DISTEX1B | DISTEX1D | DISTRF1B | DISTRF1D | EA | EA-FD | ELUENT | ELUENT-F | EXTRACT |
| Mass Fraction Aspen Alias | | | | | | | | | |
| H2O | 0.002 | 0.024 | 0.000 | 0.002 | 0.011 | 0.011 | 0.011 | 0.011 | 0.011 |
| C16SA-ME | 0.000 | 0.000 | 0.000 | 0.000 | 0.000 | 0.000 | 0.000 | 0.000 | 0.000 |
| C18SA-ME | 0.000 | 0.000 | 0.000 | 0.000 | 0.000 | 0.000 | 0.000 | 0.000 | 0.000 |
| 18MHM-ME | 0.099 | 0.000 | 0.989 | 0.873 | 0.000 | 0.000 | 0.000 | 0.000 | 0.001 |
| 18DHM-ME | 0.787 | 0.000 | 0.006 | 0.000 | 0.000 | 0.000 | 0.000 | 0.000 | 0.009 |
| 18THM-ME | 0.111 | 0.000 | 0.003 | 0.000 | 0.000 | 0.000 | 0.000 | 0.000 | 0.001 |
| HEAVY | 0.000 | 0.000 | 0.002 | 0.000 | 0.000 | 0.000 | 0.000 | 0.000 | 0.000 |
| ETHYL-01 | 0.001 | 0.976 | 0.000 | 0.125 | 0.989 | 0.989 | 0.989 | 0.989 | 0.978 |
| Total Flow kmol/hr | 0.5 | 2.1 | 1.7 | 0.2 | 8.4 | 8.4 | 67.5 | 67.5 | 51.7 |
| Total Flow kg/hr | 159.0 | 171.5 | 545.2 | 15.0 | 706.2 | 706.2 | 5701.8 | 5701.8 | 4490.8 |
| Total Flow l/hr | 173.7 | 187.3 | 703.2 | 16.4 | 785.2 | 787.7 | 6339.7 | 6356.9 | 5063.6 |
| Temperature C. | 149.4 | 14.1 | 209.9 | 13.3 | 25.0 | 27.4 | 25.0 | 27.0 | 29.6 |
| Pressure mmHg | 55.0 | 50.0 | 55.0 | 50.0 | 750.1 | 10343.0 | 760.0 | 10343.0 | 10343.0 |

| Component | FD-PURGE | FEED | MONOL | P1-FD | P5-EA | P6-EA | P7-EA | P8-EA | RAFFINAT |
|---|---|---|---|---|---|---|---|---|---|
| Mass Fraction Aspen Alias | | | | | | | | | |
| H2O | 0.000 | 0.000 | 0.000 | 0.000 | 0.010 | 0.011 | 0.024 | 0.002 | 0.008 |
| C16SA-ME | 0.002 | 0.035 | 0.000 | 0.000 | 0.000 | 0.000 | 0.000 | 0.000 | 0.000 |
| C18SA-ME | 0.007 | 0.045 | 0.000 | 0.000 | 0.000 | 0.000 | 0.000 | 0.000 | 0.000 |
| 18MHM-ME | 0.626 | 0.850 | 0.989 | 0.929 | 0.000 | 0.032 | 0.000 | 0.873 | 0.238 |
| 18DHM-ME | 0.146 | 0.050 | 0.006 | 0.059 | 0.000 | 0.000 | 0.000 | 0.000 | 0.001 |
| 18THM-ME | 0.056 | 0.010 | 0.003 | 0.010 | 0.000 | 0.000 | 0.000 | 0.000 | 0.001 |
| HEAVY | 0.162 | 0.010 | 0.002 | 0.002 | 0.000 | 0.000 | 0.000 | 0.000 | 0.000 |
| ETHYL-01 | 0.000 | 0.000 | 0.000 | 0.000 | 0.990 | 0.957 | 0.976 | 0.125 | 0.751 |
| Total Flow kmol/hr | 0.2 | 3.0 | 1.7 | 2.1 | 49.1 | 24.4 | 2.1 | 0.2 | 26.2 |
| Total Flow kg/hr | 58.4 | 1000.0 | 545.2 | 706.2 | 4160.2 | 2063.1 | 171.5 | 15.0 | 2623.4 |
| Total Flow l/hr | 63.8 | 1154.7 | 608.6 | 770.8 | 4790.3 | 2375.9 | 187.3 | 16.4 | 3075.9 |
| Temperature C. | 50.0 | 100.0 | 50.0 | 50.0 | 50.1 | 50.1 | 14.3 | 13.5 | 29.6 |
| Pressure mmHg | 760.0 | 760.0 | 760.0 | 3.1 | 760.0 | 760.0 | 760.0 | 760.0 | 10343.0 |

TABLE 19-continued

Feedstream D

| Component<br>Mass Fraction Aspen Alias | SAT-FD | SAT1-B | SAT1-D | SAT1B-FD | SATURATE | SMB-FEED |
|---|---|---|---|---|---|---|
| H2O | 0.000 | 0.000 | 0.000 | 0.000 | 0.000 | 0.006 |
| C16SA-ME | 0.037 | 0.000 | 0.148 | 0.000 | 0.148 | 0.000 |
| C18SA-ME | 0.047 | 0.000 | 0.189 | 0.000 | 0.189 | 0.000 |
| 18MHM-ME | 0.863 | 0.929 | 0.664 | 0.929 | 0.664 | 0.465 |
| 18DHM-ME | 0.044 | 0.059 | 0.000 | 0.059 | 0.000 | 0.030 |
| 18THM-ME | 0.007 | 0.010 | 0.000 | 0.010 | 0.000 | 0.005 |
| HEAVY | 0.001 | 0.002 | 0.000 | 0.002 | 0.000 | 0.001 |
| ETHYL-01 | 0.000 | 0.000 | 0.000 | 0.000 | 0.000 | 0.494 |
| Total Flow kmol/hr | 2.9 | 2.1 | 0.8 | 2.1 | 0.8 | 10.5 |
| Total Flow kg/hr | 941.6 | 706.2 | 235.4 | 706.2 | 235.4 | 1412.4 |
| Total Flow l/hr | 1224.0 | 892.1 | 271.4 | 772.3 | 271.4 | 1730.9 |
| Temperature C. | 223.0 | 216.8 | 40.0 | 52.6 | 40.2 | 39.8 |
| Pressure mmHg | 10.0 | 3.1 | 1.0 | 10343.0 | 760.0 | 10343.0 |

Ex 19-21

Experimental SMB Separations

Figure 9:
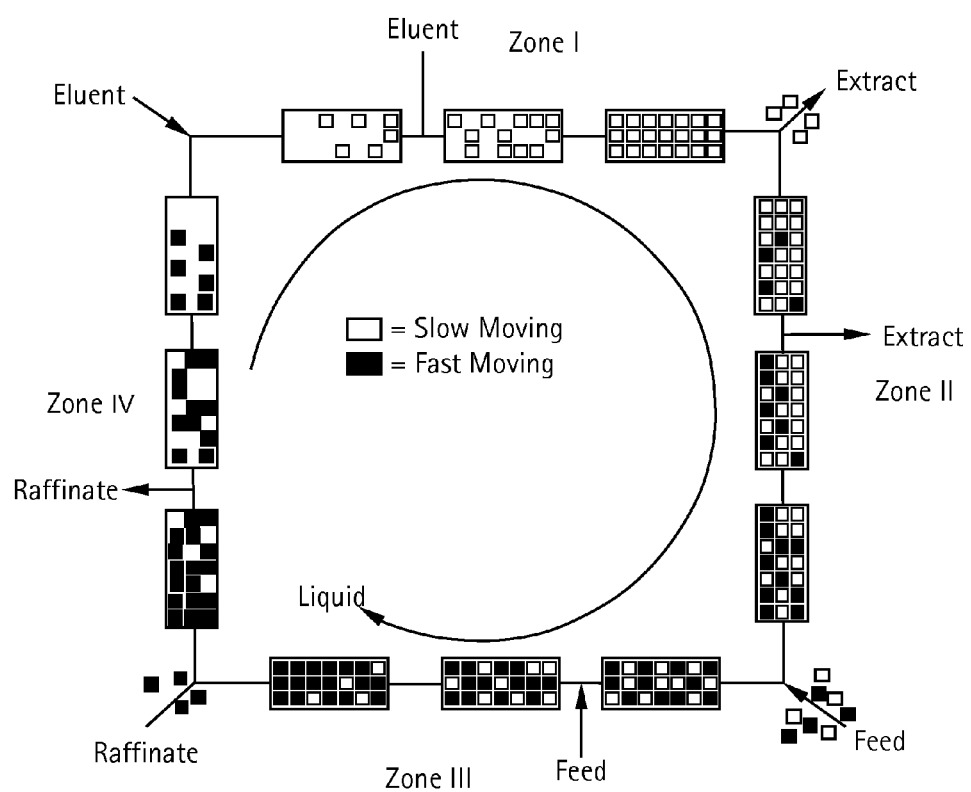
FIG. 9 is schematic illustration of a SMB apparatus operation, showing components that have greater polarity classed as "slow moving" and those that have lesser polarity as "fast moving".

Using a pilot-scale or laboratory scale CSEP® model C912 (Knauer GmbH) carousel-style, multi-column (12 stainless steel tubing columns having an inner diameter (I.D.) of 0.43 inch (1.1 centimeter (cm)) and a length of 36 inches (91.4 cm)) SMB apparatus, ethyl acetate as a solvent and a 70-230 mesh (63-210 um) silica gel as media, effect separations between monol and diol components contained in each of the feedstreams for, respectively, Ex 19 and Ex 20 and effect the separations between saturates and monol for Ex 21. Tables 20, 22 and 24 list SMB operating parameters for, respectively, Ex 19, Ex 20 and Ex 21. Tables 21, 23 and 25 show feed stream composition, raffinate composition and extract composition, each in wt % relative to total weight of, for example, feed stream when providing wt % of feed stream components, respectively for Ex 19, Ex 20 and Ex 21. In Tables 21, 23 and 25, components designated as, for example "FrameC14" refer to a fatty acid methyl ester that contains 14 carbon atoms. Listing other components generically, such as diols, lactones, lactols and heavies provides sufficient information to illustrate effective separation via SMB operation. The feedstream for Ex 19 is an experimental seed oil derivative prepared by methanolysis, hydroformylation and hydrogenation of soybean oil. The feedstream for Ex 20 is an experimental mixture of methanolyzed, hydroformylated and hydrogenated soy bean oil derivatives that has a reduced saturate content. The feedstream for Ex 21 is the raffinate from Ex 19 after modification via rotary evaporation to reduce feedstream ethyl acetate content to 50 wt %, based upon feedstream weight. FIG. 9 below schematically illustrates SMB apparatus operation, showing components that have greater polarity classed as "slow moving" and those that have lesser polarity as "fast moving". For ease of illustration, FIG. 9 also shows a configuration known as a "3-3-3-3" configuration, rather than a "2-5-4-1 configuration" as used in these Ex 19-21. Other configurations may also be used if desired.

TABLE 20

Ex 19 Operating Parameters

| Stream | Flow Rate |
|---|---|
| Eluent Flow | 6.72 mL/min |
| Feed Flow | 1.71 mL/min |
| Extract Flow | 5.41 mL/min |
| Raffinate Flow | 3.03 mL/min |
| Step time | 585 seconds |

TABLE 21

Ex 19 Composition Information

| Component | Feed (wt %) | Raffinate (wt %) | Extract (wt %) |
|---|---|---|---|
| FameC14 | 0.0329 | 0.0188 | 0 |
| FameC15 | 0.0103 | 0.005842 | 0 |
| Palmitate | 4.6996 | 2.6138 | 0.0175 |
| FameC17 | 0.0513 | 0.0292 | 0 |
| FameC18s | 0.0185 | 0.0116 | 0 |
| Stearate | 7.7677 | 4.3953 | 0.001475 |
| Monol_Palmitate | 0.0531 | 0.0307 | 0 |
| FameC20 | 0.188 | 0.1112 | 0.002229 |
| Monoaldehyde | 0.0607 | 0.0413 | 0.004129 |
| Monol_Stearate | 17.6414 | 9.8308 | 0.006566 |
| Cyclic Ether | 0.2949 | 0.3186 | 0 |

TABLE 21-continued

Ex 19 Composition Information

| Component | Feed (wt %) | Raffinate (wt %) | Extract (wt %) |
|---|---|---|---|
| Monol_C20 | 0.101 | 0.0692 | 0.003611 |
| Lactols | 0.1149 | 0.0613 | 0 |
| Diol | 13.8295 | 0.455 | 4.0688 |
| Lactones | 0.2122 | 0.0864 | 0.01 |
| Triols | 0.8488 | 0.0943 | 0.2112 |
| Heavies | 1.4441 | 0.9087 | 0 |
| Total | 47.37 | 19.08 | 4.33 |

TABLE 22

Ex 20 Operating Parameters

| Stream | Flow Rate |
|---|---|
| Eluent Flow | 3.85 mL/min |
| Feed Flow | 0.94 mL/min |
| Extract Flow | 3.09 mL/min |
| Raffinate Flow | 1.7 mL/min |
| Step time | 834 seconds |

TABLE 23

Ex 20 Composition Information

| Component | Feed (wt %) | Raffinate (wt %) | Extract (wt %) | Mass Balance |
|---|---|---|---|---|
| Palmitate | 0.0268 | 0.006419 | 0.004221 | 0.9374 |
| Stearate | 0.1277 | 0.0664 | 0 | 0.9270 |
| Monol_Palmitate | 0.0228 | 0.0121 | 0 | 0.9461 |
| FameC20 | 0.118 | 0.067 | 0 | 1.0123 |
| Monoaldehyde | 0.1706 | 0.0663 | 0.004905 | 0.7860 |
| Monol_Stearate | 28.2556 | 15.7469 | 0.0649 | 1.0010 |
| Cyclic Ether | 1.0396 | 0.4674 | 0.002734 | 0.8101 |
| Monol_C20 | 0.4649 | 0.1492 | 0.0228 | 0.7311 |
| Lactols | 0.8546 | 0.2933 | 0.1128 | 1.0396 |
| Diol | 18.675 | 0.8061 | 5.3951 | 1.0131 |
| Lactones | 0.371 | 0.1395 | 0.0364 | 0.9883 |
| Total | 50.13 | 17.82 | 5.64 | 0.9987 |

TABLE 24

Ex 21 Operating Parameters

| Stream | Flow Rate |
|---|---|
| Eluent Flow | 5.92 mL/min |
| Feed Flow | 0.57 mL/min |
| Extract Flow | 4.31 mL/min |
| Raffinate Flow | 2.14 mL/min |
| Step time | 480 seconds |

TABLE 25

Ex 21 Composition Information

| Component | Feed (wt %) | Raffinate (wt %) | Extract (wt %) | Mass Balance |
|---|---|---|---|---|
| Fame C14 | 0.0489 | 0.0123 | 0 | 0.9444 |
| Fame C15 | 0.021 | 0.0161 | 0.00925 | 6.2090 |
| Palmitate | 6.8451 | 1.7828 | 0.004107 | 0.9824 |
| Fame C 17 | 0.077 | 0.0193 | 0 | 0.9410 |
| Fame C 18s | 0.0168 | 0.001259 | 0 | 0.2814 |
| Stearate | 11.51 | 2.9932 | 0.009779 | 0.9828 |

TABLE 25-continued

Ex 21 Composition Information

| Component | Feed (wt %) | Raffinate (wt %) | Extract (wt %) | Mass Balance |
|---|---|---|---|---|
| Monol_Palmitate | 0.0794 | 0.00268 | 0.0101 | 1.0886 |
| FameC20 | 0.2853 | 0.0629 | 0.005759 | 0.9804 |
| Monoaldehyde | 0.0773 | 0.0248 | 0 | 1.2045 |
| Monol_Stearate | 25.9643 | 0.7578 | 3.1228 | 1.0190 |
| Cyclic Ether | 0.7822 | 0.0727 | 0.003585 | 0.3836 |
| Monol_C20 | 0.1821 | 0.0139 | 0.0132 | 0.8347 |
| Lactols | 0.2205 | 0 | 0.177 | 6.0697 |
| Diol | 1.2183 | 0.0114 | 0.1362 | 0.8805 |
| Lactones | 0.2466 | 0.0349 | 0.0101 | 0.8410 |
| Triols | 0.2504 | 0.0076 | 0.0105 | 0.4310 |
| Heavies | 2.2398 | 0.5752 | 0 | 0.9642 |
| Total | 50.07 | 6.39 | 3.51 | 1.0096 |

Example 22

Simulation of Dual SMB Units—Feedstream A

Figure 10:
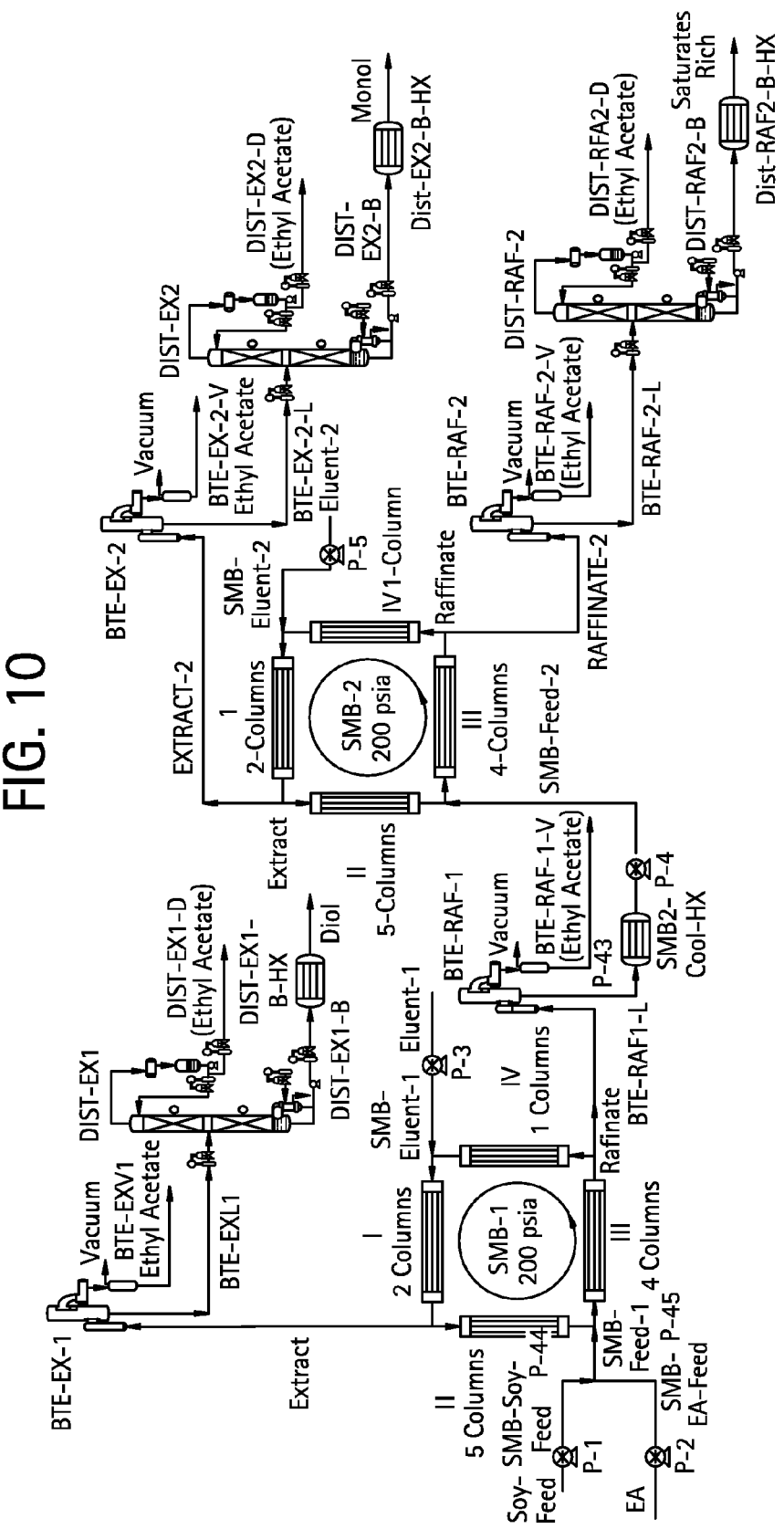
FIG. 10 is a schematic illustration of separation scheme that uses two SMBs to separate a seed oil derivative feed stream as shown in Ex 22 below.

See FIG. 10 below for a schematic illustration of a separation scheme that uses two SMBs to separate a seed oil derivative feed stream. As shown in FIG. 10, mix an experimental seed oil derivative prepared by methanolysis, hydroformylation and hydrogenation of a soybean oil as in Ex 19 (SMB Soy Feed) and an ethyl acetate eluent stream (SMB-EA-FEED) to form a stream (SMB-FEED-1) with a composition such as that shown as Mass Fraction (Mass Frac or Mass Frac Aspen Alias) amounts in Table 22 below in a column labeled "SMB-FEED" as it passes through a first SMB unit (SMB-1) along with an eluent. SMB-1 yields two output streams, a raffinate stream (Raffinate) that has an enriched monol content and an extract (Extract) stream that has an enriched diol content, enriched in each case being relative to SMB-FEED-1. The separation as modeled by SMB-1 is based on experimental results as described in Ex 19 above.

Continuing with FIG. 10, feed the SMB-1 extract stream to a boiling tube evaporator (BTE-EX-1) to vaporize approximately 95 percent by weight (wt %) of the extract stream at 350 mm Hg, thereby effectively separating a substantial fraction of the solvent from the extract stream as recovered solvent (BTE-EXV1) and leaving an oil product that has the enriched, relative to the SMB-1 extract stream fed to BTE-EX1), diol content (BTE-EXL1). Feed BTE-EXL1 to a distillation column (DIST-EX1) to effect further removal of solvent. Simulate operation of DIST-EX1 using five equilibrium stages, a reflux ratio of 10 and a design specification of 0.001 mass fraction of solvent in a bottoms stream exiting DIST-EX1. Tune DIST-EX1 operation to meet the design specification by varying distillate to feed (D:F) ratio. Distillate exiting DIST-EX1 (designated as DIST-EX1D) constitutes recovered process solvent (ethyl acetate). The bottoms stream exiting DIST-EX1 (designated as DIST-EX1B) constitutes an oil product with an enriched diol content, based upon weight percent of diol in the product, relative to weight percent of diol in both the soy oil feed stream and BTE-EXL1.

Feed the raffinate stream from SMB-1 to a boiling tube evaporator (BTE-RAF-1) to vaporize approximately 66 wt % of the raffinate stream at 350 mmHg, thereby effectively separating a substantial fraction of the solvent from the raffinate stream as recovered solvent (BTE-RAF1-V) and leaving an oil product that has the enriched monol content (BTE-RAF-1-L). Control the vaporization in BTE-RAF-1 such that the BTE-RAF-1-L contains approximately 50 wt % solvent (ethyl acetate). Skilled artisans recognize that solvent content in BTE-RAF-1-L may be readily varied to greater or lesser amounts than 50 wt % without departing from the spirit or scope of the present invention.

Cool BTE-RAF-1-L to 25° C. to form SMB-FEED-2. Pass SMB-FEED-2 through a second SMB separation unit (SMB-2). SMB-FEED-2 has a composition such as that shown as Mass Fraction (Mass Frac) amounts in Table 26 below in a column labeled "SMBFEED2". SMB-2 splits SMB-FEED-2 into two streams, a raffinate stream (RAFFINATE-2) that has an enriched saturate content and an extract (EXTRACT-2) stream that has an enriched monol content, enriched in each case relative to SMB-FEED-2. The separation as modeled by SMB-2 is based on experiment results as described in Ex 20 above.

Feed EXTRACT-2 to a BTE (BTE-EX-2) to vaporize approximately 95 wt % of EXTRACT-2 at 250 mm Hg, thereby effectively separating a substantial fraction of the solvent from the extract stream as recovered solvent (BTE-EX-2-V) and leaving an oil product that has the enriched, relative to EXTRACT-2, monol content (BTE-EX-2-L). Feed BTE-EX-2-L to a second distillation column (DIST-EX2) to effect further removal of solvent. Simulate operation of DIST-EX2 using five equilibrium stages, a reflux ratio of 10 and a design specification of 0.001 mass fraction of solvent in a bottoms stream exiting DIST-EX2. Tune DIST-EX2 operation to meet the design specification by varying distillate to feed (D:F) ratio. Distillate exiting DIST-EX2 (designated as DIST-EX2D) constitutes recovered process solvent. The bottoms stream exiting DIST-EX2 (designated as DIST-EX2B) constitutes an oil product with an enriched monol content, based upon weight percent of monol in the product relative to weight percent of monol in the SMB-2 feed stream.

Feed the raffinate stream from SMB-2 to a boiling tube evaporator (BTE-RAF-2) to vaporize approximately 95 wt % of the extract stream at 350 mm Hg, thereby effectively separating a substantial fraction of the solvent from the extract stream as recovered solvent (BTE-RAF-2-V) and leaving an oil product that has the enriched saturate content (BTE-RAF-2-L). Feed BTE-RAF-2-L to a third distillation column (DIST-RAF-2) to effect further removal of solvent. Simulate operation of DIST-RAF-2 using five equilibrium stages, a reflux ratio of 10 and a design specification of 0.001 mass fraction of solvent in a bottoms stream exiting DIST-RAF-2. Tune DIST-RAF-2 operation to meet the design specification by varying distillate to feed (D:F) ratio. Distillate exiting DIST-RAF-2 (designated as DIST-RAF-2D) constitutes recovered process solvent. The bottoms stream exiting DIST-RAF-2 (designated as DIST-RAF2-B) constitutes an oil product with an enriched saturates content, based upon wt % of saturates in the product relative to weight percent of saturates in the SMB-2 feed stream.

Table 26 below summarizes simulation results from this Ex. 22.

TABLE 26

| | SMB-FEED-1 | SMB-ELUENT-1 | EXTRACT | BTE-EXV1 | BTE-EXL1 | DISTEX1D | DISTEX1B |
|---|---|---|---|---|---|---|---|
| Mass Fraction Aspen Alias | | | | | | | |
| C16SA-ME | 0.05 | 0.00 | 0.00 | 0.00 | 0.00 | 0.00 | 0.00 |
| C18SA-ME | 0.09 | 0.00 | 0.00 | 0.00 | 0.00 | 0.00 | 0.00 |
| 18MHM-ME | 0.20 | 0.00 | 0.00 | 0.00 | 0.00 | 0.00 | 0.00 |
| 18-DHM-ME | 0.14 | 0.00 | 0.05 | 0.00 | 0.60 | 0.00 | 0.95 |
| 18-THM-ME | 0.01 | 0.00 | 0.00 | 0.00 | 0.02 | 0.00 | 0.03 |
| HEAVY | 0.01 | 0.00 | 0.00 | 0.00 | 0.00 | 0.00 | 0.00 |
| ETHYL-01 | 0.49 | 0.99 | 0.93 | 0.99 | 0.36 | 0.98 | 0.00 |
| Total Flow kg/hr | 2000 | 6246 | 4921 | 4486 | 435 | 162 | 274 |
| T (° C.) | 27.4 | 27.0 | 27.1 | 70.2 | 70.2 | 14.1 | 144.0 |
| Pressure mmHg | 10343.0 | 10343.0 | 10343.0 | 350.0 | 350.0 | 50.0 | 55.0 |

| | DIOL | RAFFINATE | BTE-RAF1-V | BTE-RAF-1-L | SMBFEED2 | SMB-ELUENT-2 | ETRACT2 | BTE-EX2V | BTE-EX2L |
|---|---|---|---|---|---|---|---|---|---|
| Mass Fraction Aspen Alias | | | | | | | | | |
| C16SA-ME | 0.00 | 0.03 | 0.00 | 0.07 | 0.07 | 0.00 | 0.00 | 0.00 | 0.00 |
| C18SA-ME | 0.00 | 0.05 | 0.00 | 0.12 | 0.12 | 0.00 | 0.00 | 0.00 | 0.00 |
| 18MHM-ME | 0.00 | 0.12 | 0.00 | 0.26 | 0.26 | 0.00 | 0.03 | 0.00 | 0.43 |
| 18-DHM-ME | 0.95 | 0.01 | 0.00 | 0.01 | 0.01 | 0.00 | 0.00 | 0.00 | 0.03 |
| 18-THM-ME | 0.03 | 0.00 | 0.00 | 0.00 | 0.00 | 0.00 | 0.00 | 0.00 | 0.00 |
| HEAVY | 0.00 | 0.00 | 0.00 | 0.01 | 0.01 | 0.00 | 0.00 | 0.00 | 0.00 |
| ETHYL-01 | 0.00 | 0.77 | 0.99 | 0.50 | 0.50 | 0.99 | 0.96 | 0.99 | 0.51 |
| Total Flow kg/hr | 274 | 3325 | 1848 | 1477 | 1477 | 15340 | 11237 | 10434 | 802 |
| T (° C.) | 50.0 | 27.1 | 64.9 | 64.9 | 27.7 | 26.4 | 26.5 | 55.4 | 55.4 |
| P mmHg | 760.0 | 10343.0 | 350.0 | 350.0 | 10343.0 | 10343.0 | 10343.0 | 250.0 | 250.0 |

| | DISTEX2D | DISTEX2B | MONOL | RAFFINATE2 | BTE-RF2V | BTE-RF2L | DISTRF2D | DISTRF2B | SATURATE |
|---|---|---|---|---|---|---|---|---|---|
| Mass Fraction Aspen Alias | | | | | | | | | |
| C16SA-ME | 0.00 | 0.00 | 0.00 | 0.02 | 0.00 | 0.20 | 0.00 | 0.30 | 0.30 |
| C18SA-ME | 0.00 | 0.00 | 0.00 | 0.03 | 0.00 | 0.33 | 0.00 | 0.50 | 0.50 |
| 18MHM-ME | 0.00 | 0.92 | 0.92 | 0.01 | 0.00 | 0.08 | 0.00 | 0.12 | 0.12 |
| 18-DHM-ME | 0.00 | 0.05 | 0.05 | 0.00 | 0.00 | 0.00 | 0.00 | 0.00 | 0.00 |
| 18-THM-ME | 0.00 | 0.00 | 0.00 | 0.00 | 0.00 | 0.00 | 0.00 | 0.00 | 0.00 |
| HEAVY | 0.00 | 0.00 | 0.00 | 0.00 | 0.00 | 0.03 | 0.00 | 0.05 | 0.05 |
| ETHYL-01 | 0.97 | 0.00 | 0.00 | 0.93 | 0.99 | 0.33 | 0.99 | 0.00 | 0.00 |

TABLE 26-continued

| Total Flow kg/hr | 424 | 378 | 378 | 5580 | 5060 | 520 | 170 | 350 | 350 |
|---|---|---|---|---|---|---|---|---|---|
| T (° C.) | 14.3 | 186.2 | 50.0 | 26.5 | 73.3 | 73.3 | 13.0 | 207.9 | 50.0 |
| P mmHg | 50.0 | 55.0 | 760.0 | 10343.0 | 350.0 | 350.0 | 50.0 | 50.0 | 760.0 |

Similar results are expected with different feed streams, especially with feed streams used in Ex 12 (Feedstream B), Ex 13 (Feedstream C) and Ex 14 (Feedstream D), the compositions of which are shown in Table 1 above. Skilled artisans readily understand that results will vary depending upon selection of oil for the feed stream, as shown in Ex 11 through Ex 14 above. Those results will also vary with other seed oils, whether hydroformylated or hydroformylated and hydrogenated as discussed hereinabove, that are chosen for use as a feed stream.

Example 23-26

Simulation of SPE and SMB

Figure 11:
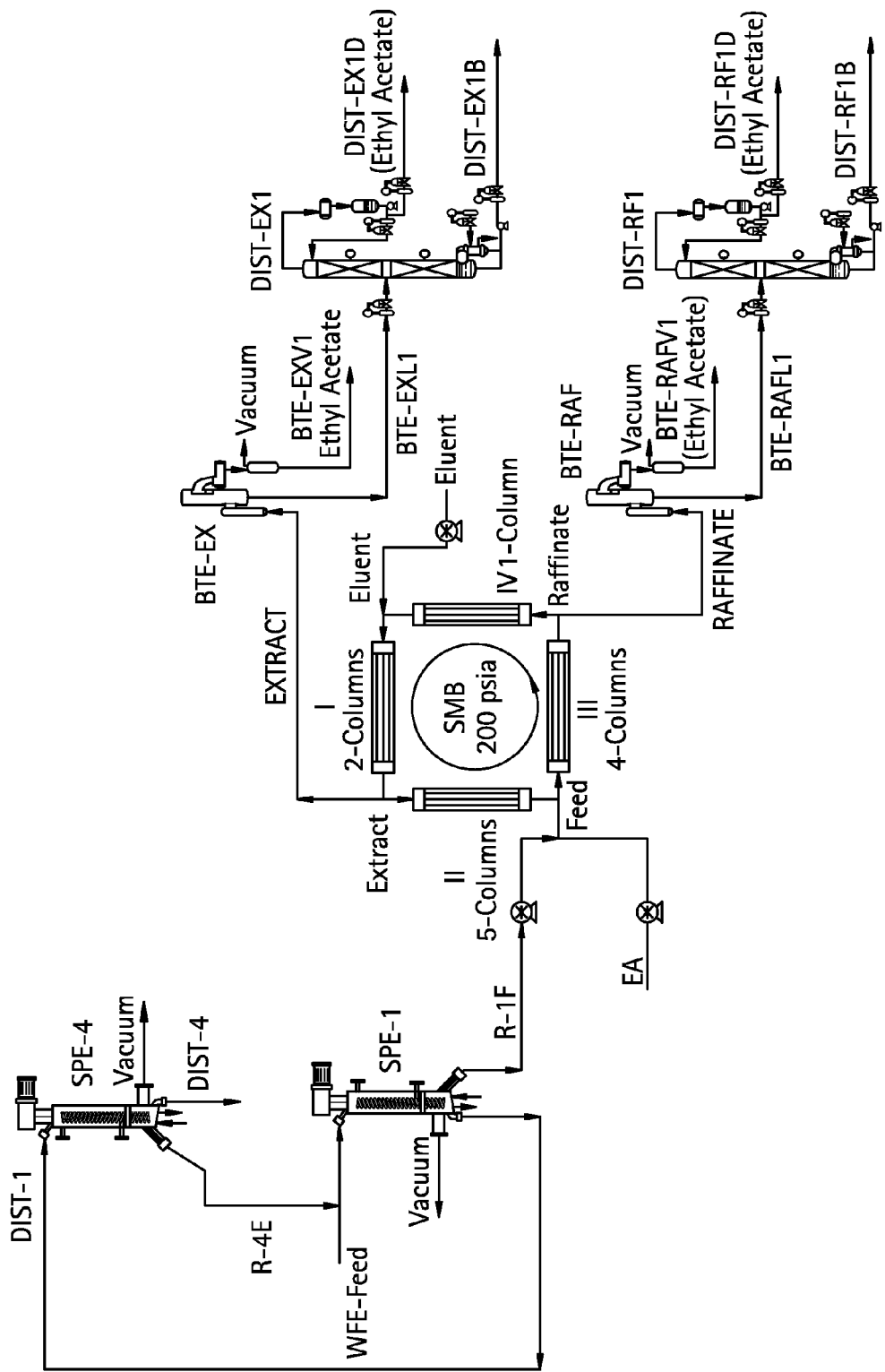
FIG. 11 is a schematic illustration of a separation scheme based upon cascaded SPEs followed by an SMB as shown in Ex 23-Ex 26 below.

FIG. 11 provides a schematic illustration of a separation scheme based upon cascaded SPEs followed by an SMB. The separation scheme so illustrated suitably effects separation of feed streams such as, but not limited to, those shown in Table 1 above. For Ex 23, pass a Feedstream A through a series of flash separation blocks that represent a cascaded group of SPE units and recycle streams. Use the cascaded group of SPE units (Stage-1A through Stage-1F) to remove saturates from the feed stream generating a fraction (R-1F) enriched in monols, diols, triols, and heavies relative to their component levels in Feedstream A. Solvent stream (EA) may, but need not, be combined with R-1F ("combined feed stream").

Co-feed R-1F or, if desired, the combined feed stream with an eluent stream (ELUENT) to an SMB unit (labeled as "SMB" in FIG. 11) that splits co-feed materials into two streams, a raffinate stream that has enriched monol content ("RAFFINATE" in FIG. 11) and an extract stream that has an enriched diol content ("EXTRACT" in FIG. 11), in each case relative to the co-feed. Similar to the way SMB experimental results were used in Ex 22 above, SMB separation modeling has a basis in experiment results as described in Table 23 above.

Use BTE-EX to vaporize and recover SMB process solvent from the extract stream and BTE-RAF to do the same for the raffinate stream. Recover additional process solvent stream from bottoms stream (BTE-EXL1) via packed distillation column DIST-EX1 and from bottoms stream (BTE-RFL1) via packed distillation column DIST-RF1. DIST-EX1 generates two streams, a distillate stream containing recovered process solvent (DISTEX1D) and a bottoms stream (DISTEX1B) containing enriched diol concentrations relative to the SMB feed stream. DIST-RF1 generates two streams, a distillate stream containing recovered process solvent (DISTRF1D) and a bottoms stream (DISTRF1B) containing enriched monol concentrations relative to the SMB feed stream. If desired, an additional SPE may be used to further remove heavies from the DISTRF1B stream.

Similar results are expected with different feed streams, especially with feed streams used in Ex 12 (Feedstream B), Ex 13 (Feedstream C) and Ex 14 (Feedstream D), the compositions of which are shown in Table 1 above. Skilled artisans readily understand that results will vary depending upon selection of oil for the feed stream, as shown in Ex 11 through Ex 14 above. Those results will also vary with other seed oils, whether hydroformylated or hydroformylated and hydrogenated as discussed hereinabove, that are chosen for use as a feed stream.

Example 27-30

Simulation of SMB and Distillation

Figure 12:
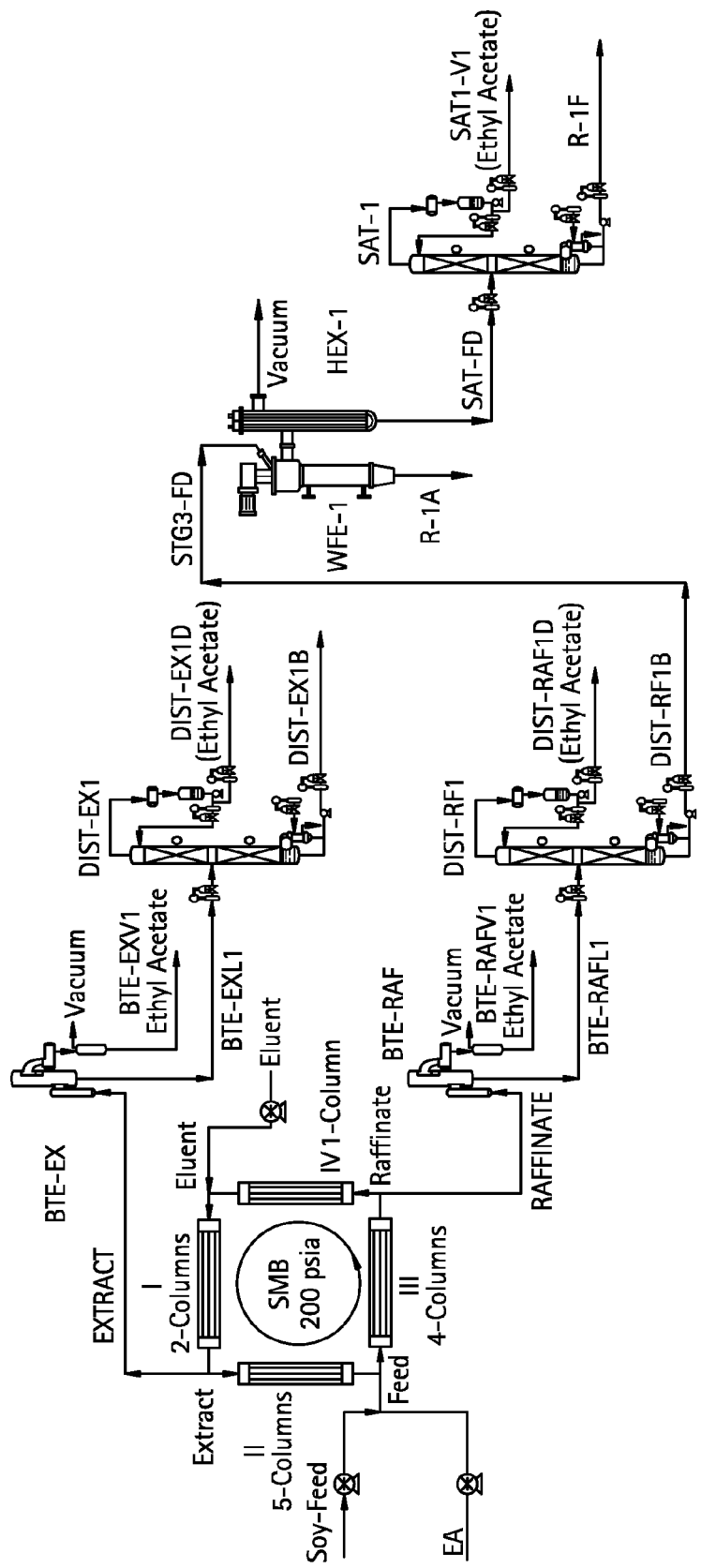
FIG. 12 is a schematic illustration of a SMB followed by parallel distillation of EXTRACT and RAFFINATE exiting the SMB as shown in Ex 27-Ex 30 below.

FIG. 12 below schematically illustrates separation via a SMB followed by parallel distillation of EXTRACT and RAFFINATE exiting the SMB. Mix Feedstream A and a solvent stream (EA) to form a single stream (FEED) with a composition represented by mass fractions (MASS FRAC) in the column labeled "FEED" in Table 27 below. Process FEED through an SMB unit (SMB) along with an eluent (ELUENT) to yield two streams, a raffinate stream (RAFFINATE) that has an enriched monol content and an extract (EXTRACT) stream that has an enriched diol content, in each case relative to the original component ratios in Feedstream A.

Feed EXTRACT stream to a boiling tube evaporator (BTE-EX) to vaporize approximately 95 wt % of the extract stream at 350 mm Hg, thereby effectively separating a substantial fraction of the solvent from EXTRACT as recovered solvent (BTE-EXV1) and leaving an oil product that has the enriched diol content (BTE-EXL1). Feed BTE-EXL1 to a distillation column (DIST-EX1) to effect further removal of solvent. Simulate operation of DIST-EX1 using five equilibrium stages, a reflux ratio of 10 and a design specification of 0.001 percent by weight solvent in a bottoms stream exiting DIST-EX1. Tune DIST-EX1 operation to meet the design specification by varying distillate to feed (D:F) ratio. Distillate exiting DIST-EX1 (designated as DIST-EX1D) constitutes recovered process solvent. The bottoms stream exiting DIST-EX1 (designated as DIST-EX1B) constitutes an oil product with an enriched diol content, based upon weight percent of diol in the product relative to weight percent of diol in the Feedstream A.

Feed RAFFINATE to a boiling tube evaporator (BTE-RAF) to vaporize approximately 90 wt % of the extract stream at 350 mm Hg, thereby effectively separating a substantial fraction of the solvent from the extract stream as recovered solvent (BTE-RFV1) and leaving an oil product that has the enriched diol content (BTE-RFL1). Feed BTE-RFL1 to a second distillation column (DIST-RF1) to effect further removal of solvent. Simulate operation of DIST-RF1 using five equilibrium stages, a reflux ratio of 10 and a design specification of 0.001 percent by weight solvent in a bottoms stream exiting DIST-RF1. Tune DIST-RF1 operation to meet the design specification by varying distillate to feed (D:F) ratio. Distillate exiting DIST-RF1 (designated as DIST-RF1D) constitutes recovered process solvent. The bottoms stream exiting DIST-RF1 (designated as DIST-RF1B) constitutes an oil product with an enriched monol content, based upon weight percent of monol in the product relative to weight percent of monol in the Feedstream A.

Similar results are expected with different feed streams, especially with feed streams used in Ex 12 (Feedstream B), Ex 13 (Feedstream C) and Ex 14 (Feedstream D), the compositions of which are shown in Table 1 above. Skilled artisans readily understand that results will vary depending upon selection of seed oil derivative for use as a feed stream, as shown in Ex 11 through Ex 14 above. Those results will also vary with other seed oil derivatives chosen as feedstreams, but such results do not depart from either the spirit or scope of the present invention.

Figure 14:
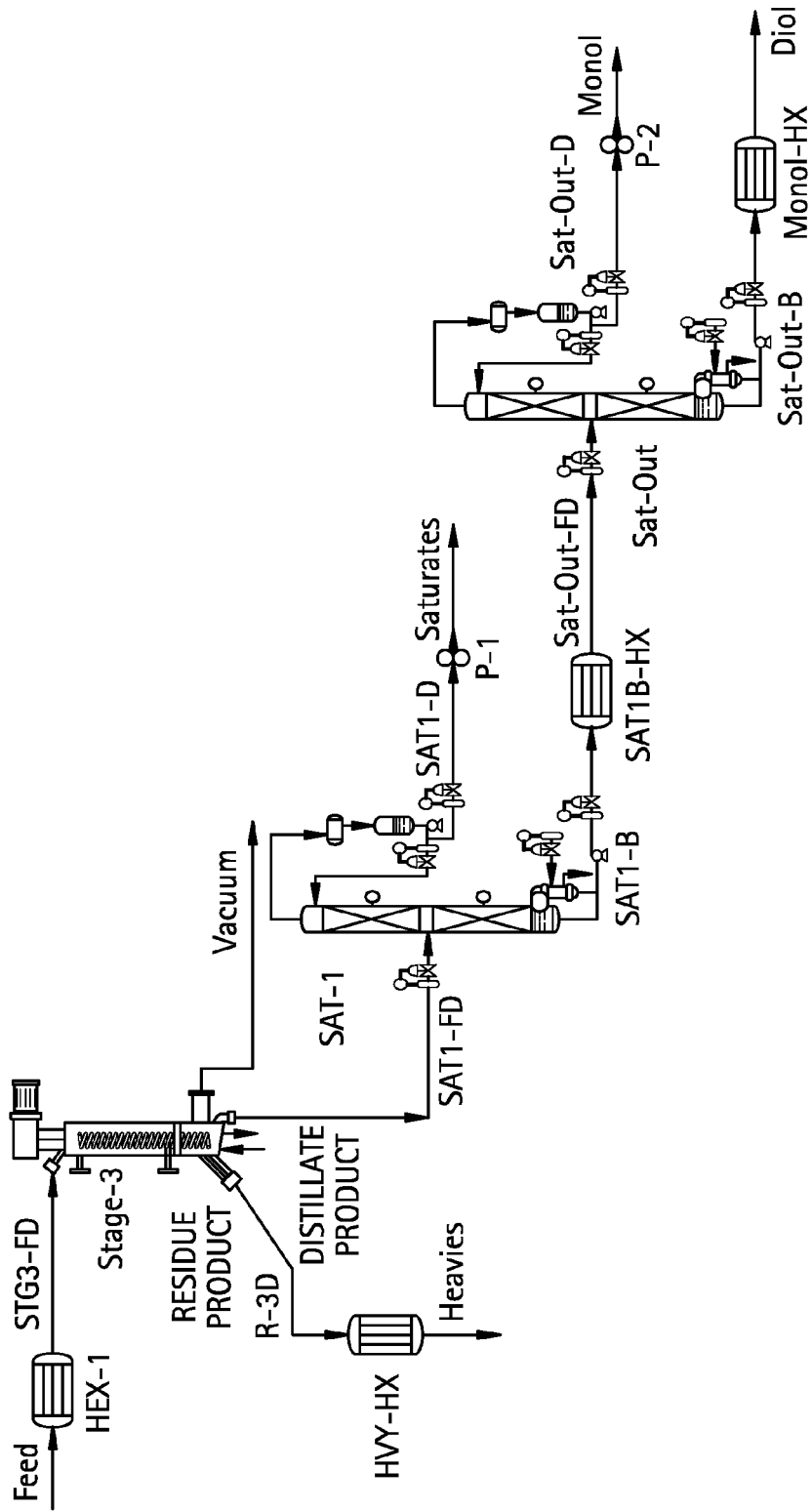
FIG. 14 is a schematic illustration of a SPE to provide a saturate-reduced residue stream (Heavies) with distillate being fed to multiple packed distillation columns as shown in Ex 31 below.

As shown in FIG. 14, preheat Feedstream A (provided by a source not shown in FIG. 14) using heat exchanger (HEX-1) as in Ex 7 above, then pass the preheated feed stream to the SPE (nominally SPE-3), modeled using a series of four cascaded Aspen Plus flash blocks with a residue stream from one

TABLE 27

SMB followed by Distillation Feedstream A

| Component | BTE-EXL1 | BTE-EXV1 | BTE-RFL1 | BTE-RFV1 | D-1A | DIST-2 | DISTEX1B | DISTEX1D | DISTRF1B |
|---|---|---|---|---|---|---|---|---|---|
| Mass Fraction Aspen Alias | | | | | | | | | |
| H2O | 0.010 | 0.010 | 0.002 | 0.011 | 0.000 | 0.000 | 0.002 | 0.023 | 0.000 |
| C16SA-ME | 0.001 | 0.000 | 0.125 | 0.000 | 0.153 | 0.368 | 0.001 | 0.000 | 0.144 |
| C18SA-ME | 0.001 | 0.000 | 0.209 | 0.000 | 0.253 | 0.597 | 0.001 | 0.000 | 0.241 |
| 18MHM-ME | 0.001 | 0.000 | 0.465 | 0.000 | 0.540 | 0.004 | 0.002 | 0.000 | 0.536 |
| 18DHM-ME | 0.599 | 0.000 | 0.025 | 0.000 | 0.025 | 0.000 | 0.953 | 0.000 | 0.029 |
| 18THM-ME | 0.021 | 0.000 | 0.003 | 0.000 | 0.002 | 0.000 | 0.034 | 0.000 | 0.003 |
| HEAVY | 0.000 | 0.000 | 0.019 | 0.000 | 0.002 | 0.000 | 0.000 | 0.000 | 0.022 |
| ETHYL-01 | 0.363 | 0.990 | 0.132 | 0.989 | 0.001 | 0.001 | 0.001 | 0.977 | 0.001 |
| Total Flow kg/hr | 435.1 | 4485.8 | 838.8 | 2486.3 | 684.1 | 284.3 | 273.5 | 161.5 | 727.7 |
| Temperature C. | 70.2 | 70.2 | 97.3 | 97.3 | 189.5 | 40.0 | 144.0 | 14.1 | 209.5 |
| Pressure mmHg | 350.0 | 350.0 | 350.0 | 350.0 | 1.0 | 0.5 | 55.0 | 50.0 | 55.0 |

| Component | DISTRF1D | EA | ELUENT | EXTRACT | FEED | R-1A | R-1F |
|---|---|---|---|---|---|---|---|
| Mass Fraction Aspen Alias | | | | | | | |
| H2O | 0.011 | 0.011 | 0.011 | 0.010 | 0.006 | 0.000 | 0.000 |
| C16SA-ME | 0.000 | 0.000 | 0.000 | 0.000 | 0.053 | 0.011 | 0.000 |
| C18SA-ME | 0.000 | 0.000 | 0.000 | 0.000 | 0.088 | 0.043 | 0.009 |
| 18MHM-ME | 0.000 | 0.000 | 0.000 | 0.000 | 0.196 | 0.473 | 0.923 |
| 18DHM-ME | 0.000 | 0.000 | 0.000 | 0.053 | 0.141 | 0.098 | 0.042 |
| 18THM-ME | 0.000 | 0.000 | 0.000 | 0.002 | 0.006 | 0.021 | 0.004 |
| HEAVY | 0.000 | 0.000 | 0.000 | 0.000 | 0.008 | 0.342 | 0.004 |
| ETHYL-01 | 0.989 | 0.989 | 0.989 | 0.934 | 0.494 | 0.000 | 0.000 |
| Total Flow kg/hr | 111.1 | 1000.0 | 6246.0 | 4920.9 | 2000.0 | 43.6 | 399.4 |
| Temperature C. | 13.3 | 25.0 | 25.0 | 25.0 | 25.0 | 189.5 | 215.1 |
| Pressure mmHg | 50.0 | 750.1 | 760.0 | 750.1 | 750.1 | 1.0 | 3.5 |

| Component | RAFFINAT | SAT-FD | SAT1-V1 | SOY-FEED |
|---|---|---|---|---|
| Mass Fraction Aspen Alias | | | | |
| H2O | 0.009 | 0.000 | 0.088 | 0.000 |
| C16SA-ME | 0.032 | 0.153 | 0.002 | 0.106 |
| C18SA-ME | 0.053 | 0.253 | 0.000 | 0.176 |
| 18MHM-ME | 0.117 | 0.540 | 0.000 | 0.391 |
| 18DHM-ME | 0.006 | 0.025 | 0.000 | 0.282 |
| 18THM-ME | 0.001 | 0.002 | 0.000 | 0.012 |
| HEAVY | 0.005 | 0.002 | 0.000 | 0.016 |
| ETHYL-01 | 0.773 | 0.001 | 0.909 | 0.000 |
| Total Flow kg/hr | 3325.1 | 684.1 | 0.5 | 1000.0 |
| Temperature C. | 25.0 | 130.3 | 40.0 | 25.0 |
| Pressure mmHg | 750.1 | 10.0 | 0.5 | 750.1 |

Ex 31

Use a SPE to provide a saturate-reduced residue stream (Heavies) with distillate being fed to multiple packed distillation columns (packed using the same BX type of packing as in Ex 7 above) as shown in FIG. 14 below. As shown in FIG. 14, distillate from the SPE passes sequentially through two distillate distillation columns, nominally SPE, "SAT-1" and "SAT-OUT", to effect separation of the distillate stream is separated into, for example, a saturate-rich stream, a monol-rich stream, and a diol-rich stream. The heavies produced by the SPE are reduced in saturates and may be used in applications where monol, diols, triol and heavies may be advantageously used in the absence of saturates.

flash block feeding the next flash block in the cascade for residue streams from the first three flash blocks and vapor streams from the four blocks being combined and condensed as described hereinabove.

Operate SPE-3 with sufficient thermal driving force and a mass D:F ratio of 0.558 to effect separation heated Feedstream A into a residue product (R-3D) that is rich in heavies relative to Feedstream A and a distillate product (SAT1-FD) that is rich saturates relative to Feedstream A.

SAT-1, modeled using eight (8) equilibrium stages, has an overhead stream (SAT1-D) with a reduced monol content and a bottoms stream (SAT1-B) that has a reduced saturate content, each reduction being relative to SAT1-FD. SAT1-B design specifications are: 0.007 mass fraction methyl palmitate (C16SA-ME) and methyl stearate (C18SA-ME).

SAT1-D has a design specification of 0.007 mass fraction monol (18MHM-ME) in SAT1-D. Control saturate level in SAT1-B by varying D:F and monol level in SAT1-D by varying SAT-1 reflux ratio. In this case, a reflux ratio of 0.30 meets SAT1-D design specifications. SAT-1 has an overhead pressure specification of 0.1 mm Hg.

Feed SAT1-B to SAT-OUT. Design specifications for SAT-OUT include: 0.007 mass fraction based upon monol (18MHM-ME) in bottoms stream SAT-OUT-B and 0.0055 mass fraction diol (18DHM-ME) in distillate stream SAT-OUT-D. Control saturate level in SAT-OUT-B by varying D:F ratio and monol in SAT-OUT-D by varying the SATOUT column reflux ratio. In this case, a SATOUT column reflux ratio of 5.55 meets SAT-OUT-D design specifications. SAT-OUT has the same overhead pressure specification as SAT-1. Table 28 below summarizes simulation results from this Ex. 31.

Model WFE-3 using two cascaded flash blocks. Operate WFE-3 with sufficient thermal driving force and a mass D:F ratio of 0.670 to effect separation heated Feedstream A into a residue product (R-3D) that is rich in heavies relative to Feedstream A and a distillate product (SAT1-FD) that is rich saturates relative to Feedstream A.

Model SAT-1 as in Ex 31, but use the following design specifications: a) for SAT1-B: 0.007 mass fraction methyl palmitate (C16SA-ME) and methyl stearate (C18SA-ME); and b) for SAT1-D:0.007 mass fraction monol (18MHM-ME) in SAT1-D. In this case, a SAT-1 reflux ratio of 2.66 meets associated design specifications.

SAT-OUT has the following design specifications: 0.0075 mass fraction based upon monol (18MHM-ME) in bottoms stream SAT-OUT-B and 0.0075 mass fraction diol (18DHM-

TABLE 28

| | FEED | STG3-FD | R-3D | HEAVIES | SAT1-FD | SAT1-D | SATU-RATE | SAT1-B | SATOUTFD | SAT OUT-D | SAT OUT-B | MONOL | DIOL |
|---|---|---|---|---|---|---|---|---|---|---|---|---|---|
| Mass Frac Aspen Alias | | | | | | | | | | | | | |
| C16SA-ME | 0.110 | 0.110 | 0.000 | 0.000 | 0.197 | 0.384 | 0.384 | 0.000 | 0.000 | 0.000 | 0.000 | 0.000 | 0.000 |
| C18SA-ME | 0.180 | 0.180 | 0.009 | 0.009 | 0.316 | 0.609 | 0.609 | 0.007 | 0.007 | 0.009 | 0.000 | 0.009 | 0.000 |
| 18MHM-ME | 0.390 | 0.390 | 0.382 | 0.382 | 0.396 | 0.007 | 0.007 | 0.806 | 0.806 | 0.986 | 0.007 | 0.986 | 0.007 |
| 18DHM-ME | 0.280 | 0.280 | 0.521 | 0.521 | 0.089 | 0.000 | 0.000 | 0.183 | 0.183 | 0.006 | 0.968 | 0.006 | 0.968 |
| 18THM-ME | 0.015 | 0.015 | 0.031 | 0.031 | 0.002 | 0.000 | 0.000 | 0.005 | 0.005 | 0.000 | 0.025 | 0.000 | 0.025 |
| HEAVY | 0.025 | 0.025 | 0.056 | 0.056 | 0.000 | 0.000 | 0.000 | 0.000 | 0.000 | 0.000 | 0.001 | 0.000 | 0.001 |
| Total Flow kg/hr | 1000.0 | 1000.0 | 442.3 | 442.3 | 557.7 | 286.0 | 286.0 | 271.6 | 271.6 | 221.6 | 50.0 | 221.6 | 50.0 |
| Temperature C. | 100.0 | 150.0 | 160.2 | 50.0 | 50.0 | 40.0 | 40.0 | 196.2 | 150.0 | 50.0 | 233.5 | 50.2 | 50.0 |
| Pressure mmHg | 10.00 | 10.00 | 0.10 | 760.00 | 760.00 | 0.10 | 10.00 | 1.22 | 5.00 | 0.10 | 1.89 | 760.00 | 760.00 |

Ex 32

Figure 15:
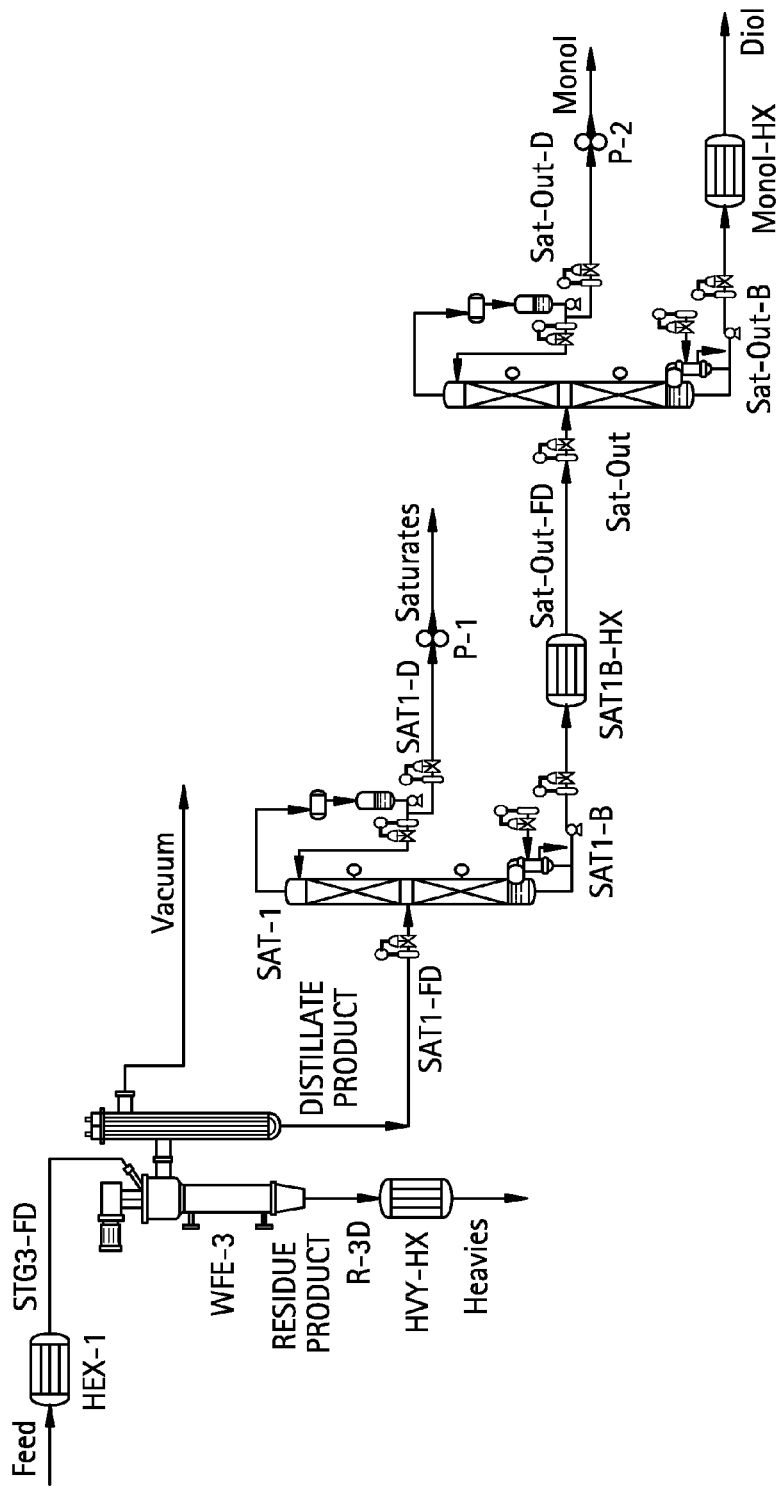
FIG. 15 is a schematic illustration of a variation of FIG. 14 using a WFE as a specific SPE as in Ex 32 below.

Replicate Ex 31, but use a WFE (nominally WFE-3) as a specific case rather than a generic SPE as in Ex 31 to effect separation of heated Feedstream A. FIG. 15 below provides a schematic illustration of a combination resulting from that substitution.

ME) in distillate stream SAT-OUT-D. Control saturate level in SATOUT-B by varying D:F ratio and monol in SAT-OUT-D by varying the SAT-OUT column reflux ratio. In this case, a SAT-OUT column reflux ratio of 2.74 meets associated design specifications. Table 29 below summarizes simulation results from this Ex. 32.

TABLE 29

| | FEED | STG3-FD | R-3D | HEAVIES | SAT1-FD | SAT1-D | SATU-RATE | SAT1-B | SATOUTFD | SAT OUT-D | SAT OUT-B | MONOL | DIOL |
|---|---|---|---|---|---|---|---|---|---|---|---|---|---|
| Mass Frac Aspen Alias | | | | | | | | | | | | | |
| C16SA-ME | 0.110 | 0.110 | 0.001 | 0.001 | 0.164 | 0.384 | 0.384 | 0.000 | 0.000 | 0.000 | 0.000 | 0.000 | 0.000 |
| C18SA-ME | 0.180 | 0.180 | 0.009 | 0.009 | 0.264 | 0.609 | 0.609 | 0.007 | 0.007 | 0.009 | 0.000 | 0.009 | 0.000 |
| 18MHM-ME | 0.390 | 0.390 | 0.302 | 0.302 | 0.433 | 0.007 | 0.007 | 0.752 | 0.752 | 0.983 | 0.008 | 0.983 | 0.008 |
| 18DHM-ME | 0.280 | 0.280 | 0.575 | 0.575 | 0.134 | 0.000 | 0.000 | 0.235 | 0.235 | 0.007 | 0.965 | 0.007 | 0.965 |
| 18THM-ME | 0.015 | 0.015 | 0.038 | 0.038 | 0.004 | 0.000 | 0.000 | 0.006 | 0.006 | 0.000 | 0.027 | 0.000 | 0.027 |
| HEAVY | 0.025 | 0.025 | 0.075 | 0.075 | 0.000 | 0.000 | 0.000 | 0.000 | 0.000 | 0.000 | 0.001 | 0.000 | 0.001 |

TABLE 29-continued

|  | FEED | STG3-FD | R-3D | HEAVIES | SAT1-FD | SAT1-D | SATU-RATE | SAT1-B | SATOUTFD | SAT OUT-D | SAT OUT-B | MONOL | DIOL |
|---|---|---|---|---|---|---|---|---|---|---|---|---|---|
| Total Flow kg/hr | 1000.0 | 1000.0 | 330.9 | 330.9 | 669.1 | 286.0 | 286.0 | 383.1 | 383.1 | 292.2 | 90.9 | 292.2 | 90.9 |
| Temperature C. | 100.0 | 150.0 | 161.6 | 50.0 | 189.6 | 40.0 | 40.0 | 195.9 | 150.0 | 50.0 | 226.5 | 50.2 | 50.0 |
| Pressure mmHg | 10.00 | 10.00 | 0.10 | 760.00 | 1.00 | 0.10 | 10.00 | 1.15 | 5.00 | 0.10 | 1.38 | 760.00 | 760.00 |

The invention claimed is:

1. A method of separating at least one component from a composition that comprises at least two seed oil derivatives selected from hydroformylated fatty acid alkyl esters or hydroformylated and hydrogenated fatty acid alkyl esters, the method comprising steps:
   a. subjecting the composition to a first separation operation, the first operation comprising a short contact time or low residence time evaporation, a low pressure (high vacuum) operation, a stripping operation, or a polarity driven separation operation, the first separation selectively partitioning the composition into a first portion and a first remainder, the first portion comprising monols and diols, or a mixture of diols and heavies, or saturated compounds;
   b. subjecting the first remainder to at least one additional separation operation, the additional operation comprising a short contact time or low residence time evaporation, a low pressure operation, a stripping operation, or a polarity driven separation operation, each additional separation being the same as, or different from, each other and the first separation, the additional separation operation selectively partitioning the first remainder into at least one additional portion and at least one additional remainder, the additional portion being the same as, or different from, the first portion; and
   c. recycling at least a portion of the additional remainder to the first separation as a co-feed with the composition, wherein the short contact time or low residence time evaporation operation occurs via use of an apparatus selected from a group consisting of a falling film evaporator, a wiped film evaporator, a rolled film evaporator, a horizontal evaporator, or a short path evaporator; the low pressure operation occurs via use of an apparatus selected from a group consisting of a packed tower distillation device, and a dividing wall column; the stripping operation occurs via an apparatus selected from a group consisting of a steam stripping device, an inert gas stripping device and a condensable vapor stripping device; and the polarity driven separation operation occurs via use of a chromatographic separation device.

2. The method of claim 1, wherein the alkyl esters are methyl esters.

3. The method of claim 1, wherein the chromatographic separation device is a simulated moving bed.

4. The method of claim 1, wherein the first separation operation occurs via a packed distillation tower and the first portion comprises saturates.

5. The method of claim 1, further comprising a pre-treatment step that precedes step a, the pre-treatment step comprising subjecting the composition to conditions sufficient to effectively de-gas the composition, thereby removing at least a portion of volatile compounds that have a normal boiling point (standard pressure and temperature) of less than 150 degrees centigrade.

6. The method of claim 1, wherein the additional separation operation occurs via an apparatus comprising a series of cascaded short path evaporator and rectifier combinations and the additional separation effects removal of at least a portion of monols and diols contained in the first remainder.

7. The method of claim 1, wherein the short contact time or low residence time evaporation operation is combined with rectification; and the low pressure operation apparatus is a packed tower distillation device that contains an ultra-low pressure drop packed section.

8. The method of claim 7, wherein the packed section has a pressure drop of less than or equal to about 20 millimeters of mercury.

9. The method of claim 1, wherein at least one of the first separation operation and an additional separation operation effects separation of saturated components of the composition from monol and diol fractions of the composition by way of a simulated moving bed.

10. The method of claim 1, wherein the first portion comprises monols and diols and an additional separation effects separation of the first portion into a monol-rich fraction and a diol-rich fraction by way of a simulated moving bed.

11. The method of claim 10, wherein the simulated moving bed employs a combination of a solvent and an adsorption media, the combination being selected from a group consisting of solvents or mixtures of solvents characterized by a MOSCED polarity parameter, tau, in the range of 4 to 12 (J/mL)" 0.5, a MOSCED acidity parameter, alpha, in the range of zero to 6 (J/mL)" 0.5, and a MOSCED basicity parameter, beta, in the range of 1 to 12 (J/mL)" 0.5, and silica gel or alumina or ion-exchange polymer beads as adsorbent media.

12. The method of claim 10, wherein the simulated moving bed employs a combination of a solvent and an adsorption media, the combination being selected from a group consisting of ethyl acetate as solvent and silica gel as media, acetonitrile as solvent and silica gel as media, methylisobutyl ketone (MIBK) as solvent and silica gel as media, tetrahydrofuran (THF) as solvent and silica gel as media, methyl tert butylether (MTBE) as solvent and silica gel as media, toluene as solvent and silica gel as media; and a mixture of heptane and ethanol as solvent and alumina as media.

* * * * *